(12) United States Patent
Chen et al.

(10) Patent No.: US 11,292,878 B2
(45) Date of Patent: Apr. 5, 2022

(54) POLY(L-LYSINE ISOLPHTHALAMIDE) (PLP) POLYMERS WITH HYDROPHOBIC PENDANT CHAINS

(71) Applicant: Rongjun Chen, Sand Hutton (GB)

(72) Inventors: Rongjun Chen, London (GB); Siyuan Chen, Huzhou (CN); Liwei Wu, Chengdu (CN)

(73) Assignee: Rongjun Chen, London (GB)

( * ) Notice: Subject to any disclaimer, the term of this patent is extended or adjusted under 35 U.S.C. 154(b) by 660 days.

(21) Appl. No.: 16/277,781

(22) Filed: Feb. 15, 2019

(65) Prior Publication Data

US 2019/0248956 A1 Aug. 15, 2019

Related U.S. Application Data

(63) Continuation of application No. 16/246,250, filed on Jan. 11, 2019, now abandoned, which is a continuation of application No. PCT/GB2017/052058, filed on Jul. 13, 2017.

(30) Foreign Application Priority Data

Jul. 13, 2016 (GB) ...................... 1612150

(51) Int. Cl.
| | |
|---|---|
| C08G 69/48 | (2006.01) |
| A61K 47/34 | (2017.01) |
| A61K 47/64 | (2017.01) |
| C08G 69/10 | (2006.01) |
| C12Q 1/02 | (2006.01) |

(52) U.S. Cl.
CPC .............. *C08G 69/48* (2013.01); *A61K 47/34* (2013.01); *A61K 47/645* (2017.08); *C08G 69/10* (2013.01); *C12Q 1/025* (2013.01)

(58) Field of Classification Search
None
See application file for complete search history.

(56) References Cited

FOREIGN PATENT DOCUMENTS

| WO | WO2004/052402 | 6/2004 |
| WO | WO2011/089391 | 7/2011 |

OTHER PUBLICATIONS

Eccleston et I. J. Controlled Release (2010) 69: 297-307 (Year: 2010).*
Chen, R. et al., "The role of hydrophobic amino acid grafts in the enhancement of membrane-disruptive activity of pH-responsive pseudo-peptides," *Biomaterials*, 30(10):1954-1961 (Apr. 2009).
Chen, R. et al., "Effect of l-Leucine Graft Content on Aqueous Solution Behavior and Membrane-Lytic Activity of a pH-Responsive Pseudopeptide," *Biomacromolecules*, 10(9):2601-2608 (Jul. 2009).
Combined Search and Examination Report for GB1612150.1, dated May 31, 2017.
International Search Report and Written Opinion for PCT/GB2017/052058, dated Nov. 8, 2017.
Khormaee, S. et al., "The Influence of Aromatic Side-Chains on the Aqueous Properties of pH-Sensitive Poly(L-lysine iso-phthalamide) Derivatives," *Journal of Biomaterials Science*, 21(12):1573-1588 (Nov. 2010).
Zhang, S. et al., "The Effects of Substituent Grafting on the Interaction of pH-Responsive Polymers with Phospholipid Monolayers," *Langmuir*, 27(13):8530-8539 (Jul. 2011).
Watkins, K.A. et al., "pH-responsive, lysine-based hydrogels for the oral delivery of a wide size range of molecules," *International Journal of Pharmaceutics*, 478(2):496-503 (Dec. 2014).

\* cited by examiner

*Primary Examiner* — Susan M Hanley
(74) *Attorney, Agent, or Firm* — Klarquist Sparkman, LLP

(57) ABSTRACT

The present disclosure relates to the provision of novel biodegradable amphiphilic peptides and peptide analogues based derivatives comprising hydrophobic chains and their use in the permeabilization of mammalian cells and delivery of agents, for example therapeutic agents, imaging agents and cell preservation agents.

30 Claims, 43 Drawing Sheets

Figure 15:
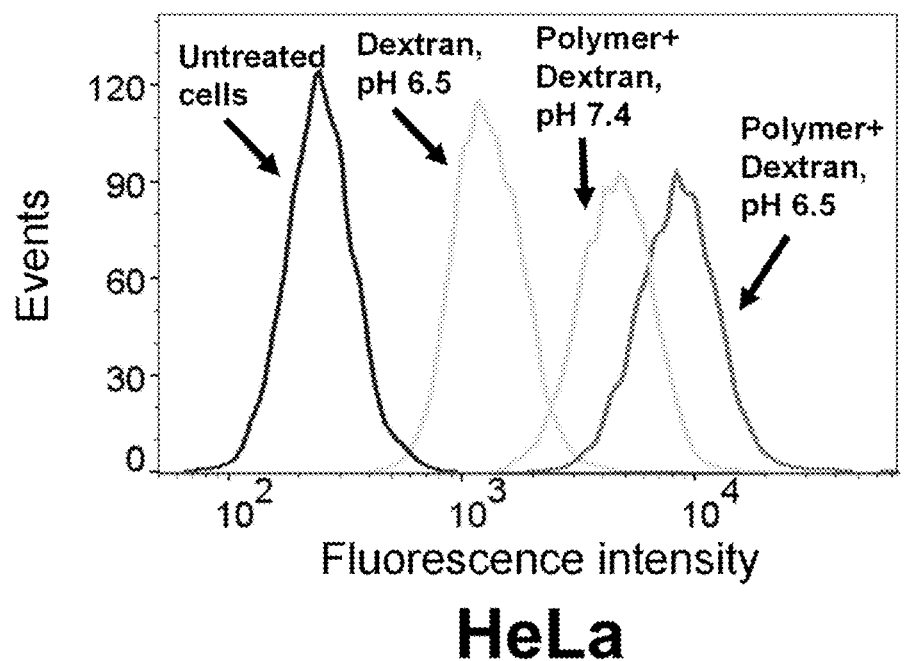
Figure 15:
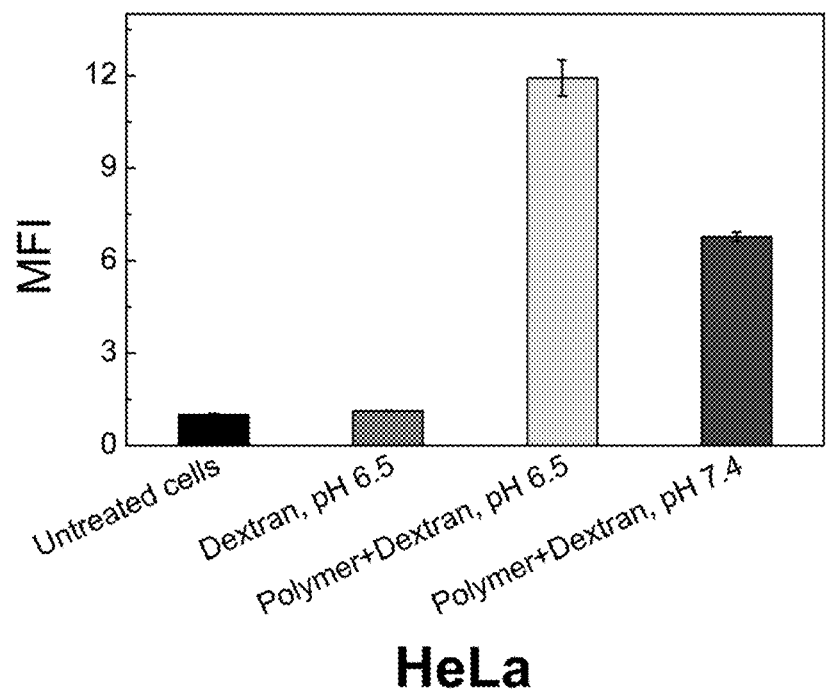
Figure 15:
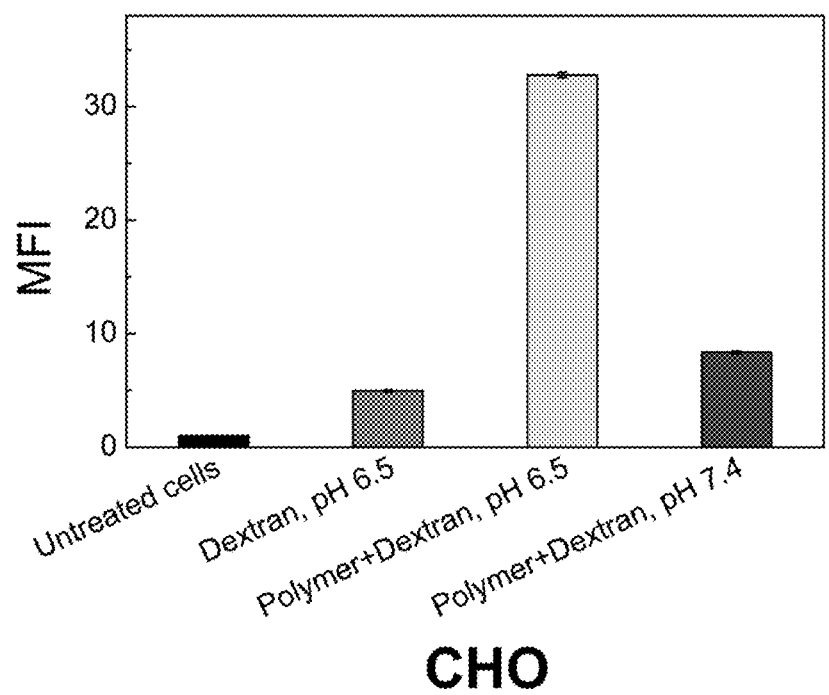

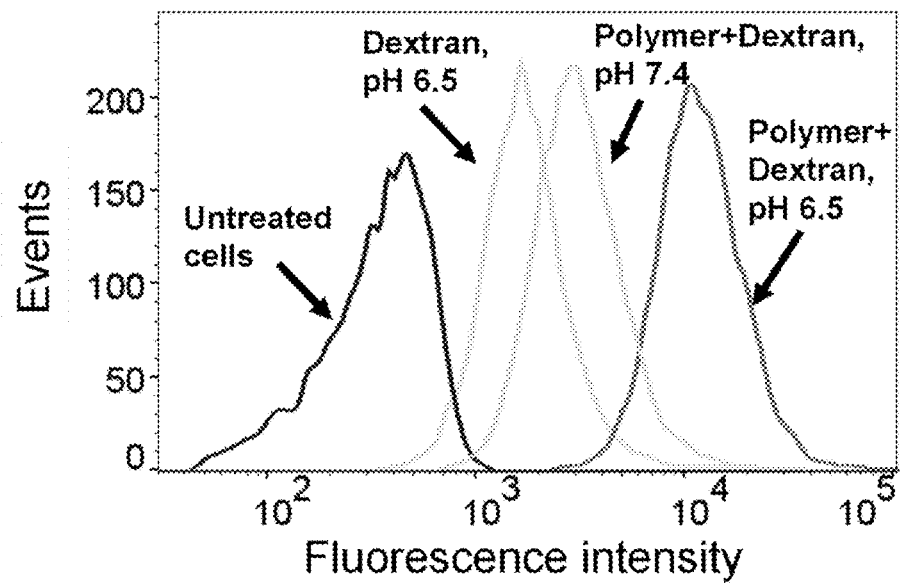
CHO
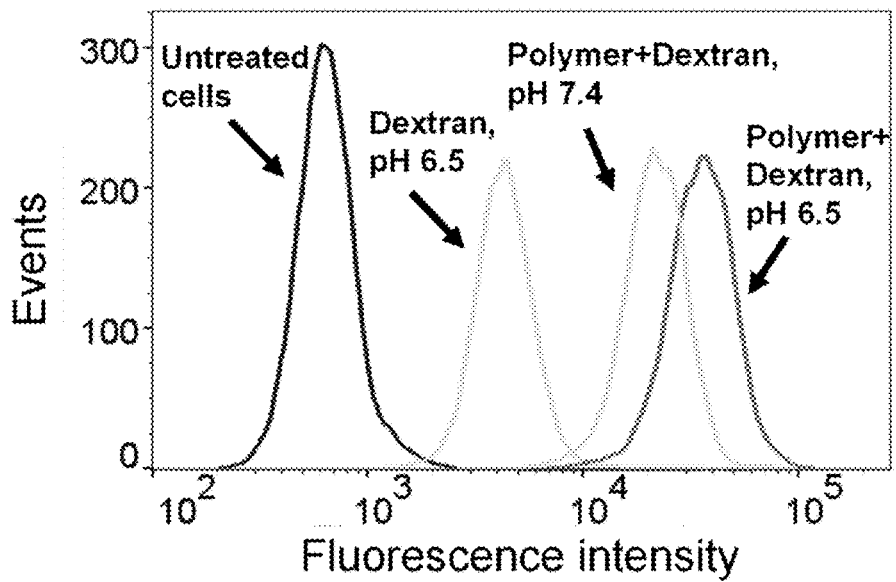
A549
Figure 15 (A), cont'd

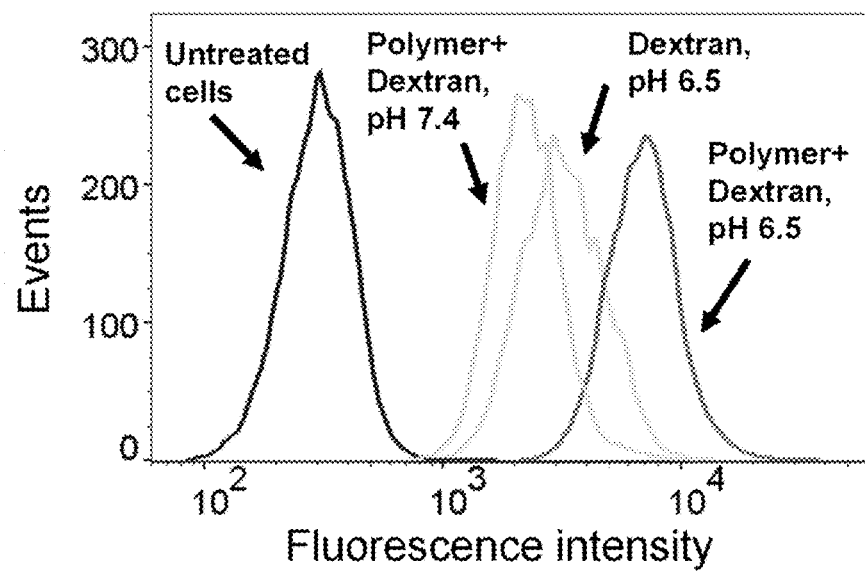
SU-DHL-8
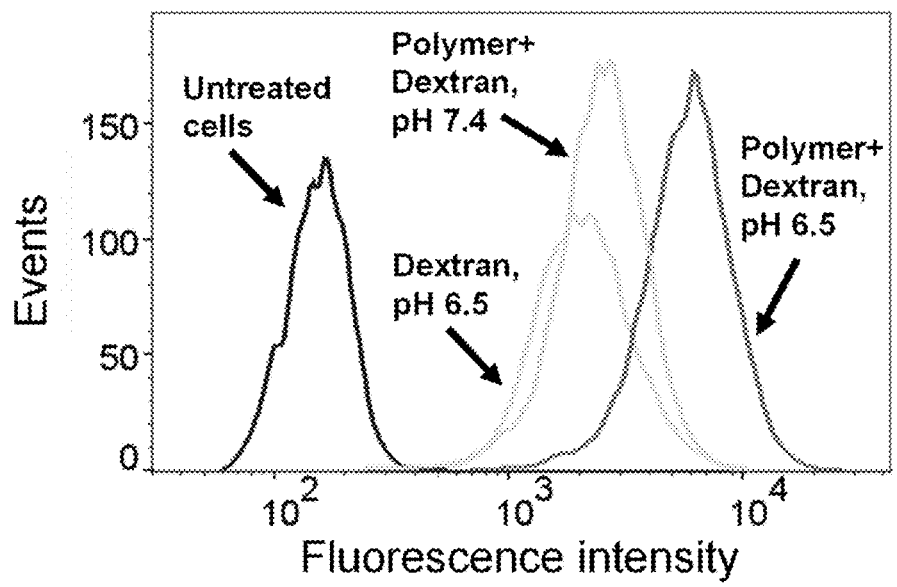
MES-SA
Figure 15 (A), cont'd

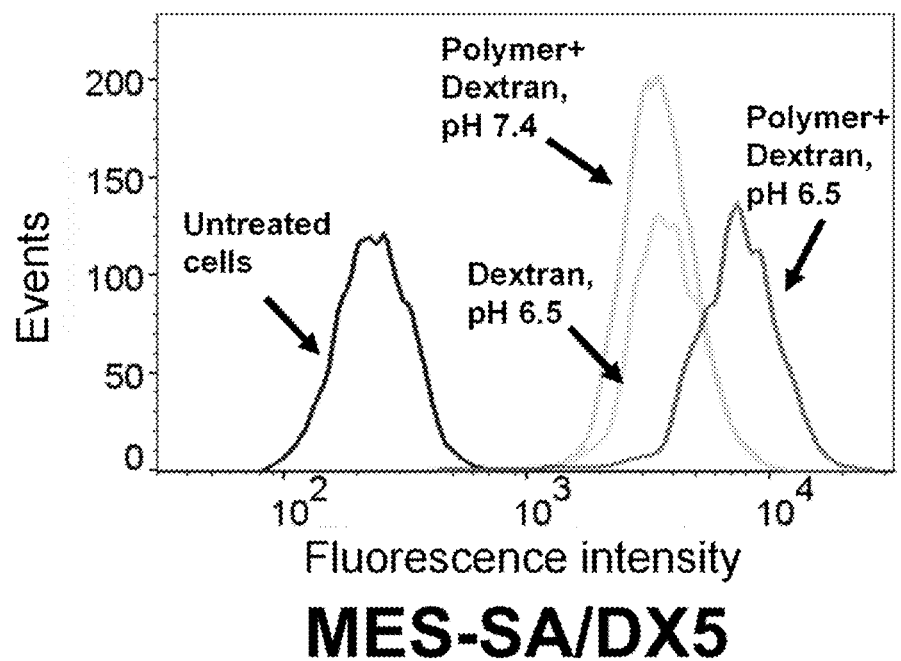
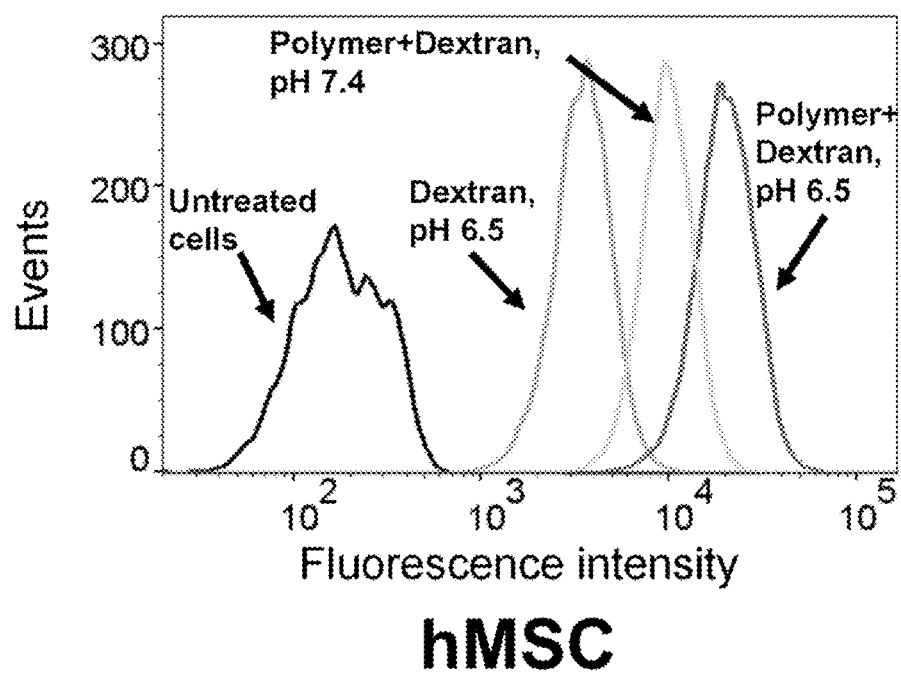
Figure 15 (A), cont'd

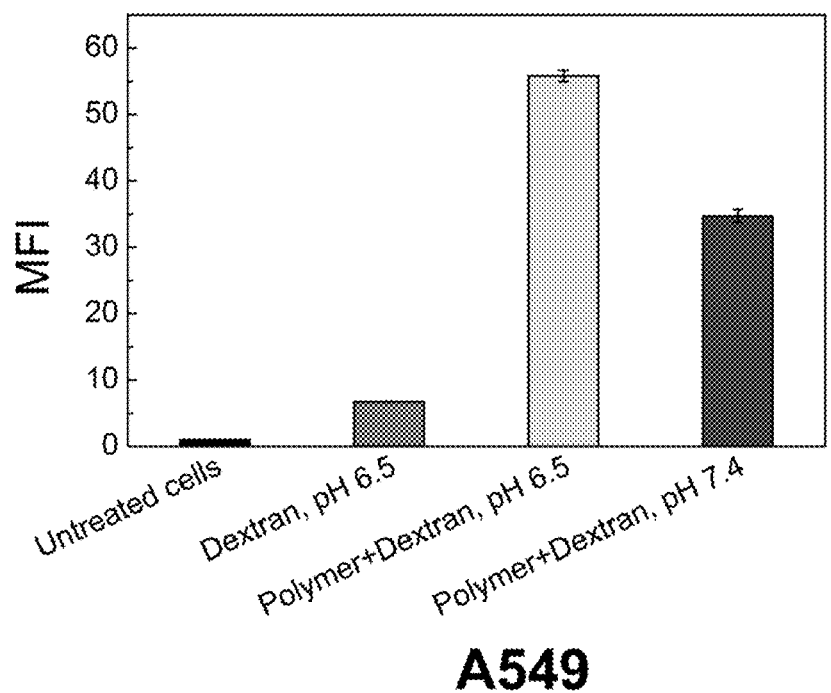
A549
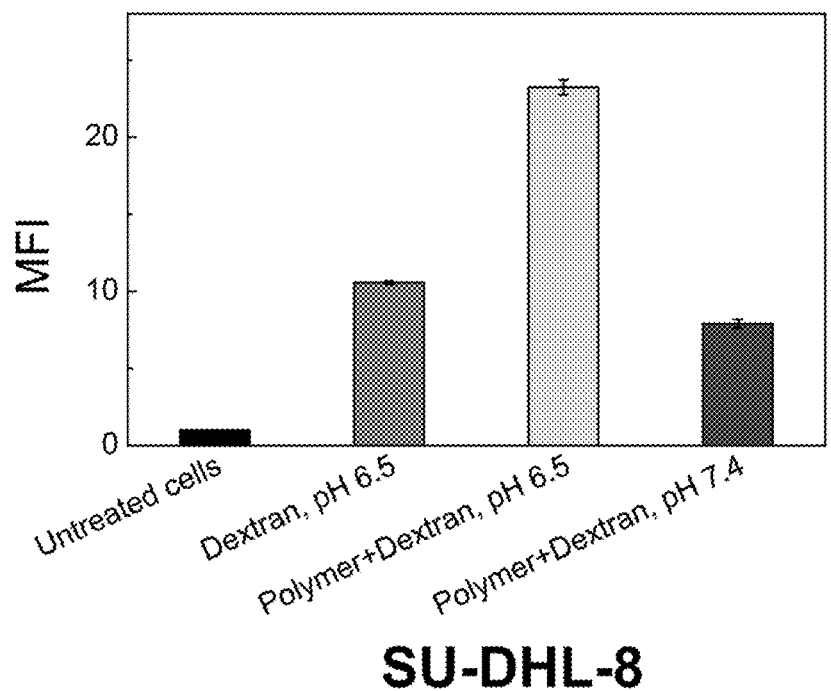
SU-DHL-8
Figure 15 (B), cont'd

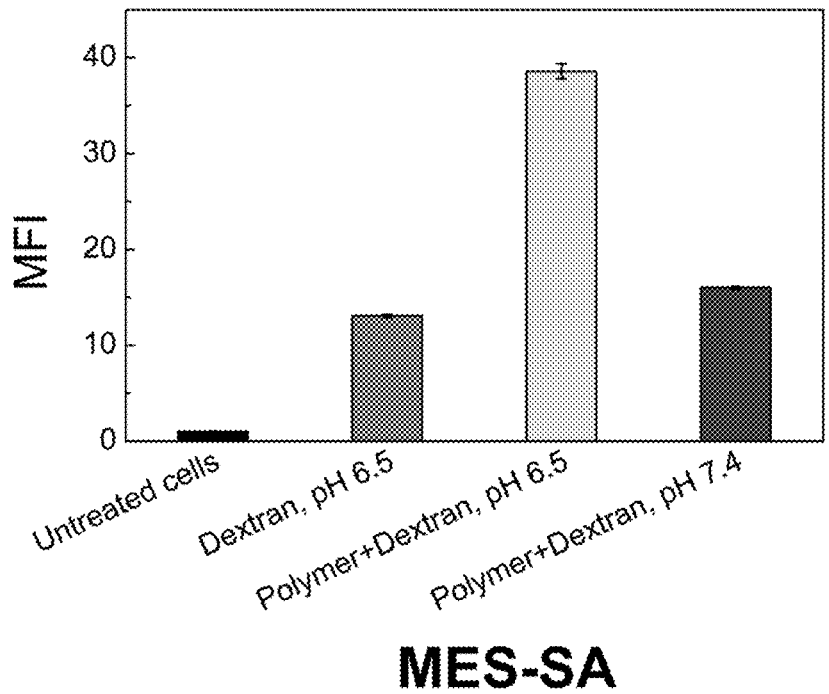
MES-SA
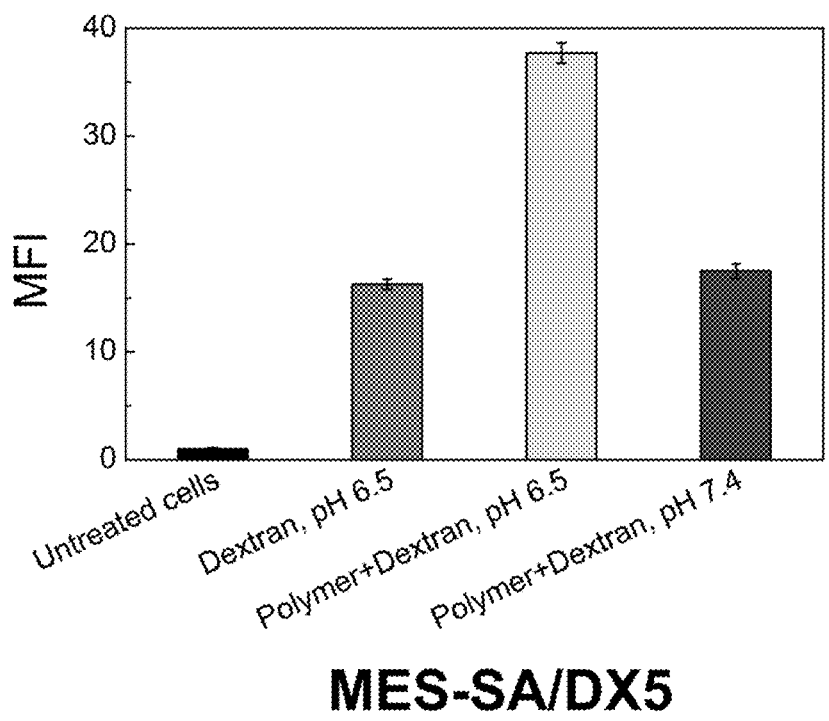
MES-SA/DX5
Figure 15 (B), cont'd

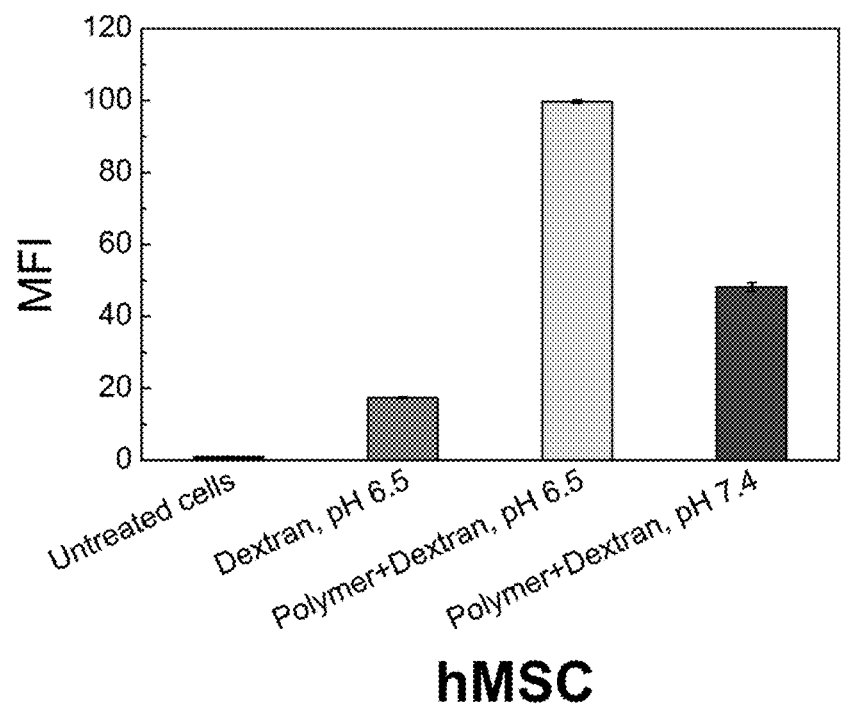
Figure 15 (B), cont'd

Figure 30:
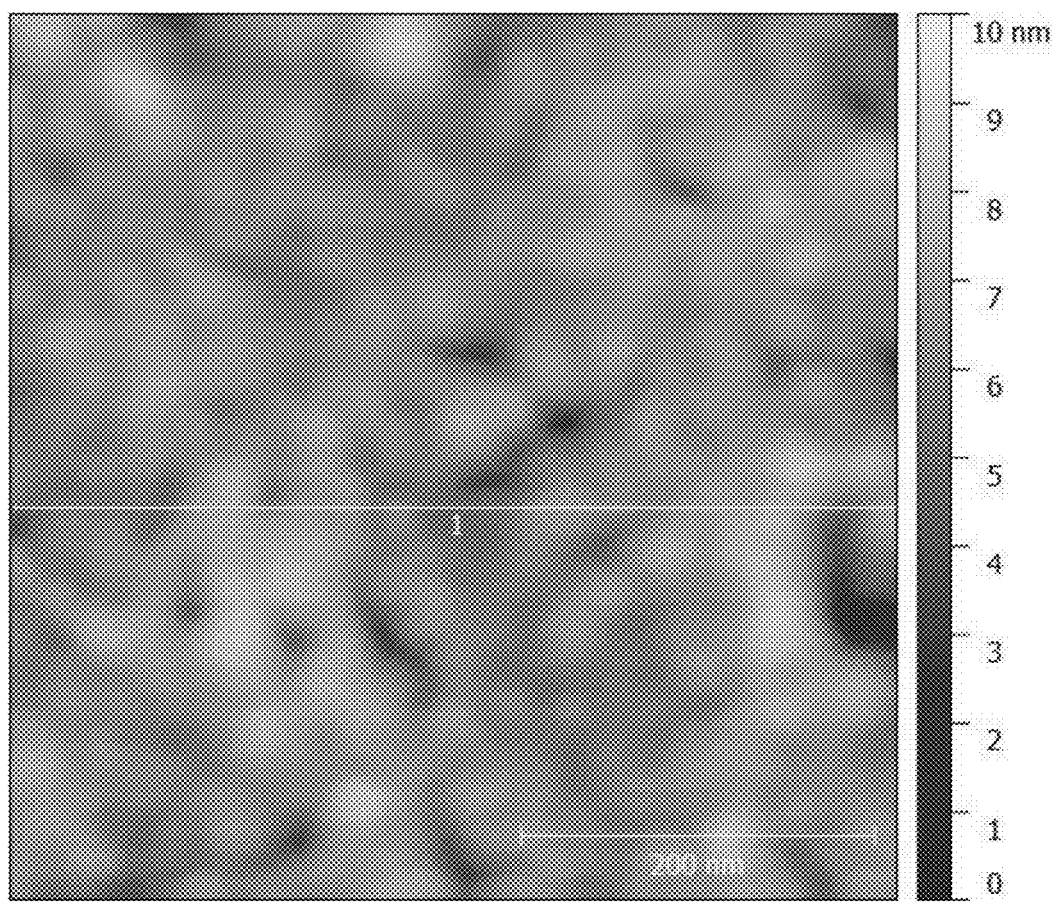

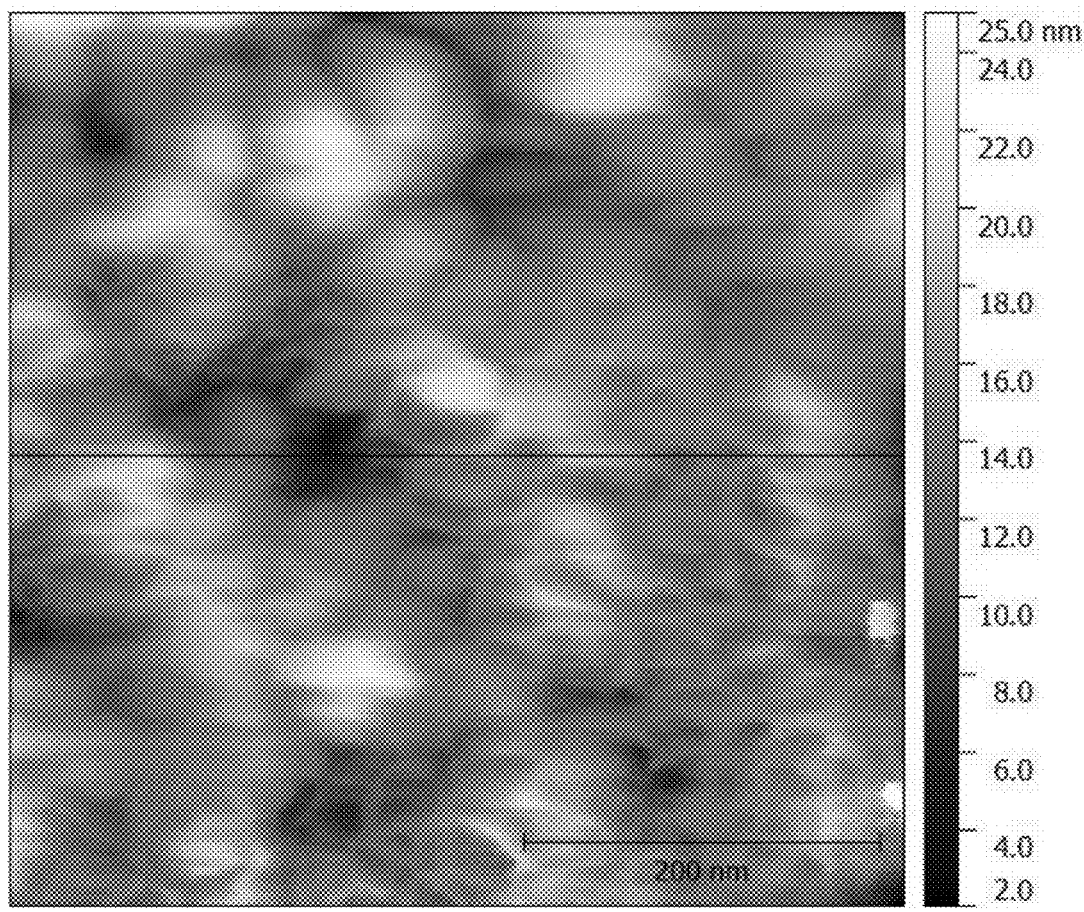
PP50
Figure 30, cont'd

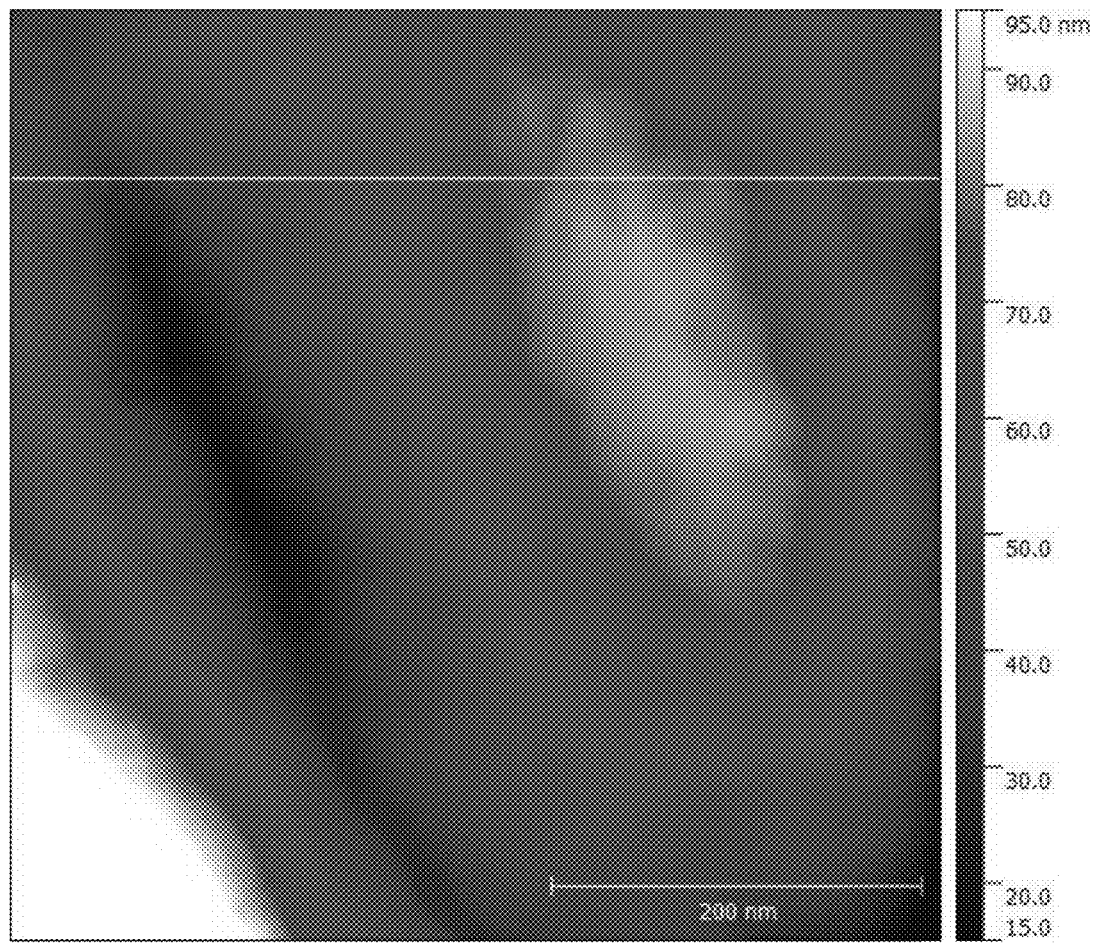
PLP-NDA 18%
Figure 30, cont'd

POLY(L-LYSINE ISOLPHTHALAMIDE) (PLP) POLYMERS WITH HYDROPHOBIC PENDANT CHAINS

CROSS REFERENCE TO RELATED APPLICATION

This application is a continuation of U.S. patent application Ser. No. 16/246,250, filed Jan. 11, 2019, which is a continuation of International Application No. PCT/GB2017/052058, filed Jul. 13, 2017, published in English under PCT Article 21(2), which claims the benefit of GB Application No. 1612150.1, filed Jul. 13, 2016, which applications are herein incorporated by reference in their entireties.

FIELD

The present disclosure relates to the provision of novel biodegradable amphiphilic peptide- and peptide analogue-based derivatives comprising hydrophobic pendant chains; their use in the permeabilization of mammalian cells and the use of the peptide- or peptide analogue-based derivatives in the intracellular delivery of one or more agents.

BACKGROUND

The application of nanoparticles in biology and medicine has rapidly grown in recent years due to their advantageous physical and chemical properties. Nanoparticles can be found composed of a variety of inorganic or organic materials and are used in various biomedical applications such as cell therapy, tissue engineering, biomarkers, labelling and tracking agents, vectors for gene therapy, magnetic resonance imaging (MRI), imaging agents and drug delivery.

For the purpose of drug delivery, nanoparticles are defined as biocompatible submicron sized particles (<1 µm) in which the desired drug is dissolved, encapsulated, complexed or covalently attached. Nanoparticles have to fulfil a wide range of often conflicting technical characteristics to be useful in biomedical applications. It is essential for nanoparticles to be highly stable to allow targeted drug delivery and sustained release. Nanoparticles are desired to have amphiphilic properties permitting the transport of both hydrophilic and hydrophobic compounds and offer suitability for chemical modification which limits often the choices of materials. Additionally, nanoparticles have to be tailored to fit various routes of administration such as oral administration or administration by inhalation. Another important aspect is that nanoparticles are composed of biocompatible, biodegradable material such as synthetic or natural polymers or lipids to minimise the risk of rejection and avoid degradation to toxic components. Organic biodegradable polymers such as polyhydroxybuterate (PHB), poly lactic acid (PLA), poly caprolactam (PCL), poly amino acids, poly amides, poly glycidols and others are currently considered as suitable materials for the development of nanoparticles for drug delivery. A further objective of nanoparticle based delivery vehicles is to provide means by which therapeutic agents are specifically targeted to cells in the treatment of diseases and disorders that reduce dosages and thereby reduce side effect profiles thereby providing improved treatment regimens for patients.

Biodegradable pseudo-peptidic polymers have been designed and used as polymeric permeabilization agents in the delivery of agents. For example, in WO2011089391, is disclosed the use of such polymers with one or more hydrophobic amino acids grafted onto the carboxylic acid groups of poly(L-lysine iso phthalamide) (PLP) to reversibly permeabilise a cell membrane to improve uptake of agents for example trehalose, which is a known cytoprotectant agent. In WO2004/052402 pseudo-peptide based polymeric agents are disclosed for use in the delivery of therapeutic agents optionally associated with nanoparticles such as chemotherapeutics, antibodies, antibiotics and siRNA and the delivery of imaging agents.

Improved methods for the preservation and long term storage of biological products are urgently needed to protect and store valuable biological samples such as haematopoietic cells (e.g. red blood cells, platelets and lymphocytes), stem cells (e.g. bone marrow cells), immune cells, reproductive cells for use in clinical medicine and biopharmaceutical applications. Cell cryopreservation is routinely used in laboratories to extend cellular life and involves traditional slow freezing methods or ultra-fast freezing of cells or tissue at sub-zero temperatures aiming to reduce any damaging enzymatic and chemical activities in the cell. However, although freezing can extend cell life, it can also result in cell damage caused by inter- or extracellular ice crystal formation or osmotic shock. Cyroprotective methods such as freezing or vitrifying cells are therefore often performed in the presence of cyroprotective agents (CPA) aiming to protect cellular structures from damage during the cooling and warming process such as dimethyl sulfoxide, glycerol, 1,2-propanediol, hydroxyethyl starch or polyethylene glycol, and although these compounds are known to have beneficial effects, controlled addition and removal of CPAs is necessary to prevent cell lysis, cell differentiation and toxicity. For example, dimethylsulfoxide (DMSO) is the currently the most widely used cryoprotectant in cell storage; however, DMSO is highly toxic and results in 30% death of mesenchymal stem cells and approximately 50% death of human embryonic stem cells. Moreover, approximately 1.5% of patients obtaining cells stored with the CPA experience extreme side effects such as respiratory and/or cardiovascular problems.

Natural cell preservation methods are known from the multicellular organism Tardigrada which can survive freezing due to the presence of high concentrations of trehalose in the cell. Small carbohydrates sugars such as trehalose, sucrose or maltose are known to have physiochemical properties which are superior to traditional CPAs such as DMSO or glycerol and are known in the art. WO2012/098358 discloses trehalose and other carbohydrates as preservation agents in combination with different buffers and reconstitution solution to improved viability and functionality of the freeze dried cell.

However, although superior in their cyroprotective properties small sugars are difficult to transport across the cell membrane into the cell which is necessary to obtain any cyroprotective effect. In order to improve sugar uptake methods such as microinjection, electro-permeabilization or increase of cell permeabilization by using bacterial toxins have been developed. US2005277107 discloses compositions comprising carbohydrates such as trehalose for delivery into a cell by microinjection. U.S. 61/227,177 discloses the use of the H5-alpha toxin for the temporary poration of the cell for loading of bio-preservative agents such as trehalose. Polymeric compounds such as modified vinyl polymers (vinyl poly (alpha-alkylarcylic acid) polymers) are known to disrupt the lipid bilayer membrane at endosomal pH values and have potential application in cytoplasmic drug delivery. However, vinyl polymers are not biodegradable.

The present disclosure relates to the provision of novel amphiphilic peptide- and peptide analogue-based derivatives comprising hydrophobic side chains, such as aliphatic alkane side chains, and the use of such peptide- or peptide analogue-based derivatives to increase uptake of agents through the permeabilization of cell membranes. For example, the use of peptide- or peptide analogue-based derivatives for the delivery of agents that protect cells, tissues and organs from the detrimental effects of freezing or drying. In addition, the peptide derivatives have utility in the delivery of therapeutic agents in the treatment of diseases and disorders.

STATEMENTS OF THE INVENTION

According to an aspect of the invention there is provided an amphiphilic peptide or amphiphilic peptide analogue wherein said peptide comprises one or more hydrophobic pendant chains.

Suitably the hydrophobic pendant chain is a $C_{1-200}$ alkyl, $C_{2-200}$ alkenyl or $C_{2-200}$ alkynyl group, any of which may be substituted with one or more substituents selected from halo, cyano, nitro, azo, diazonium, phosphate, phosphate ester, $NR^3R^4$, $C(O)OR^3$, $OR^3$, $SR^3$, $C(O)SR^3$, $C(O)NR^3R^4$, azide, $C_{6-14}$ aryl or $C_{4-14}$ heteroaryl, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, azide, phosphate, phosphate ester and wherein each of $R^3$ and $R^4$ is independently H or $C_{1-10}$ alkyl, $C_{2-10}$ alkenyl, $C_{2-10}$ alkynyl.

Suitably the hydrophobic pendant chain is $C_{5-40}$ alkyl, $C_{5-40}$ alkenyl or $C_{5-40}$ alkynyl which may be optionally substituted as described above.

In the present specification "halo" refers to fluoro, chloro, bromo or iodo.

Suitably the hydrophobic pendant chain is a $C_{6-30}$ alkyl, $C_{6-30}$ alkenyl or $C_{6-30}$ alkynyl group, any of which may be substituted with one or more substituents selected from halo, cyano, nitro, $NR^3R^4$, $C(O)OR^3$, $OR^3$, $SR^3$, $C_{6-10}$ aryl or heteroaryl, wherein aryl and heteroaryl groups are optionally substituted with one or more substituents selected from $C_{1-4}$ alkyl, $C_{1-4}$ haloalkyl, halo, cyano or nitro; and wherein each of $R^3$ and $R^4$ is independently H or $C_{1-6}$ alkyl.

Suitably, the hydrophobic pendant chain is C7 alkyl, C8 alkyl, C10 alkyl, C14 alkyl or C18 alkyl which may be optionally be substituted as described above.

Examples of suitable hydrophobic pendant chains are selected from the group consisting of octatriacontanoic acid (C38), hentriacontanoic acid (C31), docosahexaenoic acid (C22), Amino-functionalized polylactide 2500 Da and 4000 Da, amine terminated poly(N-isopropylacrylamide) 2500 Da, 5000 Da or 5500 Da, pluronics, saturated and unsaturated fatty acids, decylamine, octadecylamine, dihexylamine, dioctadecylamine, 3-butenylamine hydrochloride, oleylamine, ethyl(prop-2-en-1-yl)amine, bis[(2Z)-3-chlorobut-2-en-1-yl]amine, methyl[7-(methylimino)hepta-1,3,5-trien-1-yl]amine, but-3-yn-1-amine hydrochloride, 3-fluoro-2-methyloct-7-yn-1-amine, [4,4-dimethyl-2-(pent-4-yn-1-yl)cyclohexyl]methanamine, bis(but-2-yn-1-yl)amine, (dec-1-yn-4-yl)(propyl)amine, (8-aminoocta-1,3,5,7-tetrayn-1-yl)borane, N-(2-Naphthyl)-1-naphthylamine, c-(2-p-Tolyl-imidazo[1,2-a]pyridin-3-yl)-methylamine, 1,1-bis(4-chlorophenyl)-2-[(2-fluorobenzyl)amino]-1-ethanol, 4-tetradecylaniline bis[2-(di-tert-butylphosphino)ethyl] amine solution, 3-(Fmoc-amino)benzonitrile, h-cys(trt)-nh2, 1,7-Dibenzyl-1,4,7,10-tetraazacyclododecane, 2-(3-oxo-decahydro-quinoxalin-2-yl)-N-(4-phenoxy-phenyl)-acetamide, pontacyl carmine 2b, 2-[(2-amino-4-methylphenyl)sulfanyl]-N-(2-methylphenyl)acetamide, 4-nitrophenethylamine hydrochloride, 3-(ethoxydimethylsilyl)propylamine, (1,2,3,6-tetrahydropyridin-4-yl)phosphonic acid, poly(propylene glycol)-, polyethylene-, and polystyrene-based polymers.

Suitable hydrophobic pendant chains may be conjugated to the amphiphilic peptide or amphiphilic peptide analogue via dicyclohexylcarboiimide/dimethylaminopyridine (DCC/DMAP) coupling, 1-ethyl-3-(3-dimethylaminopropyl)-carbodiimide (EDC)/N-Hydroxysuccinimide (NHS) coupling or using other established crosslinking techniques known to the skilled artisan.

The hydrophobic pendant chain may be linked to the polymer backbone via a linker selected from a bond, —C(O)—, —C(O)O—, —C(O)NH—, —O—, —S—, —SO—, —SO$_2$—, —S(O$_2$)N—, —SS, —NN—, —CN—, —C(O)OC(O)—, —P(O)O—, —SiO—, —N$_3$—, —S(O)—, —NR—, —OP(OOH)O—, —P(OOR)—.

In a preferred embodiment of the invention said peptide analogue comprises poly (lysine isophthalamide) (PLP).

In an embodiment of the invention said peptide comprises amphiphilic polymers with weakly ionisable carboxyl acid groups, wherein said polymers comprise co-polymers of: (a) a monomer containing two carboxyl groups such as isophthalic acid or containing two acyl chlorides such as isophthaloyl chloride; and (b) a monomer containing two amine groups such as lysine, cysteine, selenocystine, 2,4-diaminopropionic acid, 2,4-diaminobutyric acid, ornithine, and 2,6-diaminopimelic acid.

In a further alternative embodiment of the invention said peptide comprises natural polyamino acids, such as poly (aspartic acid) and poly (glutamic acid), and their derivatives.

SPECIFIC EMBODIMENTS OF THE INVENTION

In an aspect or preferred embodiment of the invention there is provided a peptide comprising a compound of formula (I):

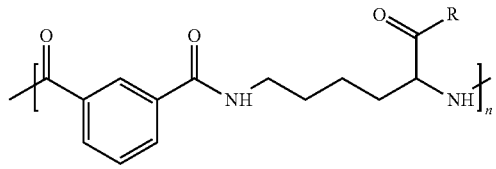

wherein R comprises
$NR^1R^2$ or OH wherein at least one of R are $NR^1R^2$;
$R^1$ and $R^2$ each independently comprises H; $C_{1-200}$ alkyl, $C_{2-200}$ alkenyl or $C_{2-200}$ alkynyl group, optionally substituted with one or more substituents selected from halo, cyano, nitro, diazonium, —OP(O)OR$^3$OR$^4$, —PR$^3$R$^4$, $NR^3R^4$, $C(O)OR^3$, $OR^3$, $SR^3$, $C(O)SR^3$, $C(O)NR^3R^4$, azide, $C_{6-14}$ aryl or $C_{4-14}$ heteroaryl,
wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, azide, OP(O)OR$^3$OR$^4$, —PR$^3$R$^4$; and wherein each of $R^3$ and $R^4$ is independently H or $C_{1-10}$ alkyl, $C_{2-10}$ alkenyl, $C_{2-10}$ alkynyl, $C_{6-10}$ aryl;

$C_{6-10}$ aryl optionally substituted with one or more substituents selected from $C_{1-16}$ alkyl, $C_{1-16}$ haloalkyl, halo, cyano, nitro, diazonium, —OP(O)OR$^3$R$^4$, —PR$^3$R$^4$, NR$^3$R$^4$, C(O)OR$^3$, OR$^3$, SR$^3$, C(O)SR$^3$, C(O)NR$^3$R$^4$, azide, $C_{6-14}$ aryl or $C_{4-14}$ heteroaryl, wherein alkyl and haloalkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$;

wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$;

wherein R$^3$ and R$^4$ are as defined above; or

R$_1$ and R$_2$ together with the nitrogen atom to which they are attached to form a 5-12-membered heterocyclic ring optionally containing one or more additional heteroatoms selected from N, O and S and optionally substituted with one or more substituents selected from $C_{1-16}$ alkyl, $C_{1-16}$ haloalkyl, halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, $C_{6-14}$ aryl or $C_{6-14}$ heteroaryl, wherein alkyl and haloalkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$ wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$;

wherein R$^3$ and R$^4$ are as defined above; and n≥4.

In an alternative embodiment said peptide is a poly(lysine isophthalamide) compound comprising general formula (I):

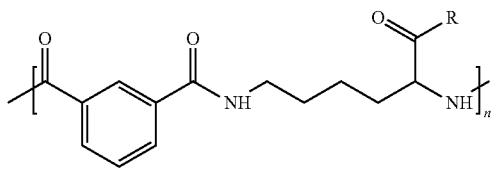

(I)

wherein R comprises
NR$^1$R$^2$ or OH wherein at least one of R are NR$^1$R$^2$;
R$^1$ and R$^2$ each independently comprises:
H;
$C_{6-30}$ alkyl, $C_{6-30}$ alkenyl or $C_{6-30}$ alkynyl, $C_{6-10}$ aryl or $C_{5-10}$ heteroaryl; wherein
Alkyl, alkenyl and alkynyl groups R$^1$ and R$^2$ are optionally substituted with one or more substituents selected from halo, cyano, nitro, diazonium, —OP(O)OR$^3$OR$^4$, —PR$^3$R$^4$, NR$^3$R$^4$, =NR$^3$, =O, C(O)OR$^3$, OR$^3$, SR$^3$, C(O)SR$^3$, C(O)NR$^3$R$^4$, azide, $C_{3-7}$ cycloalkyl, $C_{3-10}$ heterocyclyl, $C_{6-14}$ aryl or $C_{4-14}$ heteroaryl;

wherein cycloalkyl, heterocyclyl, aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$, aryl substituted with R$^3$ and heteroaryl substituted with R$^3$ and, where chemically appropriate, =O; and wherein each of R$^3$ and R$^4$ is independently H or $C_{1-10}$ alkyl, $C_{2-10}$ alkenyl, $C_{2-10}$ alkynyl, $C_{6-10}$ aryl;

$C_{6-10}$ aryl and heteroaryl groups R$^1$ and R$^2$ are optionally substituted with one or more substituents selected from $C_{1-16}$ alkyl, $C_{1-16}$ haloalkyl, halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, $C_{6-14}$ aryl, or $C_{4-14}$ heteroaryl or S—CH$_2$C(O)NR$^5$R$^6$;

wherein alkyl and haloalkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$;

wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$;

wherein R$^3$ and R$^4$ are as defined above and R$^5$ and R$^6$ are each independently H, $C_{1-6}$ alkyl optionally substituted with OR$^3$ or halo or $C_{6-14}$ aryl optionally substituted with $C_{1-6}$ alkyl, OH, O($C_{1-6}$ alkyl) or O—$C_{6-14}$ aryl; or R$^1$ and R$^2$ together with the nitrogen atom to which they are attached to form a 5-12-membered heterocyclic ring optionally containing one or more additional heteroatoms selected from N, O and S and optionally substituted with one or more substituents selected from $C_{1-16}$ alkyl, $C_{1-16}$ haloalkyl, halo, cyano, nitro, diazonium, =O, —OP(O)OR$^3$R$^4$, —PR$^3$R$^4$, NR$^3$R$^4$, C(O)OR$^3$, OR$^3$, SR$^3$, C(O)SR$^3$, C(O)NR$^3$R$^4$, azide, $C_{6-14}$ aryl or $C_{4-14}$ heteroaryl;

wherein alkyl and haloalkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$;

wherein R$^3$ and R$^4$ are as defined above; and n≥4.

In some cases, in this aspect of the invention, R$^1$ and R$^2$ each independently comprises:
H;
$C_{6-30}$ alkyl, $C_{6-30}$ alkenyl or $C_{6-30}$ alkynyl group optionally substituted with one or more substituents selected from halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, $C_{6-14}$ aryl or $C_{4-14}$ heteroaryl, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$; and wherein each of R$^3$ and R$^4$ is independently H or $C_{1-10}$ alkyl, $C_{2-10}$ alkenyl, $C_{2-10}$ alkynyl, $C_{6-10}$ aryl;

$C_{6-10}$ aryl optionally substituted with one or more substituents selected from $C_{1-16}$ alkyl, $C_{1-16}$ haloalkyl, halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, $C_{6-14}$ aryl or $C_{4-14}$ heteroaryl, wherein alkyl and haloalkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$;

wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, azide, $OP(O)OR^3OR^4$, —$PR^3R^4$;

wherein $R^3$ and $R^4$ are as defined above; or $R^1$ and $R^2$ together with the nitrogen atom to which they are attached to form a 5-12-membered heterocyclic ring optionally containing one or more additional heteroatoms selected from N, O and S and optionally substituted with one or more substituents selected from $C_{1-16}$ alkyl, $C_{1-16}$ haloalkyl, halo, cyano, nitro, diazonium, —$OP(O)OR^3OR^4$, —$PR^3R^4$, $NR^3R^4$, $C(O)OR^3$, $OR^3$, $SR^3$, $C(O)SR^3$, $C(O)NR^3R^4$, azide, $C_{6-14}$ aryl or $C_{4-14}$ heteroaryl;

wherein alkyl and haloalkyl groups are optionally substituted with one or more substituents selected from halo, cyano or nitro, $NR^3R^4$, $C(O)OR^3$, $OR^3$, $SR^3$, azide, $OP(O)OR^3OR^4$, —$PR^3R^4$, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, azide, $OP(O)OR^3OR^4$, —$PR^3R^4$;

wherein $R^3$ and $R^4$ are as defined above; and n≥4.

In a preferred compound n is between 4-3623; preferably between 4-1000, 1001-2000, 2001-3000 and even more preferably between 3001-3623.

In an alternative preferred compound n is between 4-362; preferably between 4-272, 4-181 and even more preferably between 4-150.

In an alternative preferred compound n is between 4-200; preferably between 20-170 and even more preferably between 40-140.

In an alternative preferred compound n is between 120-150; preferably n=130.

In an alternative preferred compound n is between 40-60, preferably n=49.

Examples of PLP polymers are given in patent application WO2004/052402 and US2006172418 the content of which is hereby incorporated by reference in its entirety.

The poly(lysine isophthalamide) derivative may be a poly(L-lysine isophthalamide) compound.

In an alternative compound $R^1$ and $R^2$ each independently comprise H, $C_{5-40}$ alkyl, $C_{5-40}$ alkenyl or $C_{5-40}$ alkynyl which may be optionally substituted as described above.

In an alternative compound $R^1$ and $R^2$ each independently comprise H, $C_{6-30}$ alkyl, $C_{6-30}$ alkenyl or $C_{6-30}$ alkynyl and are optionally substituted as described above.

In an alternative compound $R^1$ and $R^2$ each independently comprise H, $C_{7-22}$ alkyl, $C_{7-22}$ alkenyl or $C_{7-22}$ alkynyl and are optionally substituted as described above.

In a further alternative compound $R^1$ is H, $C_{7-22}$, alkyl, $C_{7-22}$ alkenyl or $C_{7-22}$ alkynyl and $R^2$ is $C_{7-22}$, alkyl, $C_{7-22}$ alkenyl or $C_{7-22}$ alkynyl and are optionally substituted as described above In an alternative compound aryl is $C_{1-10}$. In an alternative compound heteroaryl is $C_{6-10}$.

In an alternative compound $R^1$ and $R^2$ each independently comprises H, $C_{6-30}$ alkyl, $C_{6-30}$ alkenyl or $C_{6-30}$ alkynyl any of which may be substituted with one or more substituents selected from halo, cyano, nitro, diazonium, $OP(O)OR^3OR^4$, —$PR^3R^4$, $NR^3R^4$, $C(O)OR^3$, $OR^3$, $SR^3$, $C(O)SR^3$, $C(O)NR^3R^4$, azide, $C_{6-10}$ aryl or $C_{4-14}$ heteroaryl, wherein aryl and heteroaryl groups are optionally substituted with one or more substituents selected from $C_{1-4}$ alkyl, $C_{1-4}$ haloalkyl, halo, cyano or nitro, $NR^3R^4$, $C(O)OR^3$, $OR^3$, $SR^3$, azide, $OP(O)OR^3OR^4$, —$PR^3R^4$phosphate; and wherein each of $R^3$ and $R^4$ is independently H or $C_{1-6}$ alkyl.

In a preferred compound between 0.1-99% e.g. 0.1-5%, 0.5-10%, 1-20%, 2-19%, 3-18%, 4-17%, 5-16%, 6-15%, 7-14%, 8-13%, 9-12%, 10-95%, 15-85%, 20-80%, 25-75%, 30-70%, 35-65%, 40-60%, 45-55% of the moieties R are $NR^1R^2$.

In a further preferred compound between 3-18% of R are $NR^1R^2$.

In a further preferred compound 3, 10 or 18% of R are $NR^1R^2$.

In more suitable compounds of the present invention, $R^1$ and $R^2$ are not both H. Therefore, suitably, $R^1$ is as defined above and $R^2$ is as defined above except that it is not hydrogen.

In some suitable compounds, $R^1$ is as defined above and $R^2$ is $C_{6-30}$ alkyl, $C_{6-30}$ alkenyl or $C_{6-30}$ alkynyl, $C_{6-10}$ aryl or $C_{5-10}$ heteroaryl, any of which is optionally substituted as defined above.

More suitably, $R^1$ is H, $C_{6-30}$ alkyl, $C_{6-30}$ alkenyl or $C_{6-30}$ alkynyl, any of which may optionally be substituted as defined above and $R^2$ is $C_{6-30}$ alkyl, $C_{6-30}$ alkenyl or $C_{6-30}$ alkynyl, any of which may optionally be substituted as defined above.

In some suitable compounds of the invention, $R^1$ is H or $C_{6-30}$ alkyl, $C_{6-30}$ alkenyl or $C_{6-30}$ alkynyl, any of which is unsubstituted or is substituted with F, Cl, OH, SH, methoxy or ethoxy; and $R^2$ is $C_{6-30}$ alkyl, $C_{6-30}$ alkenyl or $C_{6-30}$ alkynyl, any of which is unsubstituted or is substituted with F, Cl, OH, SH, methoxy or ethoxy.

In particularly suitable compounds, $R^1$ is H or unsubstituted $C_{6-30}$ alkyl, unsubstituted $C_{6-30}$ alkenyl or unsubstituted $C_{6-30}$ alkynyl; and $R^2$ is unsubstituted $C_{6-30}$ alkyl, unsubstituted $C_{6-30}$ alkenyl or unsubstituted $C_{6-30}$ alkynyl.

In certain suitable compounds of the invention, wherein $R^1$ is H and $R^2$ is $C_{7-18}$ alkyl, $C_{7-18}$ alkenyl or $C_{7-18}$ alkynyl, any of which is unsubstituted or is substituted with F, Cl, OH, SH, methoxy or ethoxy.

In compounds of this type, it is preferred that $R^1$ is H and $R^2$ is unsubstituted $C_{7-18}$ alkyl, for example heptyl, octyl, decyl, tetradecyl or octadecyl, in particular straight chain $C_{7-18}$ alkyl groups such as n-heptyl, n-octyl, n-nonyl, n-decyl, n-tetradecyl or n-octadecyl and especially n-decyl.

Alternatively, each of $R^1$ and $R^2$ is $C_{7-18}$ alkyl, $C_{7-18}$ alkenyl or $C_{7-18}$ alkynyl, any of which may optionally be substituted as described above.

In compounds of this type, it is preferred that $R^1$ and $R^2$ are each $C_{7-18}$ alkyl, for example heptyl, octyl, decyl, tetradecyl or octadecyl, in particular straight chain $C_{7-18}$ alkyl groups such as n-heptyl, n-octyl, n-nonyl, n-decyl, n-tetradecyl or n-octadecyl and especially n-decyl.

Suitably, each of $R^1$ and $R^2$ is $C_7$-alkyl, $C_8$-alkyl, $C_{10}$ alkyl, $C_{14}$ alkyl or $C_{18}$ alkyl, any of which may be optionally be substituted as described above.

In some cases, at least one of $R^1$ and $R^2$ is unsubstituted.

In some cases, both $R^1$ and $R^2$ are unsubstituted.

In some cases at least one of $R^1$ and $R^2$ is substituted as described above.

In some cases at both $R^1$ and $R^2$ are substituted as described above.

More suitable substituents for $R^1$ and $R^2$ are selected from the group consisting halo, cyano, nitro, azo, diazonium, phosphate, phosphate ester, $NR^3R^4$, $C(O)OR^3$, $OR^3$, $SR^3$, $C(O)SR^3$, $C(O)NR^3R^4$, azide, $C_{6-14}$ aryl or $C_{4-14}$ heteroaryl, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, $OP(O)OR^3OR^4$, —PR³R⁴ and wherein each of R³ and R⁴ is independently H or $C_{1-10}$ alkyl, $C_{2-10}$ alkenyl, $C_{2-10}$ alkynyl.

Alternatively, suitable substituents for R¹ and R² are selected from the group consisting of halo, cyano, nitro, NR³R⁴, C(O)OR³, OR³, SR³, $C_{6-10}$ aryl or heteroaryl, wherein aryl and heteroaryl groups are optionally substituted with one or more substituents selected from $C_{1-4}$ alkyl, $C_{1-4}$ haloalkyl, halo, cyano or nitro; and wherein each of R³ and R⁴ is independently H or $C_{1-6}$ alkyl.

In a further preferred compound R is selected from the group consisting of n-decylamine, octadecylamino, dihexylamino, dioctadecylamino, 3-butenylamino, 5-hexenylamino, oct-3-en-1-amino, tetradec-3-en-1-amino, oleoylamino, ethyl(prop-2-en-1-yl)amino, bis[(2Z)-3-chlorobut-2-en-1-yl]amino, methyl[7-(methylimino)hepta-1,3,5-trien-1-yl]amino, but-3-yn-1-amino, hex-5-ynylamino, oct-3-yn-1-amino, dodec-3-yn-1-amino, 3-fluoro-2-methyloct-7-yn-1-amino, [4,4-dimethyl-2-(pent-4-yn-1-yl)cyclohexyl]methanamino, bis(but-2-yn-1-yl)amino, (dec-1-yn-4-yl)(propyl)amine, N-(2-Naphthyl)-1-naphthylamino, c-(2-p-Tolyl-imidazo[1,2-a]pyridin-3-yl)-methylamino, [2,2-bis(4-chorophenyl)-2-hydroxyethyl]-(2-fluorobenzyl)amino, 4-tetradecylphenylamino, bis[2-(di-tert-butylphosphino)ethyl]amino, h-cys(trt)-nh2,4,10-dibenzyl-1,4,7,10-tetraazacyclododecan-1-yl, 2-(3-oxo-decahydro-quinoxalin-2-yl)-N-(4-phenoxy-phenyl)-acetamide, 2-[(2-amino-4-methylphenyl)sulfanyl]-N-(2-methylphenyl)acetamide, 4-Nitrophenethylamino.

In the present specification, the term "$C_{1-200}$ alkyl" refers to a straight or branched saturated hydrocarbon group having one to 200 carbon atoms. Examples of reagents that could form the NR¹R² structure include: decylamine, octadecylamine, dihexylamine, dioctadecylamine.

In the present specification, the term "$C_{6-30}$ alkyl" refers to a straight or branched saturated hydrocarbon group having six to 30 carbon atoms. Examples of reagents that could form the NR¹R² structure include decylamine, octadecylamine, dihexylamine, dioctadecylamine Other alkyl groups, for example $C_{1-4}$, $C_{1-6}$ and $C_{1-10}$ alkyl are as defined above except that they have different numbers of carbon atoms.

The term "$C_{2-200}$ alkenyl" a straight or branched hydrocarbon chain having from 2 to 200 atoms and at least one carbon-carbon double bond. Alkenyl groups may include more than one carbon-carbon double bond, for example 2, 3, 4, or 5 double bonds. In some cases alkenyl groups may contain more than 5 double bonds.

The term "$C_{6-30}$ alkenyl" a straight or branched hydrocarbon chain having from 6 to 30 atoms and at least one carbon-carbon double bond. Alkenyl groups may include more than one carbon-carbon double bond, for example 2, 3, 4, or 5 double bonds. In some cases alkenyl groups may contain more than 5 double bonds. Examples of reagents that could form the NR¹R² structure include 5-Hexenylamine, oct-3-en-1-amine, tetradec-3-en-1-amine, oleylamine.

Other alkenyl groups, e.g. $C_{2-10}$ alkenyl are as defined for $C_{6-30}$ alkenyl except that they contain different numbers of carbon atoms.

The term "$C_{2-200}$ alkynyl" a straight or branched hydrocarbon chain having from two to 200 carbon atoms and at least one carbon-carbon triple bond. An alkynyl group may contain more than one carbon-carbon triple bond, for example two, three four or five carbon-carbon triple bonds. In some cases alkenyl groups may contain more than 5 triple bonds. In some cases, the alkynyl group may contain one or more carbon-carbon double bond in addition to the one or more carbon-carbon triple bonds.

The term "$C_{6-30}$ alkynyl" a straight or branched hydrocarbon chain having from six to 30 carbon atoms and at least one carbon-carbon triple bond. An alkynyl group may contain more than one carbon-carbon triple bond, for example two, three four or five carbon-carbon triple bonds. In some cases alkenyl groups may contain more than 5 triple bonds. In some cases, the alkynyl group may contain one or more carbon-carbon double bond in addition to the one or more carbon-carbon triple bonds. Examples of reagents that could form the NR¹R² structure include Hex-5-ynylamine, oct-3-yn-1-amine, dodec-3-yn-1-amine, (dec-1-yn-4-yl)(propyl) amine.

Other alkynyl groups, e.g. $C_{2-10}$ alkynyl are as defined for $C_{6-30}$ alkynyl except that they contain different numbers of carbon atoms.

The term "$C_{6-10}$ aryl" in the context of the present specification refer to a ring system with aromatic character having from 6 to 10 ring carbon atoms and containing a single ring or two fused rings. Where an aryl group contains two fused rings, both rings need not be fully aromatic in character. Examples of aromatic moieties are phenyl, naphthalene, tetrahydronaphthalene, indane and indene.

$C_{6-14}$ aryl groups are as defined above but have from 6 to 14 ring carbon atoms. Examples include anthracene and fluorene.

The term "heteroaryl" in the context of the specification refer to a ring system with aromatic character having from 4 to 14 ring atoms at least one of which is a heteroatom selected from, for example, N, O and S, and containing up to three rings. Where a heteroaryl group contains more than one ring, not all rings must be fully aromatic in character. Examples of heteroaryl groups include pyridine, pyrimidine, indole, pyrrole, imidazole, triazole, tetrazole, oxazole, thiazole, benzofuran, benzimidazole and indolene.

Compounds of general formula (I) are prepared by
i) polymerization of aqueous lysine methyl ester.2HCl with an equivalent amount of isophthaloyl chloride in acetone and subsequent hydrolysis in DMSO with ethanolic sodium hydroxide, and
ii) conjugation of R, wherein R comprises NR¹R² and is defined as above onto the polymer backbone via dicyclohexylcarboiimide/dimethylaminopyridine (DCC/DMAP) coupling.

In a further preferred embodiment of the invention said conjugation of R is via 1-Ethyl-3-(3-dimethylaminopropyl)-carbodiimide (EDC)/N-Hydroxysuccinimide (NHS) coupling.

In addition to the chain of general formula (I), compounds of the present invention include end groups X and Y and may be represented by formula (Ia)

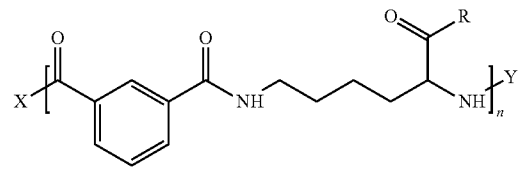

wherein X is OH or a residue of a polymerisation initiator or terminator and Y is H or a residue of a polymerisation initiator or terminator. In some cases, X is OH and Y is H.

The exact nature of the moieties X and Y will depend upon the polymerisation method selected and the initiator and terminator used. Suitable methods are known to those of skill in the art and are described, for example in US2006172418 and Eccleston et al, *Reactive & Functional Polymers*, 42, 147-161 (1999). The content of US2006172418 is hereby incorporated by reference in its entirety.

In a preferred embodiment of the invention said poly(lysine isophthalamide) compound (peptide/peptide analogue-based derivative) is associated, either directly or indirectly with an agent for intracellular delivery to a cell. The agent can be covalently or non-covalently associated with said peptide.

In a preferred embodiment of the invention said covalent association is achieved via amide coupling, disulphide linkage, hydrozone linkage, azide click chemistry or via the use of crosslinkers such as for example a succinimide-maleimide crosslinker.

In some instances, the substituted side-chain ($NR^1R^2$) on the poly(lysine isophthalamide) compound may be conjugated to the agent prior to the linkage reaction to the backbone polymer (e.g. where a carboxylic acid or acid halide is involved, so that no undesired linkages between the agent and polymer backbone, or reactions that result in the side chains linking to a second polymer backbone or looping onto an unreacted carboxyl acid group on the same backbone).

In a preferred embodiment of the invention said non-covalent association is achieved through electrostatic complexation, hydrophobic association, hydrogen bonding, chelation, guest-host interaction, or encapsulation.

Non covalent interactions include, but are not limited to, Ionic or electrostatic interactions wherein a moiety on the agent carrying a +, −, δ+ or δ− charge interacts with a moiety on the peptide according to the invention with the charge, hydrophobic association between hydrophobic drugs/hydrophobic component of the drug with hydrophobic component of the polymer can be utilized for drug loading. Ligands that bind metal ions (e.g. gold-histidine, where the substituted side chain has a histidine-like moiety incorporated) and also Van der Waals' association are included in non-covalent interactions of agents with the peptide according to the invention.

Non-covalent interactions also include biological 'antibody-antigen' interactions (e.g. biotin-streptavidin, wherein either is pre-conjugated to the substituted side chain and the other is conjugated to the agent as herein disclosed) and included within the scope of the disclosure as is the incorporation of single-stranded DNA/RNA which complements a single strand on the nucleic acid agent as herein disclosed.

In a preferred embodiment of the invention said agent is a therapeutic agent.

In a preferred embodiment of the invention said therapeutic agent is a small organic molecule.

In a preferred embodiment of the invention said organic molecule is a chemotherapeutic agent as defined below.

In an alternative preferred embodiment of the invention said small organic molecule is an antibiotic as defined below.

In a further alternative embodiment of the invention said small organic molecule is an antiviral agent as defined below.

In an alternative preferred embodiment of the invention said therapeutic agent is proteinaceous.

In a preferred embodiment of the invention said proteinaceous therapeutic agent is a therapeutic antibody, or an active binding fragment thereof.

In a preferred embodiment of the invention said antibody is a monoclonal antibody.

In a preferred embodiment of the invention said antibody is a chimeric antibody.

In an alternative preferred embodiment of the invention said antibody is a humanized or human antibody.

In an alternative preferred embodiment of the invention said active binding fragment is selected from the group: Fab, $Fab_2$, $F(ab')_2$, Fv, Fc, Fd, single chain antibody fragment.

In a preferred embodiment of the invention said fragment is a single chain antibody fragment.

In an alternative preferred embodiment of the invention said proteinaceous agent is non-antibody pharmaceutical peptide or protein.

In a further alternative preferred embodiment of the invention said therapeutic agent is a nucleic acid.

In a preferred embodiment of the invention said nucleic acid agent comprises an antisense RNA or an antisense oligonucleotide.

In a preferred embodiment of the invention said nucleic acid agent is a small interfering RNA [siRNA].

In a preferred embodiment of the invention said antisense oligonucleotide or siRNA includes modified nucleotides.

In a preferred embodiment of the invention said nucleic acid agent is a miRNA.

In an alternative embodiment of the invention said nucleic acid agent is a vector, preferably an expression vector.

In a preferred embodiment of the invention said vector is selected from the group consisting of: plasmid, phagemid, viral vector or viral based vector.

In an alternative embodiment of the invention said agent is an imaging agent.

In a further preferred embodiment said imaging agent is calcein.

In a preferred embodiment of the invention said agent is a preservation agent, for example a sugar.

"Sugar" includes, for example, monosaccharides, di-saccharides and tri-saccharides.

In a preferred embodiment of the invention sugars are selected from the group consisting of glucose, sucrose, trehalose, mannitol, lactitol, lactulose, lactose, mannobiose, isomaltose, palatinate, sorbitol, raffinose, maltotriose alpha-D-glucopyranosyl-1-6-sorbitol, alpha-D-glucopyranosyl-1-6-mannitol, malto-oligosaccharides and hydrogenated malto-oligosaccharides.

In a preferred embodiment of the invention said preservation agent is trehalose.

A preservation agent extends the life of a cell or a group of cells by minimising oxidative damage or cell membrane disruption through inadequate storage conditions or damage through drying, lyophilization or freezing at sub-zero temperatures. Conventional compounds protecting cells from damage through freezing are glycols such as glycerol or DMSO.

According to a further aspect of the invention there is provided a composition comprising a peptide according to the invention.

In a preferred embodiment of the invention said composition further comprises an agent for intracellular delivery to a cell as herein disclosed.

In a preferred embodiment of the invention the agent is a therapeutic agent and the composition is a pharmaceutical composition including a pharmaceutically acceptable carrier.

When administered the compositions of the present invention are administered in pharmaceutically acceptable preparations. Such preparations may routinely contain pharmaceutically acceptable concentrations of salt, buffering agents, preservatives, compatible carriers and supplementary therapeutic agents' [e.g. anti-cancer agents].

The compositions of the invention can be administered by any conventional route, including oral, rectal, nasal, bronchial (inhaled), transepithelial, topical (including dermal, transdermal, eye drops, buccal and sublingual), vaginal or parenteral (including subcutaneous, intramuscular, intravenous and intradermal) administration and may be prepared by any methods well known in the art of pharmacy.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device. Parenteral formulations will generally be sterile.

In a preferred embodiment of the invention said composition comprises mammalian cells or a collection of mammalian cells.

In a further preferred embodiment said cells are selected from the group consisting of red blood cells, HeLa, CHO, SU-DHL-8, A549, MES-SA, MES-SA/DX5 or hMSC cells, especially HeLA, CHO or A549 cells.

In a further preferred embodiment of the invention said collection of cells is a cellular aggregate, a tissue or an organ, in particular a tissue or an organ.

According to an aspect of the invention there is provided a composition according to the invention for use in the delivery of at least one agent to a mammalian cell, cellular aggregate, tissue or organ, in particular a tissue or an organ.

According to an aspect of the invention there is provided an in vitro or ex vivo method to deliver an agent to a cell comprising:
  i) contacting a cell or a cellular aggregate, tissue or organ comprising cells with an effective amount of a composition according to the invention; and
  ii) incubating said cell, cellular aggregate, tissue or organ to allow permeabilization of said cell or cellular aggregate, tissue or organ comprising cells thereby delivering said agent.

Suitably, the method comprises in step (i) contacting cells or a tissue or organ comprising cells and in step (ii) incubating said cells or tissue or organ comprising cells to allow permeabilization of said cell or tissue or organ comprising cells, thereby delivering said agent.

In a preferred method of the invention said composition comprises one or more agents as herein disclosed.

In an embodiment said cell is a mammalian cell.

In a further embodiment said cell is selected from the group consisting of oocytes, sperm cells, erythrocytes, leukocytes, stem cells and immune cells, especially oocytes, sperm cells, erythrocytes, leukocytes and stem cells.

In a preferred method said step i) is conducted at pH 5.0 to pH 8.0; preferably between pH 6.0-7.1.

In a further preferred method said step i) is conducted between pH 5.0 and 6.0, even more preferably at pH 5.5.

According to a further aspect of the invention there is provided a method to treat a mammalian subject comprising administering a composition according to the invention comprising an effective amount of an agent as herein disclosed.

In a preferred method of the invention said mammalian subject is suffering from a cancer.

According to a further aspect of the invention there is provided the use of a composition according to the invention in the treatment of cancer.

According to a further aspect of the invention there is provided a combined preparation comprising a composition according to the invention and an anticancer agent for use in the treatment of cancer, wherein the composition and the anticancer agent may be administered simultaneously, sequentially or separately.

When administered simultaneously, the composition and the anticancer agent may be administered in a single composition or in separate compositions by different routes.

The invention also provides the use of a composition of the invention and an anticancer agent in the preparation of an agent for the treatment of cancer.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumours, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumours composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

According to a further aspect of the invention there is provided an in vitro or ex vivo method for the preservation of a mammalian cell, cellular aggregate, tissue or organ comprising the steps:
i) providing a preparation comprising a mammalian cell preparation, mammalian cellular aggregate, tissue or organ and a composition according to the invention;
ii) incubating said preparation to permeabilize the mammalian cell membranes of said mammalian cell, cellular aggregate, tissue or organ; and
iii) contacting said permeabilized cell, cellular aggregate, tissue or organ with one or more preservation agents.

Suitably, the method is for the preservation of a mammalian cell, tissue or organ and in step (i) the preparation comprises a mammalian cell preparation or a mammalian tissue or organ and a composition according to the invention; step (ii) comprises incubating said preparation to permeabilize the mammalian cell membranes of the mammalian cell, tissue or organ; and step (iii) comprises contacting the permeabilized cell, tissue or organ with one or more preservation agents.

In a preferred method of the invention said preservation agent is a sugar, for example trehalose, sucrose or maltose. Preferably said preservation agent is trehalose.

In a preferred method said preservation agent is present at a concentration of at least 0.001 M. Preferably, between 0.001M to 1M and even more preferably, between 0.05-0.7M.

In a further preferred method said agent is present at a concentration of at least 0.1 M, suitably 0.1 to 0.7M.

In a preferred method said compound of formula (I) is present at a concentration of at least 1 µg/ml; preferably, 10-5000 µg/ml In a further preferred method said compound of formula (I) is present at a concentration of 50-1000 µg/ml, and preferably 400 µg/ml.

In an alternative method said compound of formula (I) is present at a concentration 5-10000 µg/ml, even more preferably 100-500 ug/ml In a further alternative method said compound of formula (I) is present at a concentration selected from the group consisting of 5, 10, 25, 50, 100, 500, 1000, 2000, 5000 or 10000 µg/ml.

In a further alternative method said compound of formula (I) is present at a concentration of 500 µg/ml.

In a preferred method said cells are incubated with said agent at pH 5.0 to pH 8.0.

In a further preferred method said cells are incubated with said agent at pH 6.0-7.1.

In a preferred method said cells are incubated with said agent for at least 1 min; preferably between 1 min to 24 h and even more preferable between 5 min to 9 h and even more preferably between 5-60 min.

In a preferred method said cells are incubated with said agent for 5 min.

In a further preferred method said cells are incubated with said agent for 10 min.

In a preferred method said cells are incubated between 25-37 degree Celsius.

In a further preferred method said cells are incubated at 37 degree Celsius.

In a further preferred method said cell contain at least 50 mM trehalose; preferably between 100-500 mM, 150-300 mM, and even more preferably between 200-225 mM.

Definitions

Small Organic Molecules

A general definition of "chemotherapeutic agent" is an agent that typically is a small chemical compound that preferably kills cells in particular diseased cells or is at least cytostatic. Agents can be divided with respect to their structure or mode of action. For example, chemotherapeutic agents include alkylating agents, anti-metabolites, anthracyclines, alkaloids, plant terpenoids and toposisomerase inhibitors. Chemotherapeutic agents typically produce their effects on cell division or DNA synthesis. Examples of alkylating agents are is cisplatin, carboplatin or oxaliplatin. Examples of anti-metabolites include purine or pyrimidine analogues. Purine analogues are known in the art. For example thioguanine is used to treat acute leukaemia. Fludarabine inhibits the function of DNA polymerases, DNA primases and DNA ligases and is specific for cell-cycle S-phase. Pentostatin and cladribine are adenosine analogues and are effective against hairy cell leukaemias. A further example is mecrcaptopurine which is an adenine analogue. Pyrimidine analogues are similarly known in the art. For example, 5-fluorouracil (5-FU), floxuridine and cytosine arabinoside. 5-FU has been used for many years in the treatment of breast, colorectal cancer, pancreatic and other cancers. 5-FU can also been formed from the pro-drug capecitabine which is converted to 5-FU in the tumour. Leucovorin, also known as folinic acid, is administered as an adjuvant in cancer chemotherapy and which enhances the inhibitory effects of 5-FU on thymidylate synthase. Alkylating agents are also known in the art and include vinca alkaloids, for example vincristine or vinblastine. Terpenoids have been used for many years and include the taxanes, for example, paclitaxel.

Antibiotics and antiviral agents are effective in the treatment of microbial, for example bacterial and parasitic pathogens and pathogenic viruses. The delivery vehicle according to the invention is particularly well suited to the treatment of intracellular microbial pathogens. For example species of the genus *Mycobacterium, Brucella, Francisella, Legionella* and *Listeria* can exist in an intracellular form. Other bacterial species either are intracellular or are obligate intracellular species, for example species of the genera *Chlamydia, Rickettsia, Salmonella* and *Yersinia*. Viruses are of course obligate intracellular parasites. Parasitic microbial intracellular pathogens include species of the genera Plasmodia, *Toxoplasma, Leishmania* and the trypanosomatid species *Trypanosoma cruzi*. Examples of classes of antibiotics effective in the control of bacterial pathogens include, by example only, penicillins, cephalosporins, rifamycins, sulphonomides, macrolides and tetracyclines. Also included within the scope of the invention are antibacterial peptides such as dermicidins, cecropins and defensins. Antiviral agents include anti-retroviral drugs such as zidovudine, lamivudine, efavrenz and abacavir; and anti-viral drugs such as ganciclovir, aciclovir and oseltamivir. Anti-protozoan agents include lumefantrine, mefloquine, amodiaquine, sulfadoxine, chloroquine used in the treatment of malaria and also combination therapies that use these agents in combination with artemisinin. These are non-limiting examples of agents that can be used with the delivery vehicle according to the invention.

Antibodies

Antibodies include polyclonal and monoclonal antibodies, prepared according to conventional methodology.

Chimeric antibodies are recombinant antibodies in which all of the V-regions of a mouse or rat antibody are combined with human antibody C-regions. Humanized antibodies are recombinant hybrid antibodies which fuse the complementarity determining regions from a rodent antibody V-region with the framework regions from the human antibody V-regions. The C-regions from the human antibody are also used. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanized antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanized antibodies are designed to have less "foreign" antibody regions and are therefore thought to be less immunogenic than chimeric antibodies.

Various fragments of antibodies are known in the art. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A $Fab_2$ fragment comprises two joined Fab fragments. When these two fragments are joined by the immunoglobulin hinge region, a $F(ab')_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety, and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, *Fundamental Immunology* or Janeway et al. *Immunobiology* (cited above). Molecular biology now allows direct synthesis (via expression in cells or chemically) of these fragments, as well as synthesis of combinations thereof. A fragment of an antibody or immunoglobulin can also have bispecific function as described above.

Inhibitory RNA

A technique to specifically ablate gene function which has broad acceptance is through the introduction of double stranded RNA, also referred to as small inhibitory or interfering RNA (siRNA), into a cell which results in the destruction of mRNA complementary to the sequence included in the siRNA molecule. The siRNA molecule comprises two complementary strands of RNA (a sense strand and an antisense strand) annealed to each other to form a double stranded RNA molecule.

The siRNA molecule is typically derived from exons of the gene which is to be ablated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

Modified Nucleic Acid Molecules

The term "modified" as used herein describes a nucleic acid molecule in which;
 i) at least two of its nucleotides are covalently linked via a synthetic internucleoside linkage (i.e., a linkage other than a phosphodiester linkage between the 5' end of one nucleotide and the 3' end of another nucleotide). Alternatively or preferably said linkage may be the 5' end of one nucleotide linked to the 5' end of another nucleotide or the 3' end of one nucleotide with the 3' end of another nucleotide; and/or ii) a chemical group, such as cholesterol, not normally associated with nucleic acids has been covalently attached to the double stranded nucleic acid.

iii) Preferred synthetic internucleoside linkages are phosphorothioates, alkylphosphonates, phosphorodithioates, phosphate esters, alkylphosphonothioates, phosphoramidates, carbamates, phosphate triesters, acetamidates, peptides, and carboxymethyl esters.

The term "modified" also encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include, by example and not by way of limitation, alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5 carboxymethylaminomethyl uracil; dihydrouracil; inosine; N6-isopentyl-adenine; I-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine. Modified double stranded nucleic acids also can include base analogs such as C-5 propyne modified bases (see Wagner et al., Nature Biotechnology 14:840-844, 1996).

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and thereby, inhibits the transcription of that gene and/or the translation of that mRNA. The antisense molecules are designed so as to interfere with transcription or translation of a target gene upon hybridization with the target gene. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. In order to be sufficiently selective and potent for inhibition, such antisense oligonucleotides should comprise at least 7 (Wagner et al., Nature Biotechnology 14:840-844, 1996) and more preferably, at least 15 consecutive bases which are complementary to the target. Most preferably, the antisense oligonucleotides comprise a complementary sequence of 20-30 bases.

Vectors

The use of viruses or "viral vectors" as therapeutic agents is well known in the art. Additionally, a number of viruses are commonly used as vectors for the delivery of exogenous genes. Commonly employed vectors include recombinantly modified enveloped or non-enveloped DNA and RNA viruses, preferably selected from baculoviridiae, parvoviridiae, picomoviridiae, herpesveridiae, poxviridae, adenoviridiae, or picomnaviridiae. Chimeric vectors may also be employed which exploit advantageous elements of each of the parent vector properties (see e.g., Feng, et al. (1997) Nature Biotechnology 15:866-870). Such viral vectors may be wild-type or may be modified by recombinant DNA techniques to be replication deficient, conditionally replicating or replication competent.

Preferred vectors are derived from the adenoviral, adeno-associated viral and retroviral genomes. In the most preferred practice of the invention, the vectors are derived from the human adenovirus genome. Particularly preferred vectors are derived from the human adenovirus serotypes 2 or 5. The replicative capacity of such vectors may be attenuated (to the point of being considered "replication deficient") by modifications or deletions in the E1a and/or E1b coding regions. Other modifications to the viral genome to achieve particular expression characteristics or permit repeat administration or lower immune response are preferred.

Alternatively, the viral vectors may be conditionally replicating or replication competent. Conditionally replicating viral vectors are used to achieve selective expression in particular cell types while avoiding untoward broad spectrum infection. Examples of conditionally replicating vectors are described in Pennisi, E. (1996) Science 274:342-343; Russell, and S. J. (1994) Eur. J. of Cancer 30A(8): 1165-1171. Additional examples of selectively replicating vectors include those vectors wherein a gene essential for replication of the virus is under control of a promoter which is active only in a particular cell type or cell state such that in the absence of expression of such gene, the virus will not replicate. Examples of such vectors are described in Henderson, et al., U.S. Pat. No. 5,698,443; Henderson, et al., U.S. Pat. No. 5,871,726 the entire teachings of which are herein incorporated by reference. It has been demonstrated that viruses which are attenuated for replication are also useful in gene therapy. For example the adenovirus dl1520 containing a specific deletion in the E1b55K gene (Barker and Berk (1987) Virology 156: 107) has been used with therapeutic effect in human beings. Such vectors are also described in McCormick U.S. Pat. Nos. 5,677,178 and 5,846,945.

Certain vectors exhibit a natural tropism for certain tissue types. For example, vectors derived from the genus herpesviridiae have been shown to have preferential infection of neuronal cells. Examples of recombinant modified herpesviridiae vectors are disclosed in U.S. Pat. No. 5,328,688. Cell type specificity or cell type targeting may also be achieved in vectors derived from viruses having characteristically broad infection by the modification of the viral envelope proteins. For example, cell targeting has been achieved with adenovirus vectors by selective modification of the viral genome knob and fibre coding sequences to achieve expression of modified knob and fibre domains having specific interaction with unique cell surface receptors. Other methods of cell specific targeting have been achieved by the conjugation of antibodies or antibody fragments to the envelope proteins (see, e.g. Michael, et al. (1993) J. Biol. Chem 268:6866-6869, Watkins, et al. (1997) Gene Therapy 4:1004-1012; Douglas, et al (1996) Nature Biotechnology 14: 1574-1578. Alternatively, particularly moieties may be conjugated to the viral surface to achieve targeting (see, e.g. Nilson, et al. (1996) Gene Therapy 3:280-286 (conjugation of EGF to retroviral proteins).

Imaging Agent

An "imaging agent" is an agent capable of detection, for example by spectrophotometry, flow cytometry, or microscopy. For example, a label can be attached to the delivery vehicle, thereby permitting detection of the delivery vehicle in vivo. Examples of imaging agents include, but are not limited to, radioactive isotopes, enzyme substrates, co-factors, ligands, chemiluminescent agents, fluorophores, haptens, enzymes, and combinations thereof. Methods for labelling and guidance in the choice of labels appropriate for various purposes are discussed for example in Sambrook et al. (*Molecular Cloning: A Laboratory Manual*, Cold Spring Harbor, N.Y., 1989) and Ausubel et al. (In *Current Protocols in Molecular Biology*, John Wiley & Sons, New York, 1998).

Cells, Tissues, Organs

The invention relates to the treatment, either in vitro or in vivo, of various mammalian cell types, cellular aggregates, tissues comprising mammalian cells and mammalian organs, especially various mammalian cell types, tissues comprising mammalian cells and mammalian organs.

For example mammalian cells, cellular aggregates, tissues or organs (especially mammalian cells, tissues or organs) comprising such cells as a nerve cells, muscle cells (striated, smooth, cardiac); liver cells, a kidney cells, blood cells (e.g. peripheral blood mononuclear cells, erythrocytes, CD4+ lymphocytes, CD8+ lymphocytes, dendritic cells, T regulatory cells, innate lymphoid cells, natural killer cells), pancreatic β cells, epithelial cells, endothelial cell, spermatocytes and oocytes, dermal fibroblasts, fetal fibroblasts, corneal fibroblasts, intestinal mucosa fibroblasts, oral mucosa fibroblasts, oral mucosa keratinocytes and urethral fibroblasts.

In addition to differentiated cells, cellular aggregates, tissues and organs (especially differentiated cells, tissues and organs) the invention anticipates stem cells and lineage restricted stem cells. The term "stem cell" represents a generic group of undifferentiated cells that possess the capacity for self-renewal while retaining varying potentials to form differentiated cells and tissues. Stem cells can be pluripotent or multipotent. A pluripotent stem cell is a cell that has the ability to form all tissues found in an intact organism although the pluripotent stem cell cannot form an intact organism. Furthermore, it is known that human somatic cells can be re-programmed to an undifferentiated state similar to an embryonic stem cell. For example, WO2007/069666 describes re-programming of differentiated cells (e.g. mouse fibroblast cells) without the need to use embryonic stem cells. Nuclear re-programming is achieved by transfection of retroviral vectors into somatic cells that encode nuclear re-programming factors, for example Oct family, Sox family, Klf family and Myc family of transcription factors. The somatic cells de-differentiate and express markers of human embryonic stem cells to produce an "induced pluripotent cell" [iPS]. In Takahashi et al [Cell vol 131, p 861-872, 2007] adult human dermal fibroblasts with the four transcription factors: Oct3/4, Sox2, Klf4, and c-Myc de-differentiate to human ES cells in morphology, proliferation, surface antigens, gene expression, epigenetic status of pluripotent cell-specific genes and telomerase activity.

A multipotent cell has a restricted ability to form differentiated cells and tissues. Typically, adult stem cells are multipotent stem cells and are the precursor stem cells or lineage restricted stem cells that have the ability to form some cells or tissues and replenish senescing or damaged cells/tissues. Generally they cannot form al tissues found in an organism, although some reports have claimed a greater potential for such 'adult' stem cells than originally thought. Examples of multipotent stem cells include mesenchymal stem cells. Mesenchymal stem cells differentiate into a variety of cell types that include osteoblasts, chondrocytes, myocytes, adipocytes and neurones. Typically, mesenchymal stem cells are obtained from bone marrow. Currently, stem cell therapies are exploring different sources of pluripotent and multipotent stem cells and cell culture conditions to efficiently differentiate stem cells into cells and tissues suitable for use in tissue repair.

Stem cells such as haemopoietic stem cells, neural stem cells, bone stem cells, muscle stem cells, mesenchymal stem cells, trophoblastic stem cells, epithelial stem cells (derived from organs such as the skin, gastrointestinal mucosa, kidney, bladder, mammary glands, uterus, prostate and endocrine glands such as the pituitary), endodermal stem cells (derived from organs such as the liver, pancreas, lung and blood vessels); embryonic stem (ES) cells; embryonal germ (EG) cells.

Conjugation of Hydrophobic Chains to the Amphiphilic Peptide or Peptide Analogue Hydrophobic pendant chains can be attached to the amphiphilic polymer backbone via DCC/DMAP coupling, or via 1-Ethyl-3-(3-dimethylaminopropyl)-carbodiimide (EDC)/N-Hydroxysuccinimide (NHS) coupling. Hydrophobic chains comprising COOH can be conjugated onto PLP via the crosslinker N-Boc-cadaverine (Sigma) (*Advanced Functional Materials* 2013, 23, 565-574) and DCC/DMAP coupling. Similarly, thiol-containing hydrophobic chains (or agents) can be conjugated onto the polycarbonate via a cleavable disulfide bond crosslinker (e.g. pyridyldithiol-and-hydrazide crosslinker) (Thermo Fisher Scientific). The amine group of a pyridyldithiol-and-hydrazide crosslinker such as PDPH (3-(2-pyridyldithio)propionyl hydrazine) can be coupled with COOH via DCC/DMAP coupling and through PDPH thiol-containing hydrophobic chains (or agents) can be conjugated onto the polymer. Also, alkyne-containing hydrophobic chains (or agents), or those functionalised with an alkyne group, can be conjugated onto the polycarbonate via click chemistry using the crosslinker, e.g. amine-PEG-azide (Sigma). The amine group of the amine-PEG-azide can be coupled with COOH via and DCC/DMAP coupling and through click chemistry hydrophobic chains (or agents) can be conjugated onto the polymer. Alternatively, the polymer can be functionalised by amine-containing alkyne and the hydrophobic chains (or agents) can be functionalised with azide. Amine-containing hydrophobic chains (or agents) can be directly conjugated onto the polycarbonate via amide coupling chemistry described in the materials and methods of the patent. Primary amine terminated pluronic derivatives can be synthesised according to the method described by Harris et al ( ) for the modification of polyethylene oxides (Journal of Polymer Science: Polymer Chemistry Edition 1984, 22, 341-352).

Throughout the description and claims of this specification, the words "comprise" and "contain" and variations of the words, for example "comprising" and "comprises", means "including but not limited to", and is not intended to (and does not) exclude other moieties, additives, ents, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Figure 2:
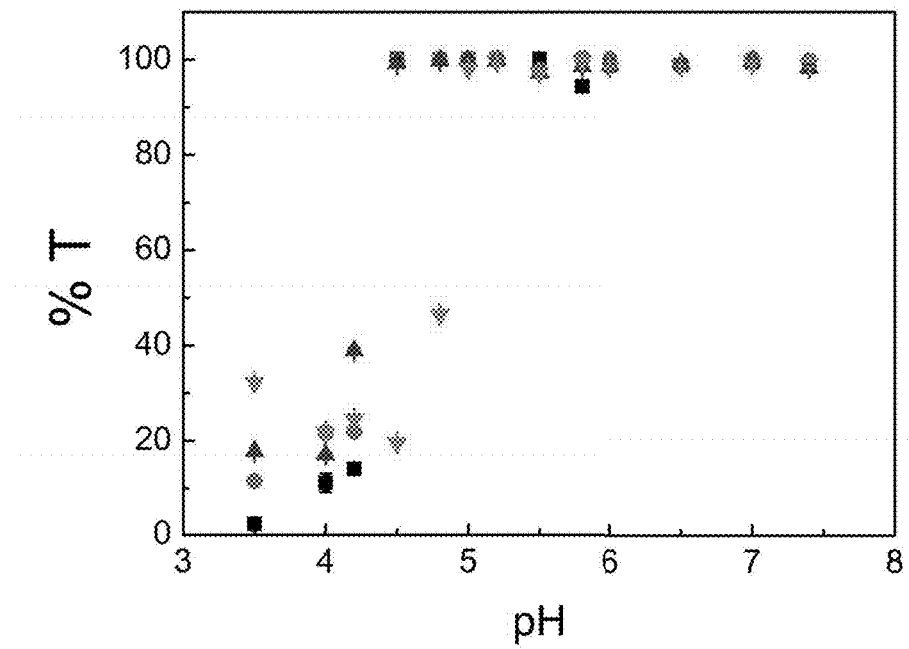
Figure 2:
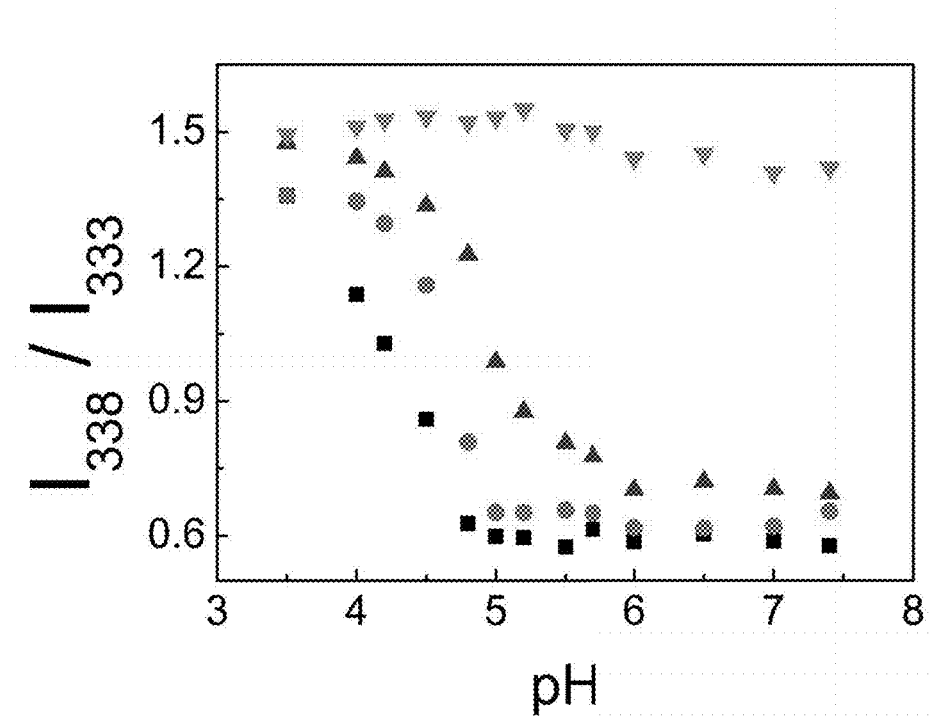
Figure 2:
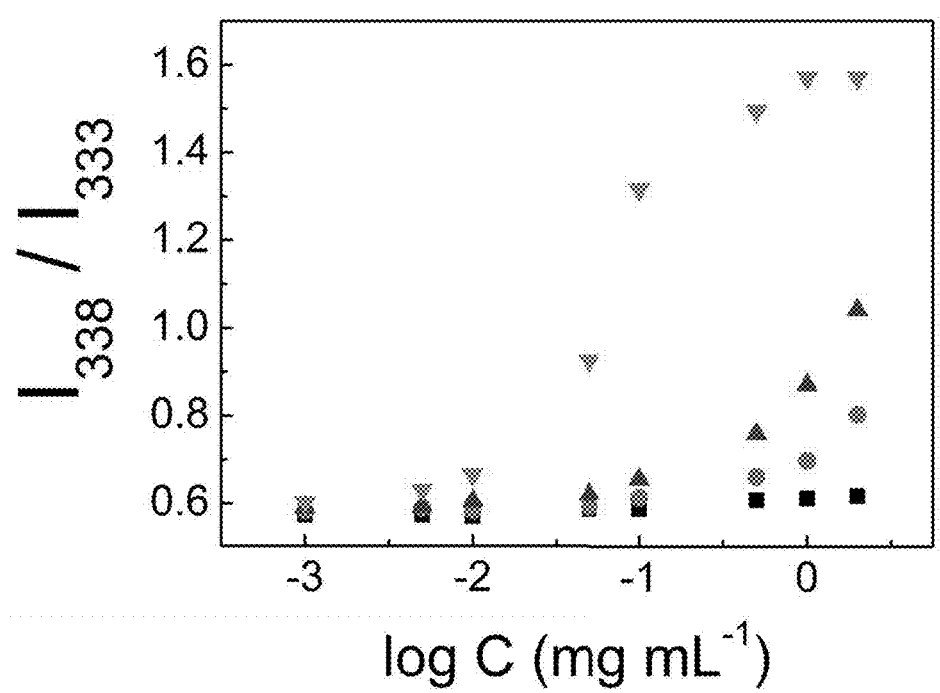
Figure 5:
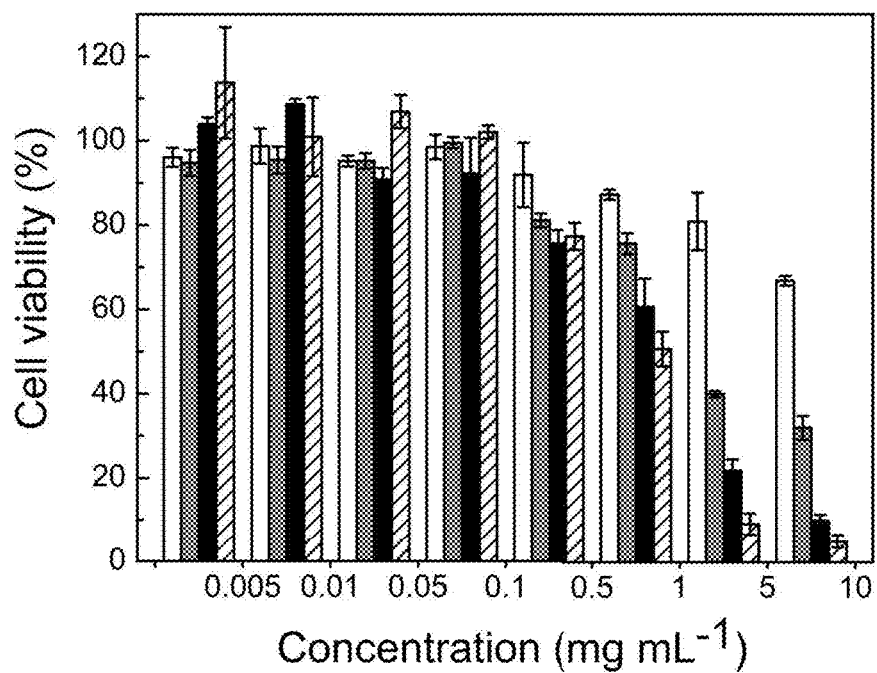
Figure 5:
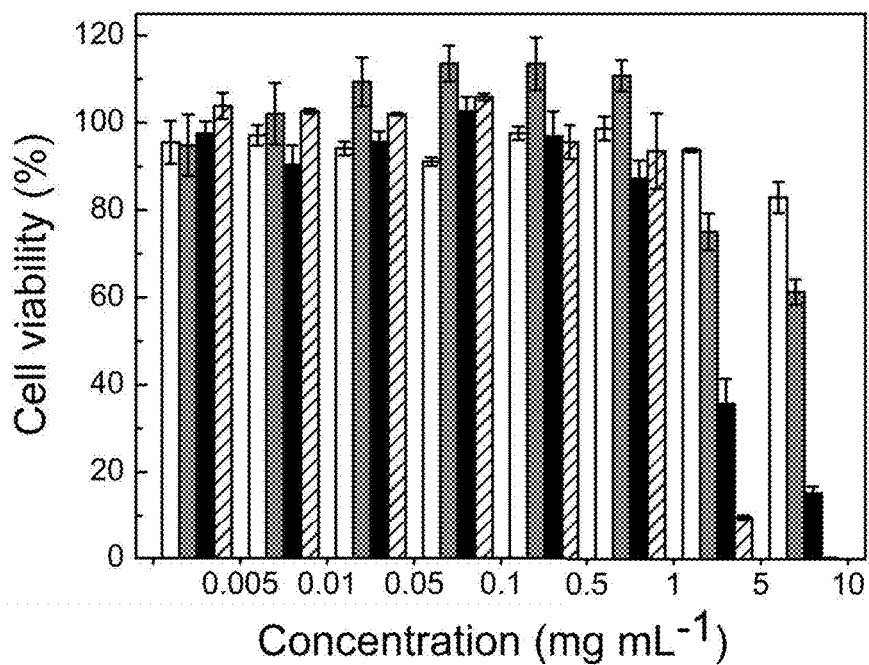
Figure 5:
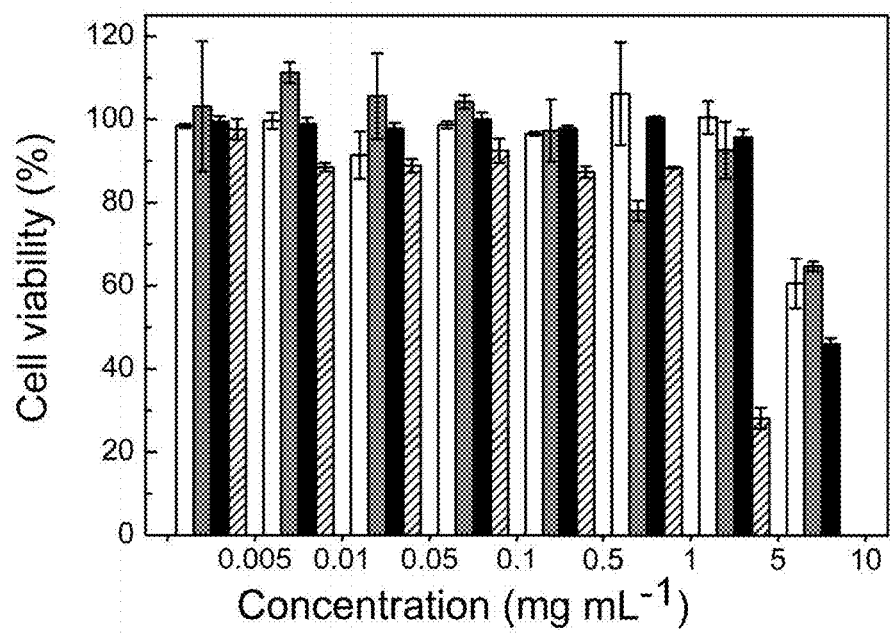
Figure 5:
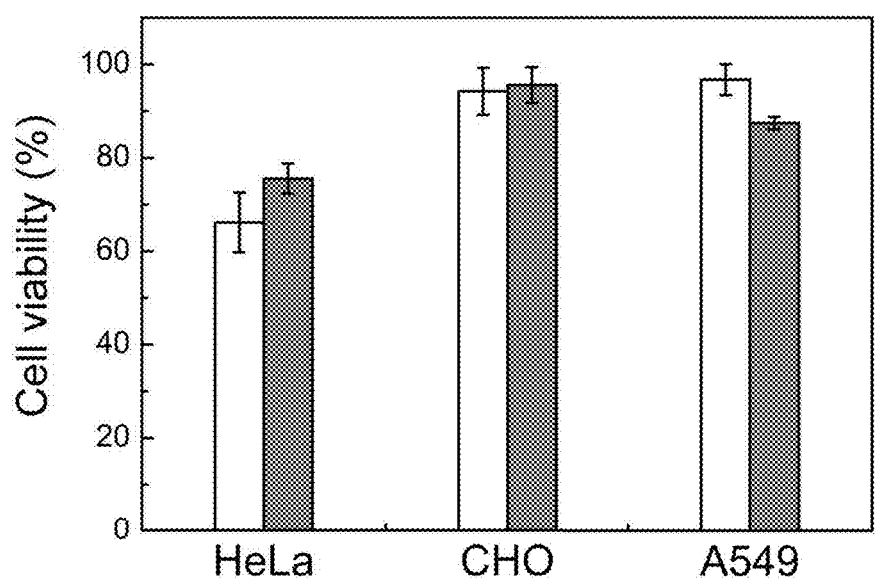
Figure 6:
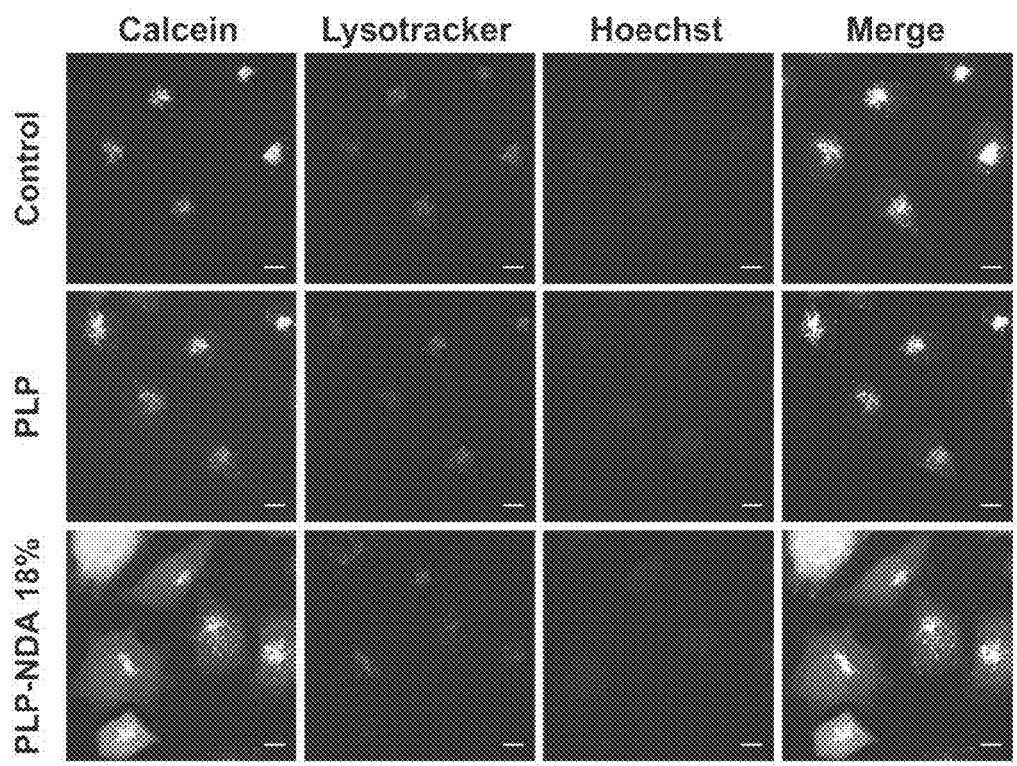
Figure 6:
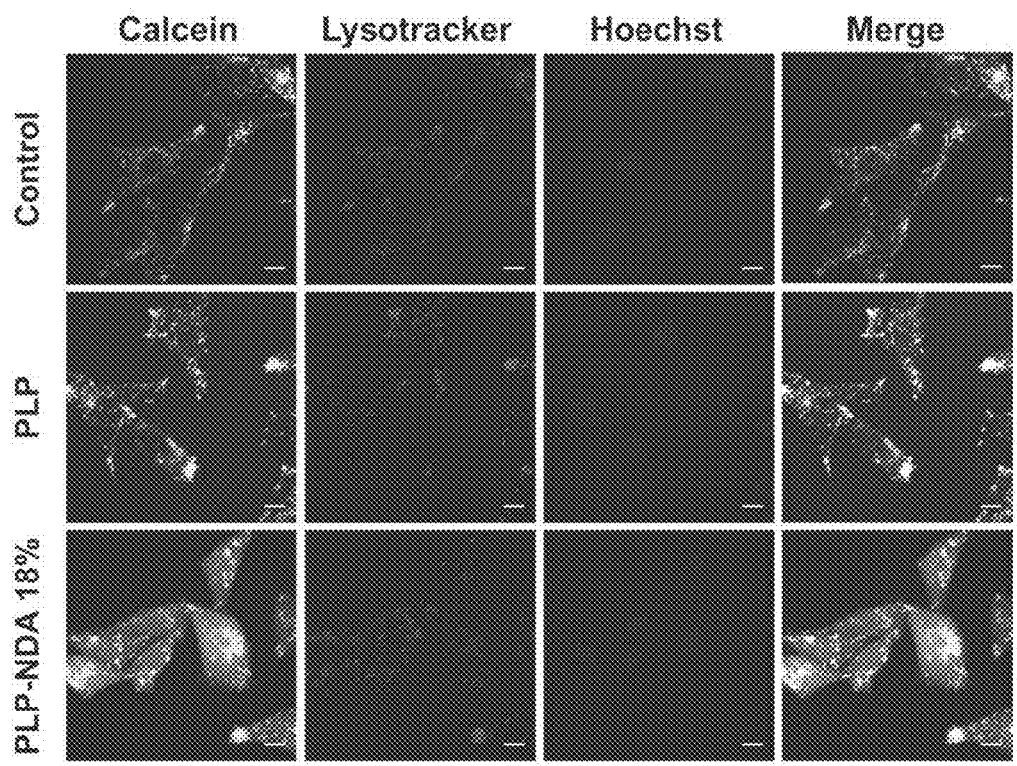
Figure 6:
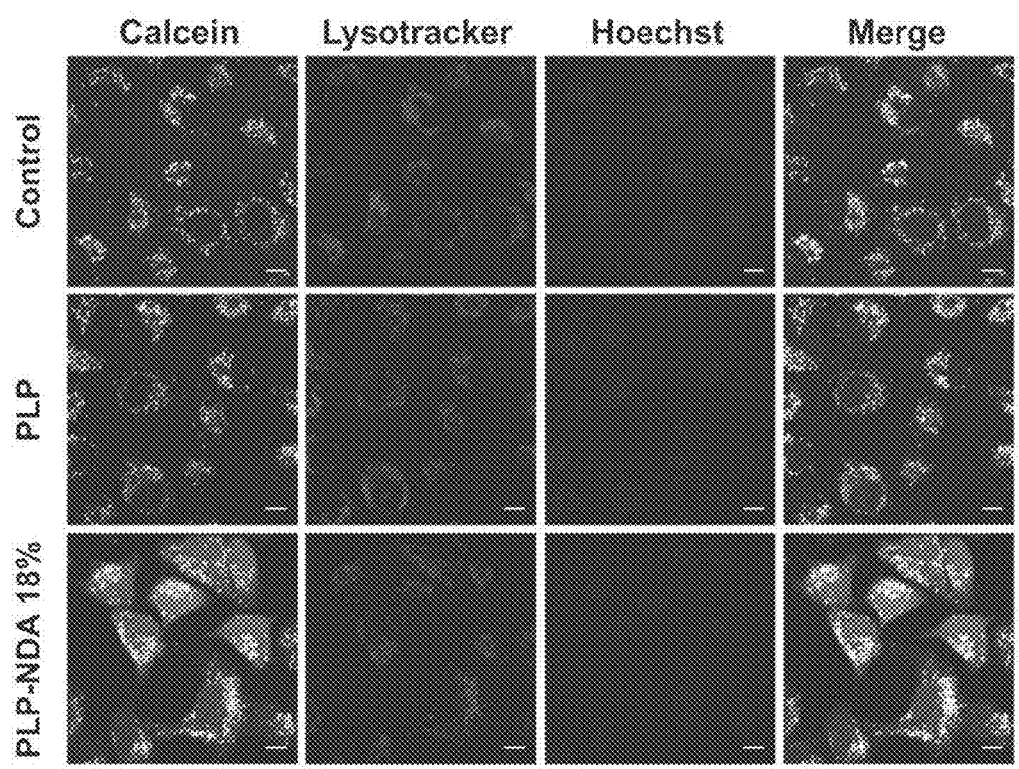
Figure 7:
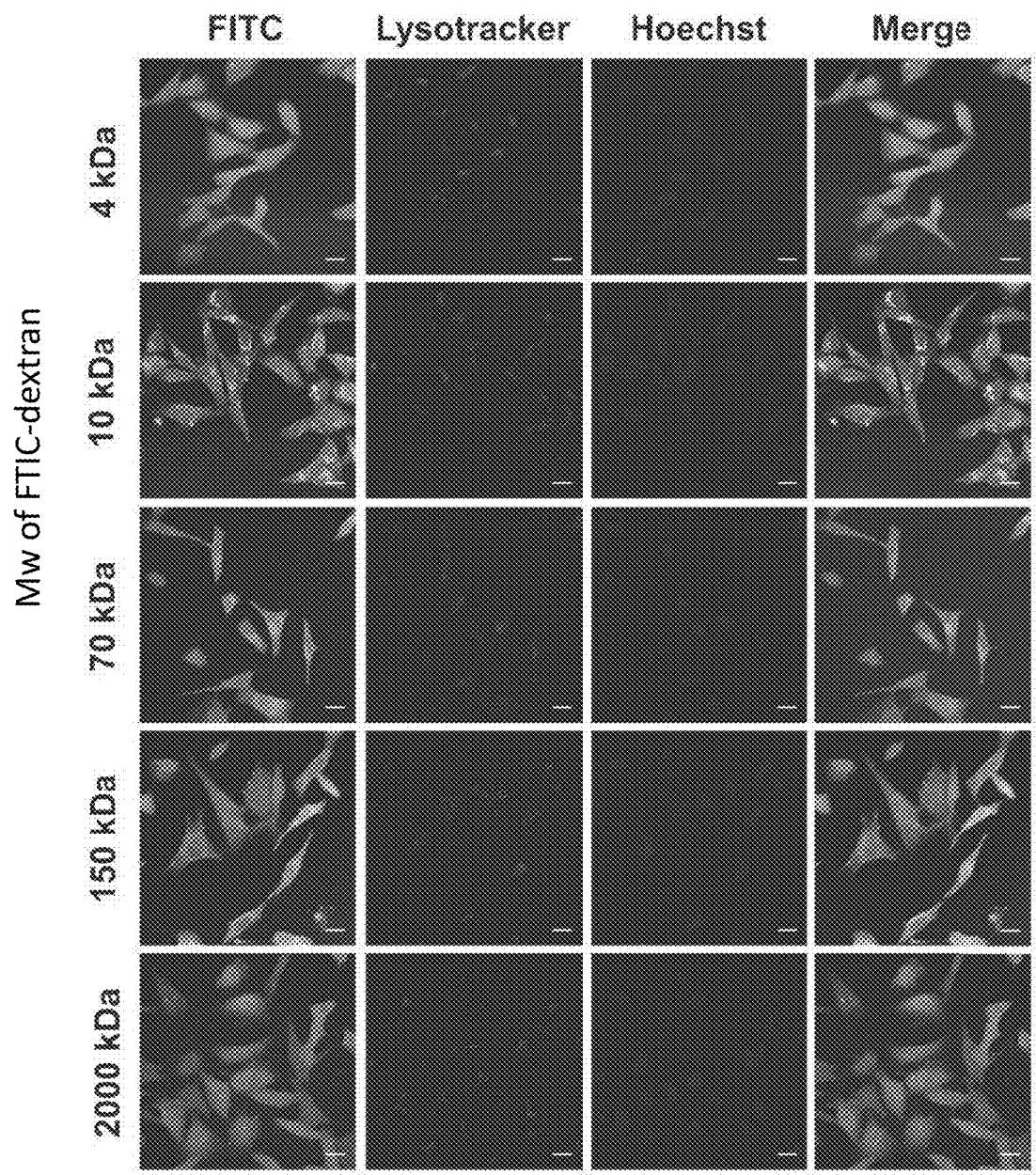
Figure 7:
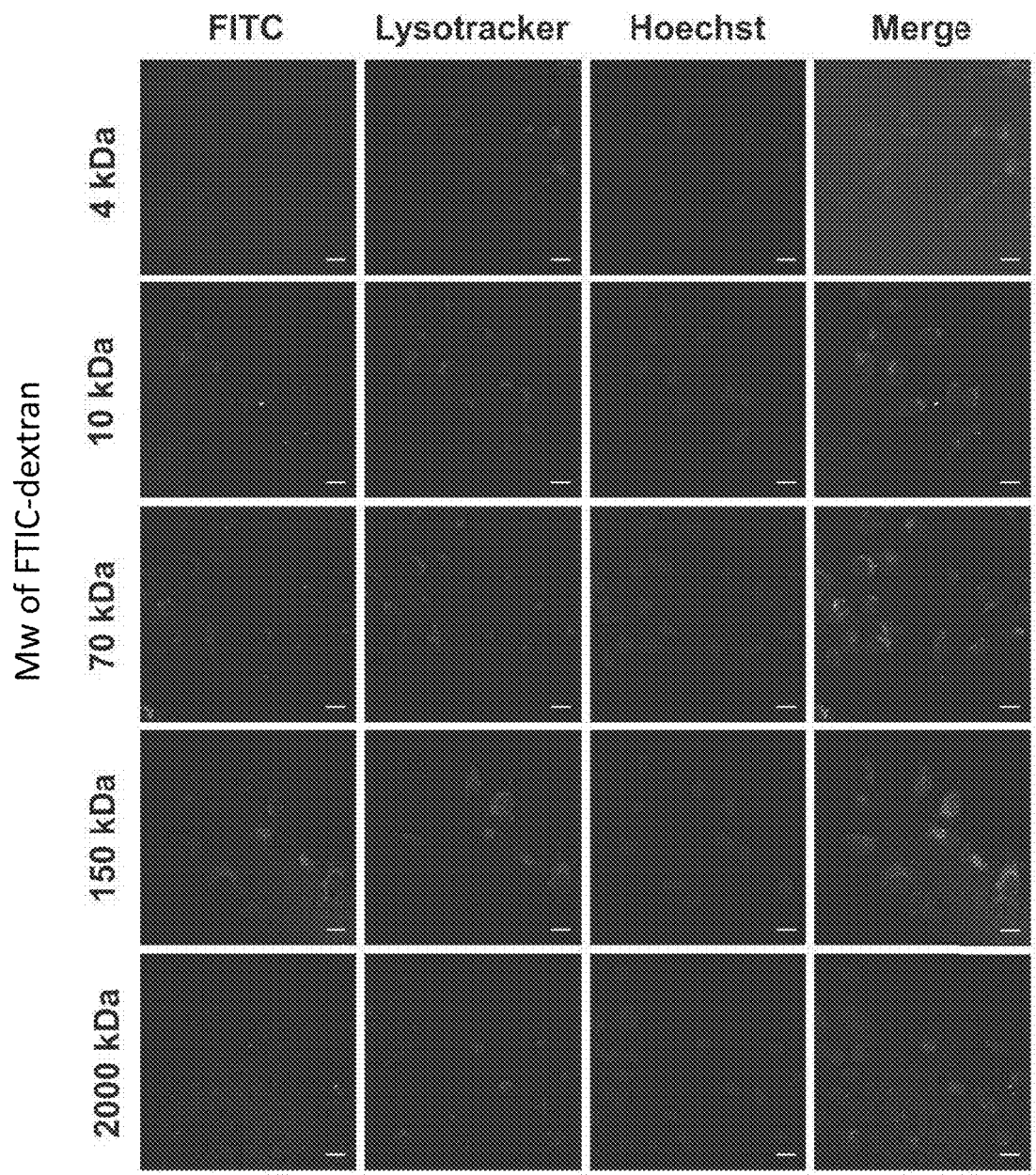
Figure 7:
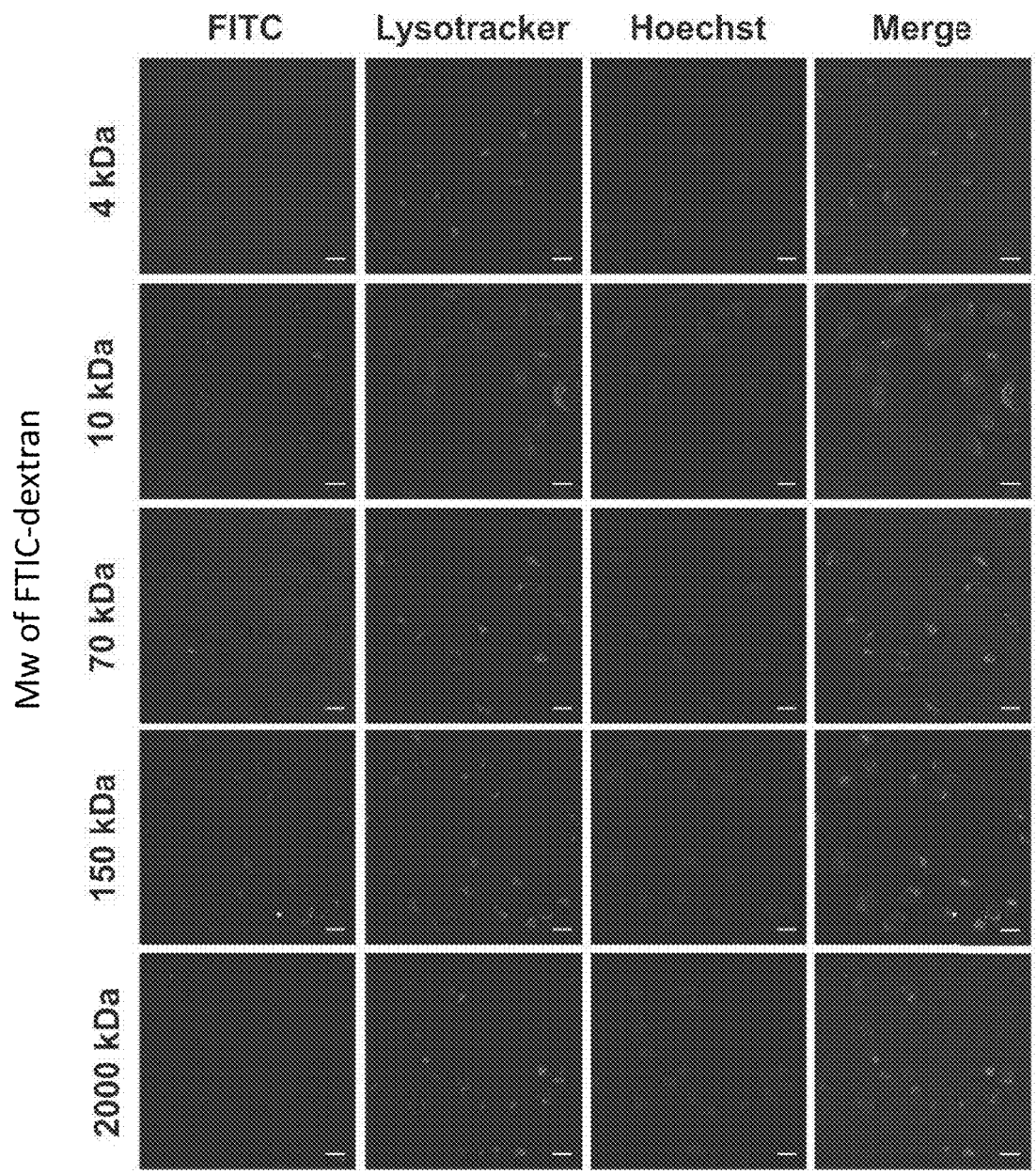
Figure 8:
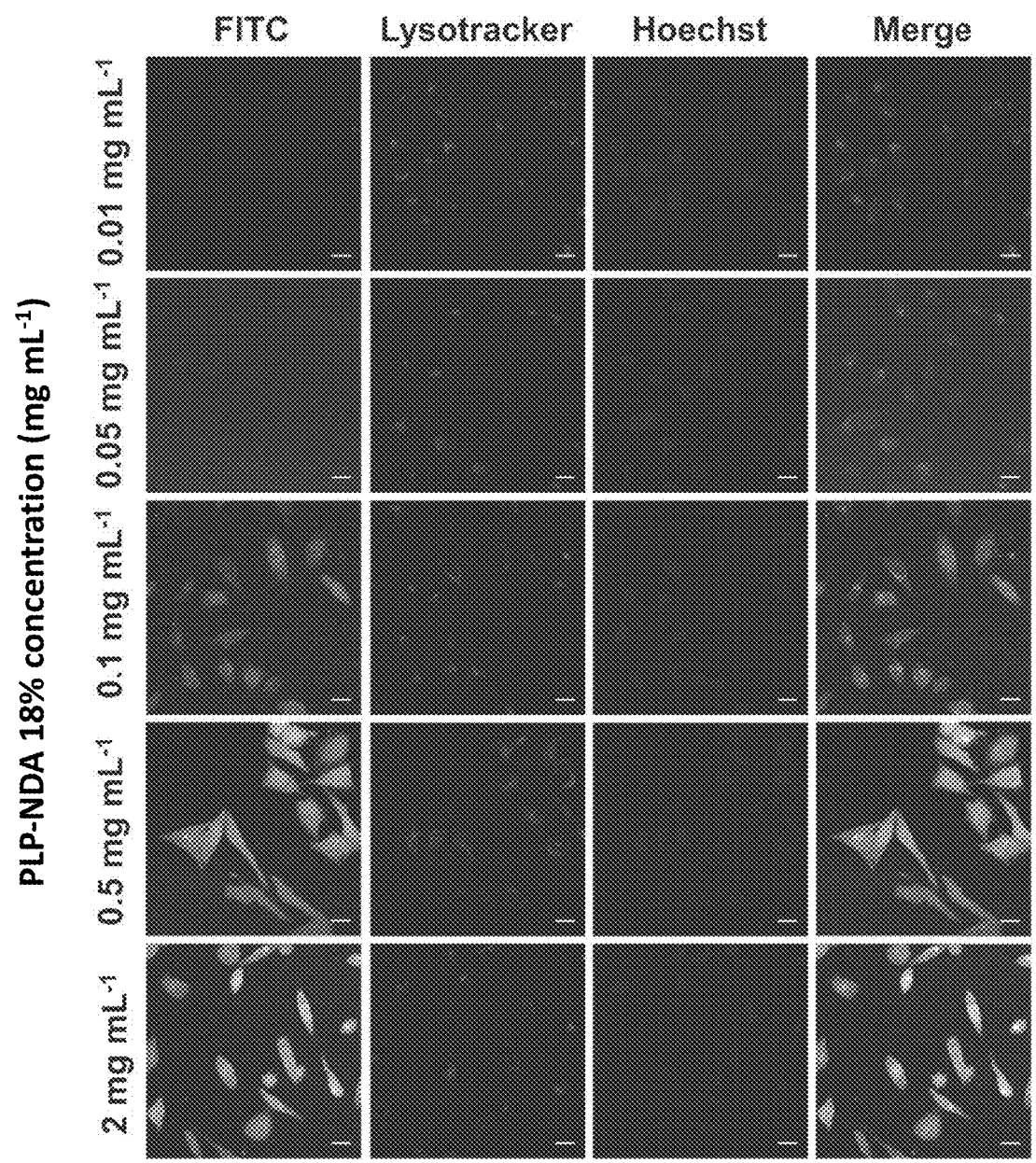

An embodiment of the invention will now be described by example only and with reference to the following figures:

FIGS. 1(A)-(B): FIG. 1(A) 1H-NMR spectra of PLP grafted with NDA in acid form in de-DMSO at room temperature. FIG. 1(B) FTIR spectra of PLP grafted with NDA in acid form. In addition to NDA (C10), other pendant chains including HDA (C7), TDA (C14) and ODA (C18) have also been conjugated to the pseudo-peptide backbone;

FIGS. 2(A)-(C): FIG. 2(A) pH dependent transmittance of the aqueous solutions of PLP (■), PLP-NDA 3% (●), PLP-NDA 10% (▲) and PLP-NDA 18% (▼) at 1.0 mg mL$^{-1}$ in 100 mM buffers. FIG. 2(B) pH dependent change of $I_{338}/I_{333}$ in the excitation spectra of pyrene dissolved in aqueous solutions of PLP (■), PLP-NDA 3% (●), PLP-NDA 10% (▲), PLP-NDA 18% (▼) at 0.5 mg mL$^{-1}$. FIG. 2(C) Concentration dependent change of $I_{338}/I_{333}$ in the excitation spectra of pyrene dissolved in aqueous solutions of PLP (■), PLP-NDA 3% (●), PLP-NDA 10% (▲), PLP-NDA 18% (▼) at pH 7.4;

FIGS. 3(A)-(B): Particle size distributions of FIG. 3(A) PLP and FIG. 3(B) PLP-NDA 18% at the concentration of 0.5 mg mL$^{-1}$ at pH 7.4 (solid) and pH 5.5 (dash);

FIGS. 4(A)-(C): Relative haemolysis of red blood cells with the present of PLP and its derivatives. FIG. 4(A) pH dependent haemolysis of RBC incubated with PLP (■), PLP-NDA 3% (●), PLP-NDA 10% (▲), PLP-NDA 18% (▼) at 0.5 mg mL$^{-1}$ for 1 h. FIG. 4(B) Concentration dependent haemolysis of RBC incubated with PLP-NDA 18% at pH 7.4 (open column) and pH 5.5 (closed column). FIG. 4(C) Time dependent haemolysis of RBC incubated with PLP (■), PLP-NDA 3% (●), PLP-NDA 10% (▲), PLP-NDA 18% (▼) at 0.5 mg mL$^{-1}$ at pH 5.5;

FIGS. 5(A)-(D): In-vitro cytotoxicity. Viability of FIG. 5(A) HeLa cells, FIG. 5(B) CHO cells and FIG. 5(C) A549 cells incubated with PL-NDA 18% at various concentrations for 4 h (blank), 12 h (grey), 24 h (black) and 48 h (stripped). FIG. 5(D) In-vitro cytotoxicity of PLP (blank) and PLP-NDA 18% (grey) against HeLa, CHO and A549 cells at polymer concentration of 0.5 mg mL$^{-1}$ for 24 h;

FIGS. 6(A)-(C): Confocal microscopy images of FIG. 6(A) Hela cells. FIG. 6(B) CHO cells and FIG. 6(C) A549 cells showing the subcellular distribution of calcein fluorescence. The cells were treated with 2.0 mg mL$^{-1}$ calcein alone, both 2.0 mg mL$^{-1}$ calcein and 0.5 mg mL$^{-1}$ PLP, or both 2.0 mg mL$^{-1}$ calcein and 0.5 mg mL$^{-1}$ PLP-NDA 18% respectively. Images of HeLa and CHO cells were acquired after 1 h of uptake and further incubated for 3 h. For A549 cells, the uptake was 2 h and the further incubation was 2 h. Scale bar: 10 μm;

FIGS. 7(A)-(C): PLP-NDA 18% mediated delivery of FITC-dextran with different molecular weights into HeLa cells. FIG. 7(A) HeLa cells incubated with 0.5 mg mL$^{-1}$ PLP-NDA 18% and FITC-dextran at pH 6.5 for 30 min. FIG. 7(B) HeLa cells incubated with FITC-dextran only at pH 6.5 for 30 min. FIG. 7(C) HeLa cells incubated with 0.5 mg mL$^{-1}$ PLP-NDA 18% and FITC-dextran at pH 7.4 for 30 min. Scale bar: 20 μm;

FIG. 8: Polymer concentration-dependent intracellular delivery. HeLa cells were incubated with PLP-NDA 18% at various concentrations and 200 μM FITC-dextran (4 kDa) at pH 6.5 for 30 min. Scale bar: 20 μm.

FIGS. 9(A)-(B): FIG. 9(A) Confocal microscopy images and FIG. 9(B) relative mean fluorescence intensity (MFI) of the polymer-mediated delivery analyzed by flow cytometry. HeLa cells were incubated with 200 μM FITC-dextran (4 kDa) in the absence (control) or in the presence of 0.5 mg mL$^{-1}$ comb-like polymers containing alkyl chains with different lengths at pH 6.5 for 30 min. Scale bar: 20 μm. Mean±S.D. (n=3).

Figure 10:
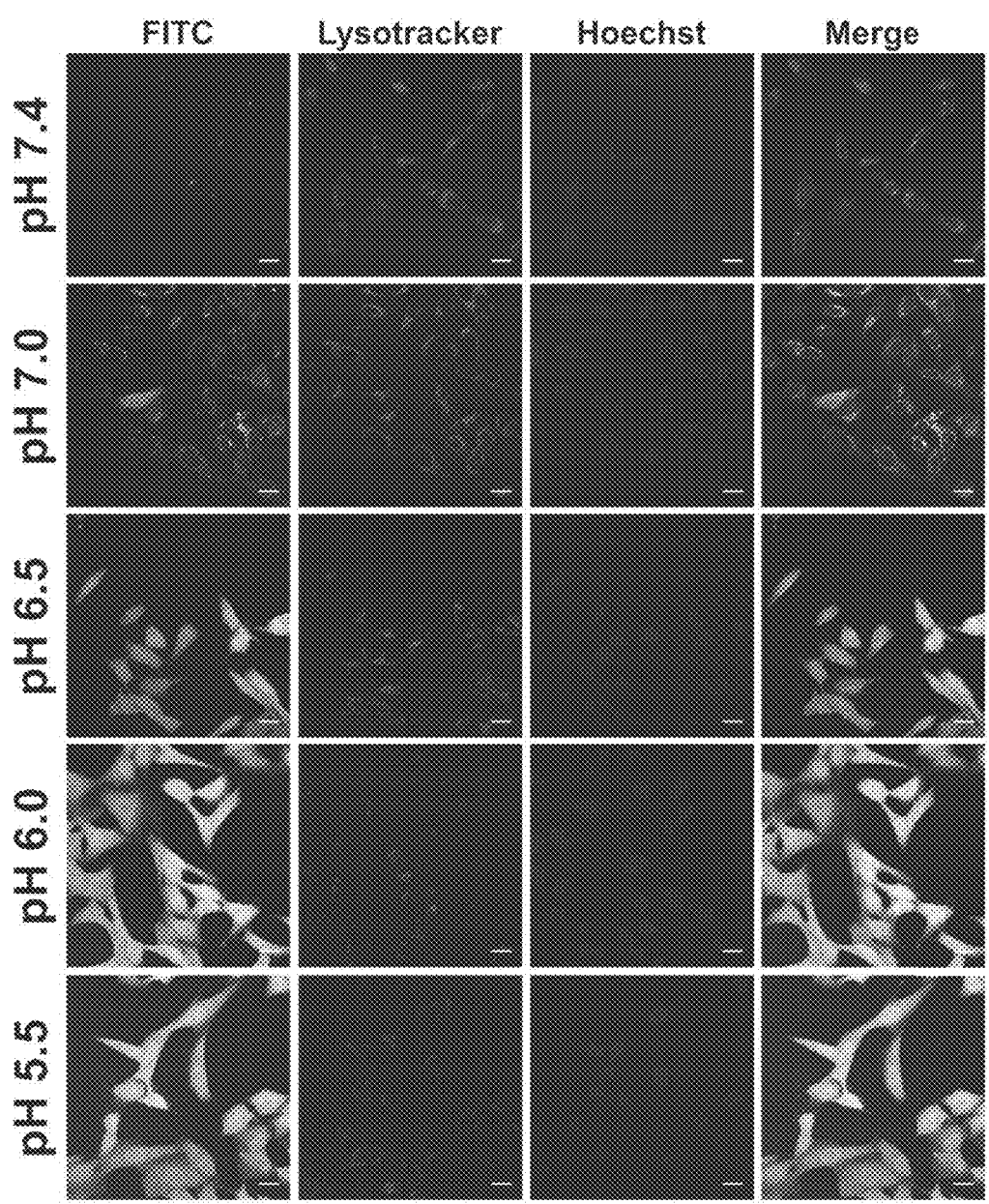

FIG. 10. Confocal microscopy images of pH-dependent polymer-mediated intracellular delivery. HeLa cells were co-incubated with 0.5 mg mL$^{-1}$ PLP-NDA 18% and 200 μM FITC-dextran (4 kDa) at various extracellular pHs for 30 min. Scale bar: 20 μm.

FIGS. 11(A)-(B). FIG. 11(A) Relative MFI and FIG. 11(B) representative histogram plots of the polymer-mediated delivery of 200 μM FITC-dextran (4 kDa) at different extracellular pHs analyzed by flow cytometry. HeLa cells were incubated in the absence (open columns) or in the presence of PLP-NDA 18% at 0.5 mg mL$^{-1}$ (dose columns) at different extracellular pHs for 30 min. Mean±S.D. (n=3).

Figure 12:
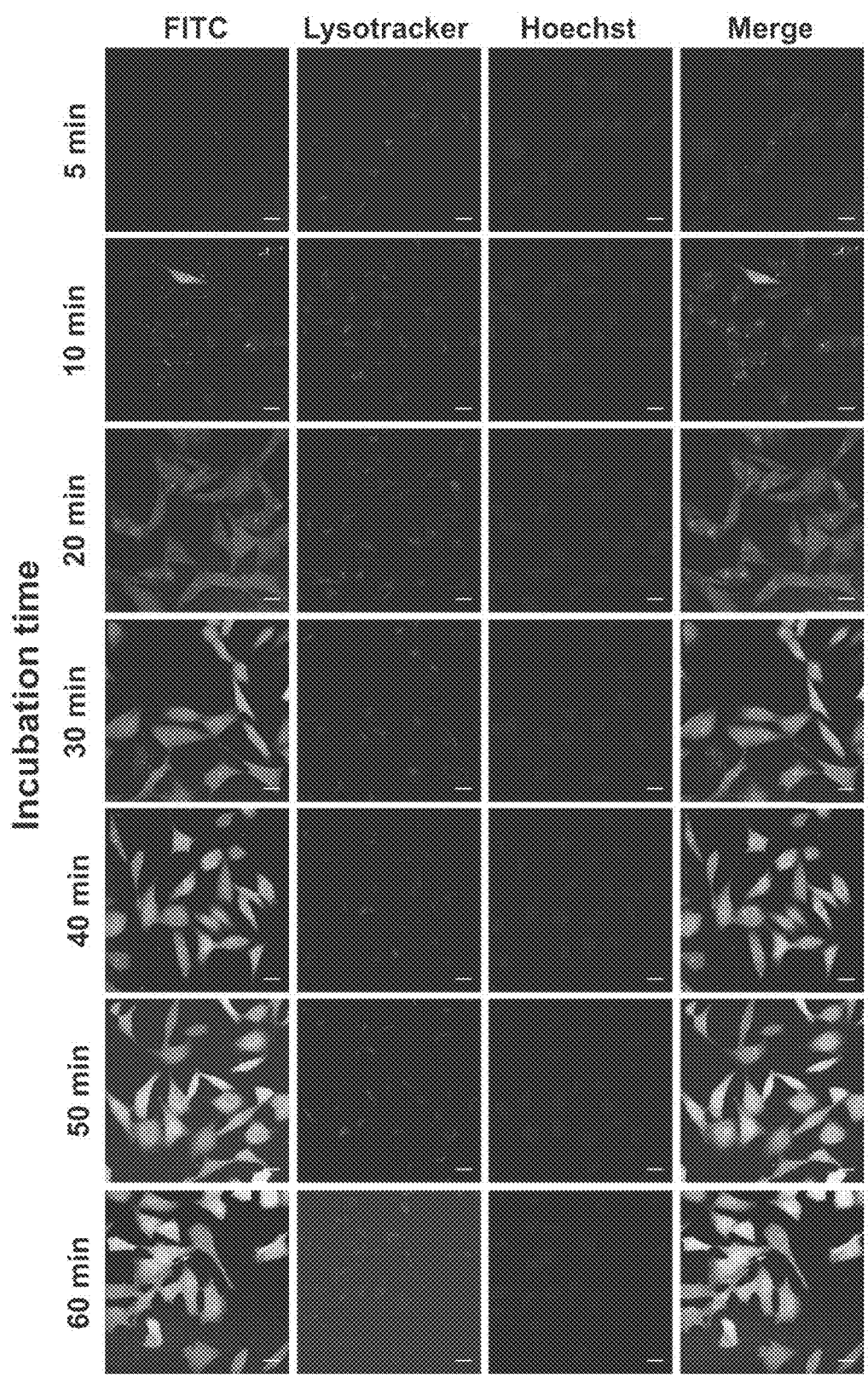

FIG. 12. Confocal microscopy images of time-dependent polymer-mediated intracellular delivery. HeLa cells were co-incubated with 0.5 mg mL$^{-1}$ PLP-NDA 18% and 200 μM FITC-dextran (4 kDa) at pH 6.5 for various time periods. Scale bar: 20 μm.

Figure 13:
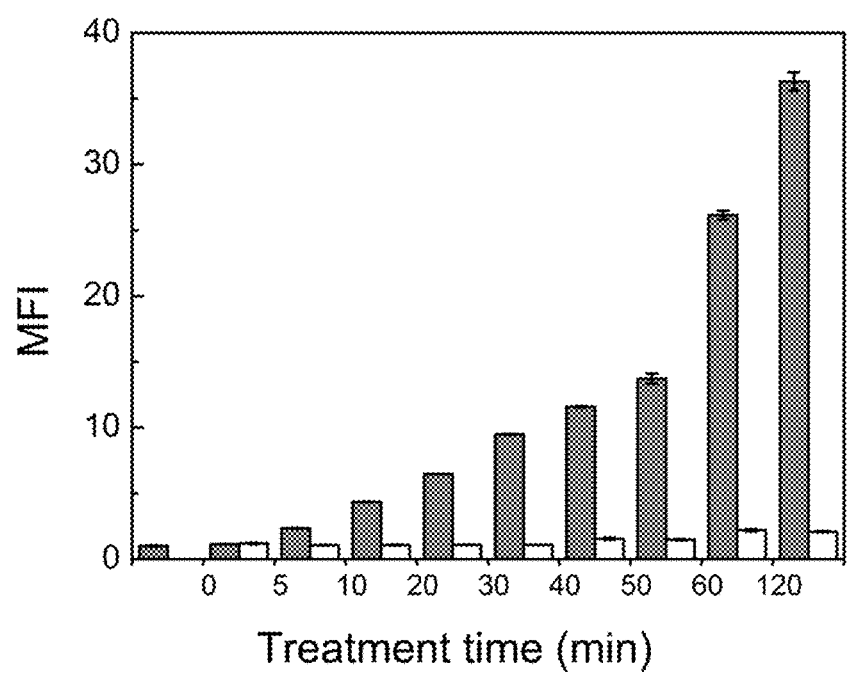

FIG. 13. Relative MFI of time-dependent polymer-mediated intracellular delivery analyzed by flow cytometry. HeLa cells were incubated with 200 μM FITC-dextran (4 kDa) in the absence (open columns) or in the presence of 0.5 mg mL$^{-1}$ PLP-NDA 18% (close columns) at pH 6.5 for various time periods. Mean±S.D. (n=3).

Figure 14:
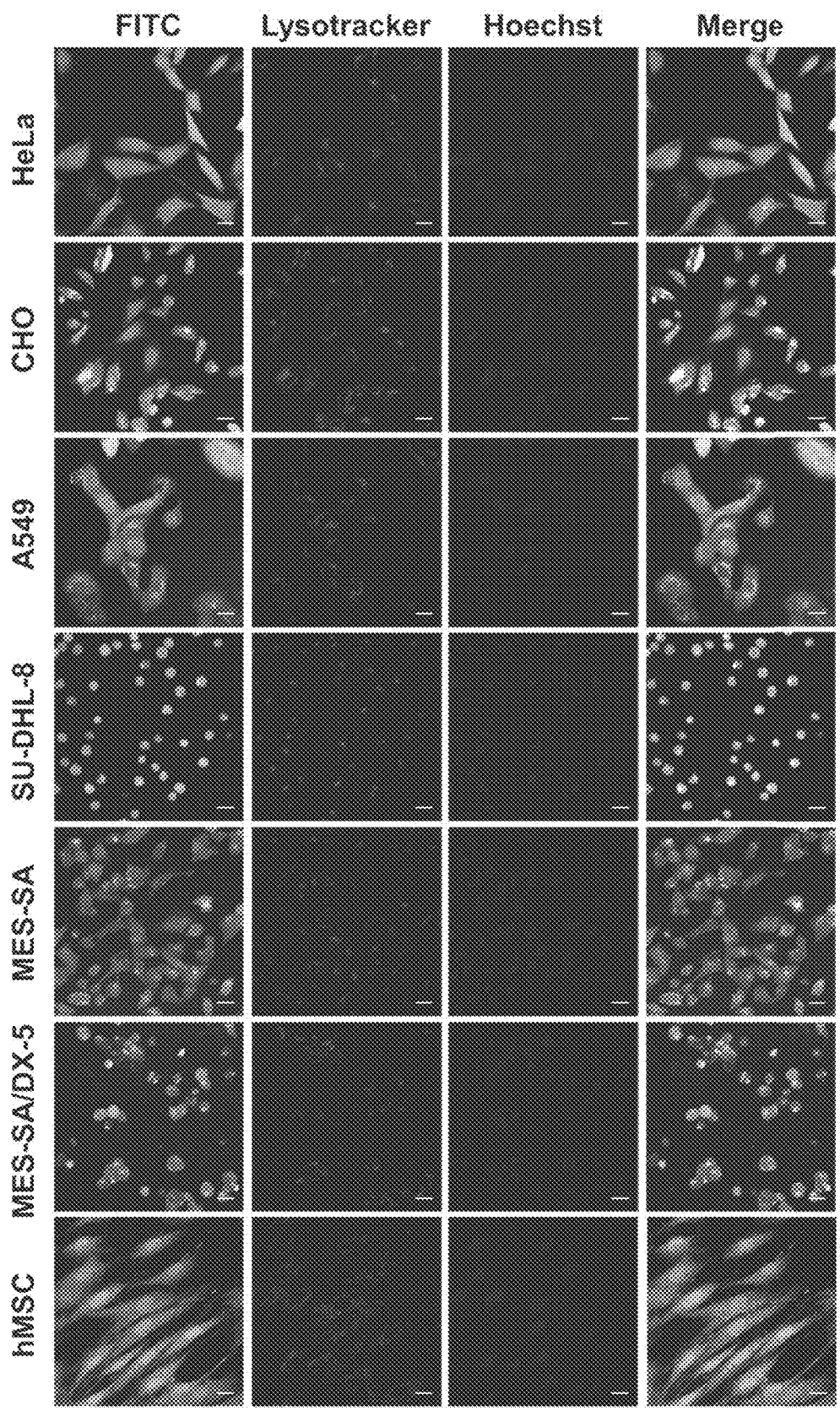

FIG. 14. Confocal microscopy images of polymer-mediated delivery of FITC-dextran (4 kDa) into difference cell types. All the cells were co-treated with 0.5 mg mL$^{-1}$ PLP-NDA 18% and 200 μM FITC-dextran at pH 6.5. The treatment time was 30 min for HeLa, CHO and SU-DHL-8 cells, 180 min for A549 cells, and 60 min for MES-SA, MES-SA/DX5 and hMSCs. Scale bar: 20 μm.

FIGS. 15(A)-(B). FIG. 15(A) Relative MFI and FIG. 15(B) representative histogram plots showing the polymer-mediated delivery of FITC-dextran into difference cell types. All the cells were treated with 0.5 mg mL$^{-1}$ PLP-NDA 18% and 200 μM FITC-dextran (4 kDa) at pH 6.5. The treatment time was 30 min for HeLa, CHO and SU-DHL-8 cells, 180 min for A549 cells, and 50 min for MES-SA, MES-SA/DX5 and hMSC cells. Mean±S.D. (n=3).

FIGS. 16(A)-(C). FIG. 16(A) Polymer concentration-dependent in vitro cytotoxicity. HeLa cells were treated with PLP-NDA 18% at various concentrations at pH 6.5 (close columns) and pH 7.4 (open columns) for 1 h. FIG. 16(B) Time-dependent in vitro cytotoxicity. HeLa cells were treated with PLP-NDA 18% at 0.5 mg mL$^{-1}$ at pH 6.5 (close columns) and pH 7.4 (open columns) for various time periods. FIG. 16(C) In vitro cytotoxicity of PLP-NDA 18% toward a variety of cell lines. HeLa, A549, CHO, MES-SA, MES-SA/DX5, and hMSCs were treated with PLP-NDA 18% at 0.5 mg mL$^{-1}$ at pH 6.5 (close columns) and pH 7.4 (open columns) for 3 h. Mean±S.D. (n=3).

Figure 17:
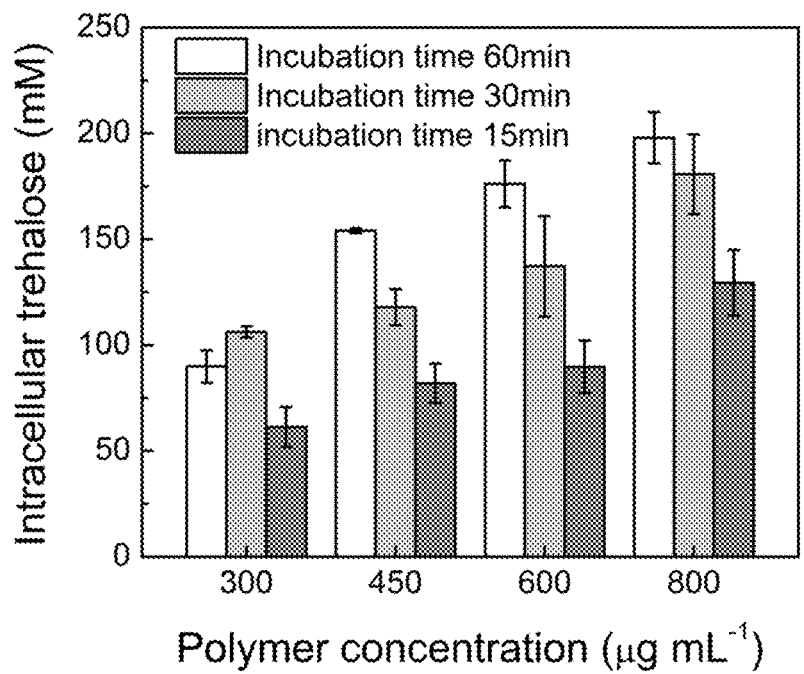

FIG. 17: Trehalose loading of erythrocytes (packed volume of 15%, 3.5×10$^9$ cells per mL) in 0.36 M trehalose solution and with addition of different concentrations of PLP-NDA 18%. [PLP-NDA 18%]=300, 450, 600 and 800 µg mL$^{-1}$; incubation time=15 min, 30 min and 1 h; temperature=37° C. and pH=7.05. The intracellular trehalose concentration was calculated by the anthrone method. Data were derived from three replicates. Error bars represent standard deviations.

Figure 18:
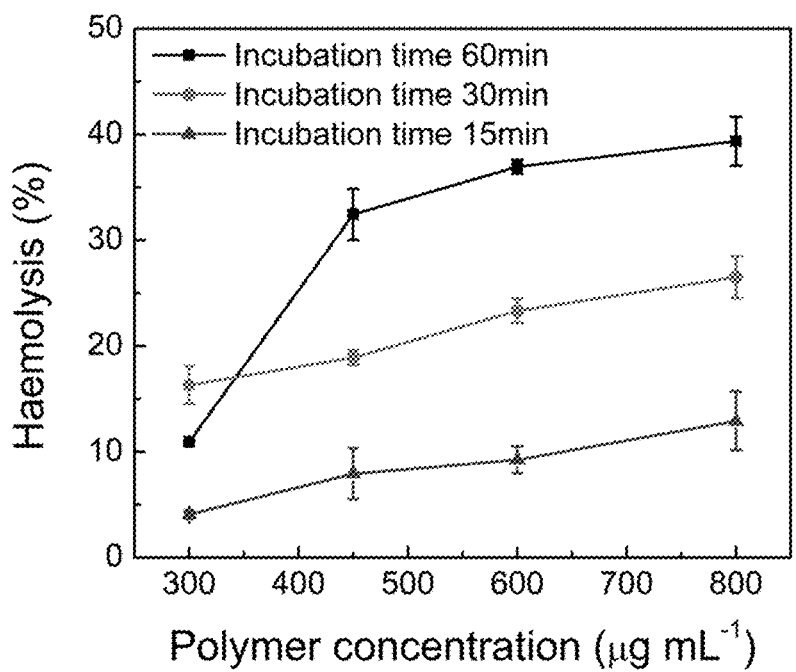
Figure 19:
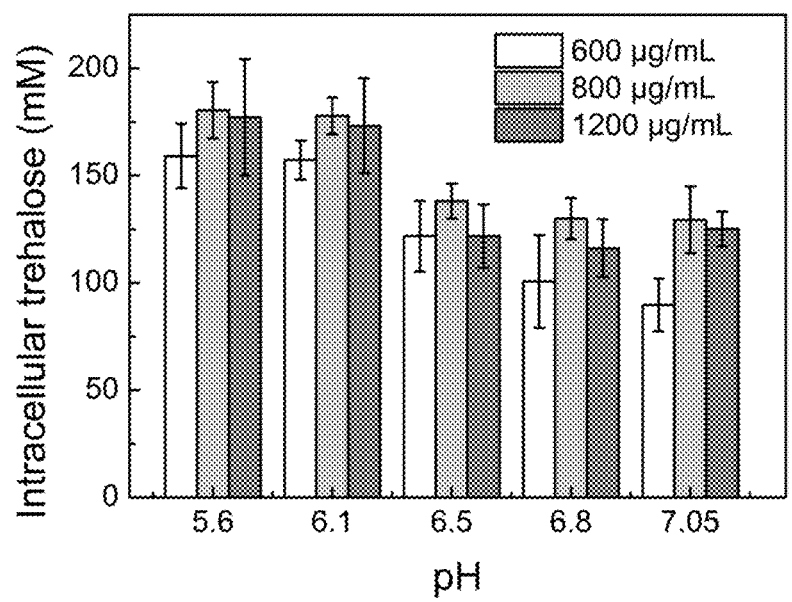
Figure 20:
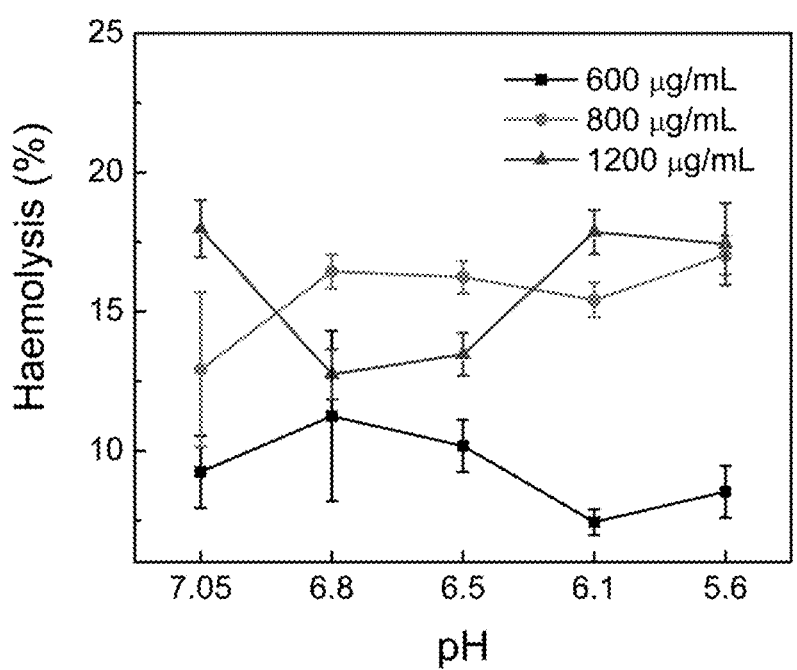
Figure 21:
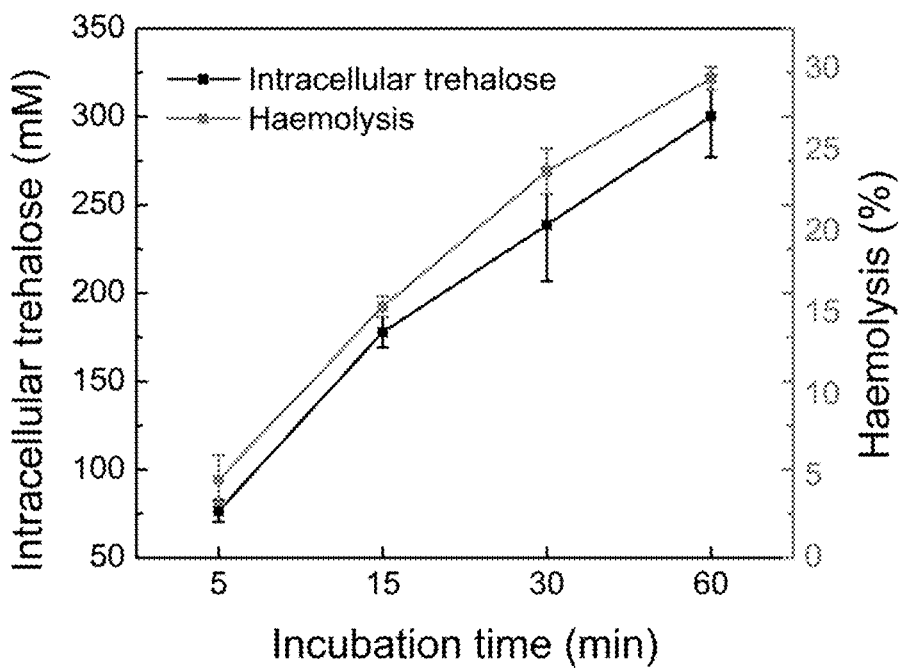
Figure 22:
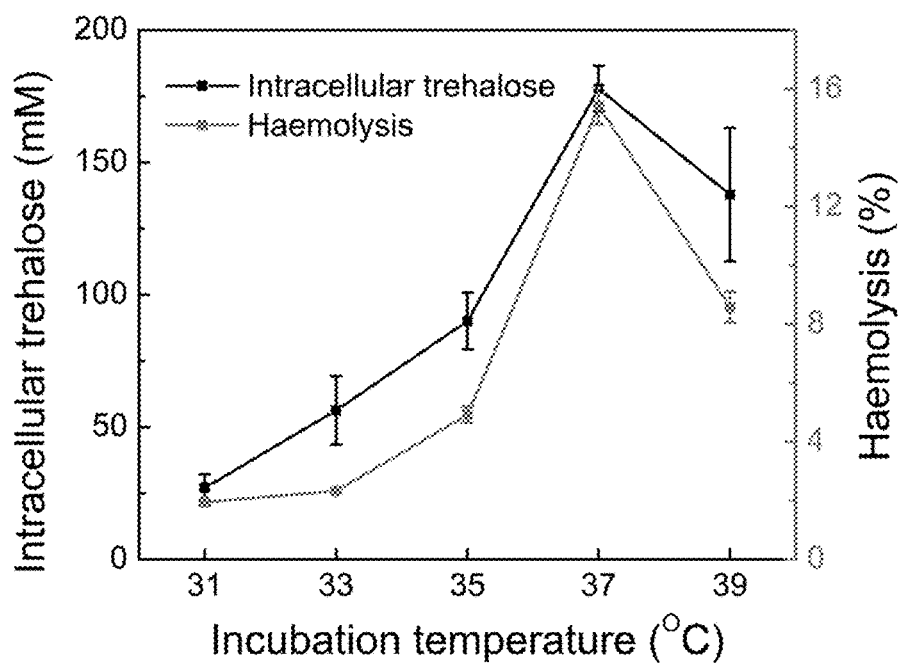
Figure 23:
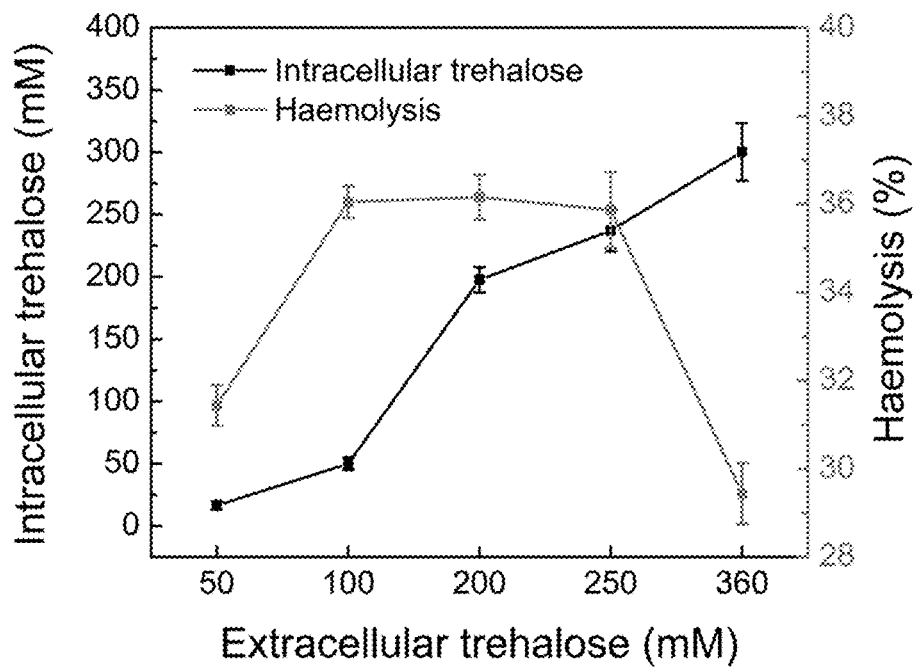
Figure 24:
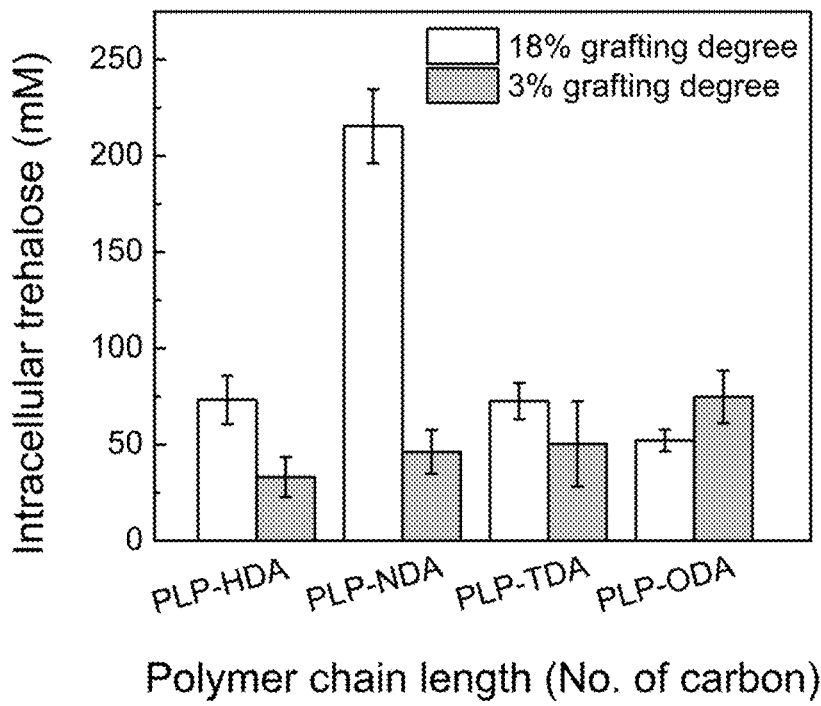
Figure 25:
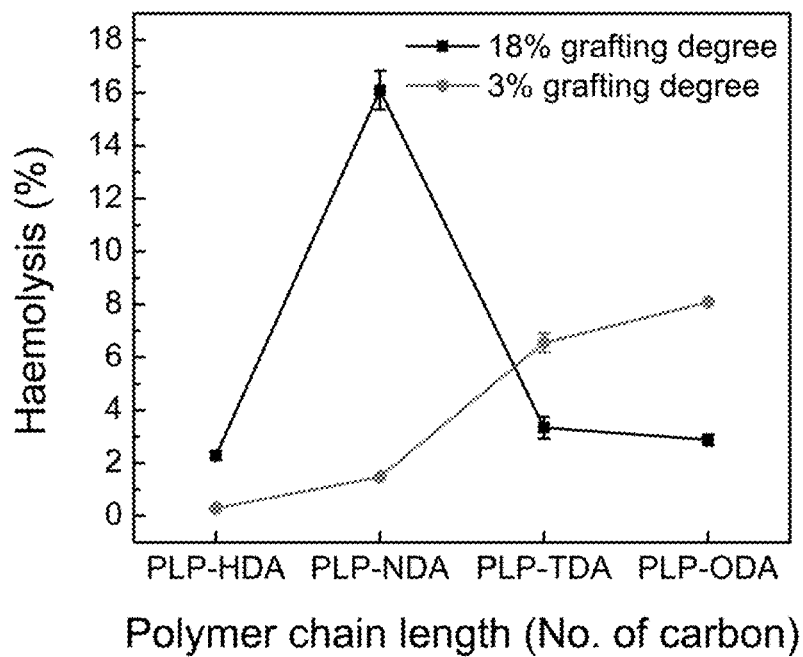
Figure 26:
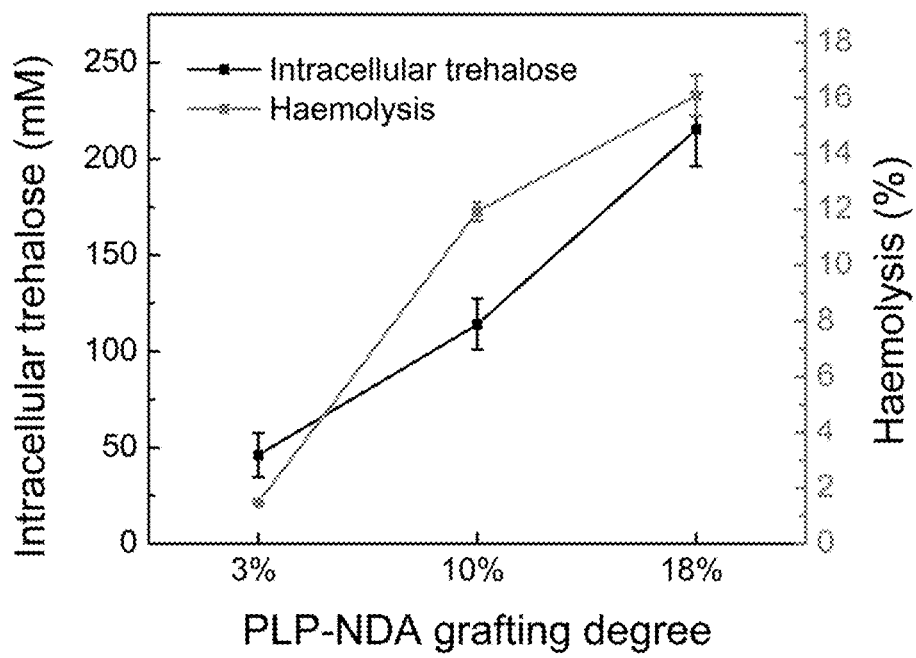
Figure 27:
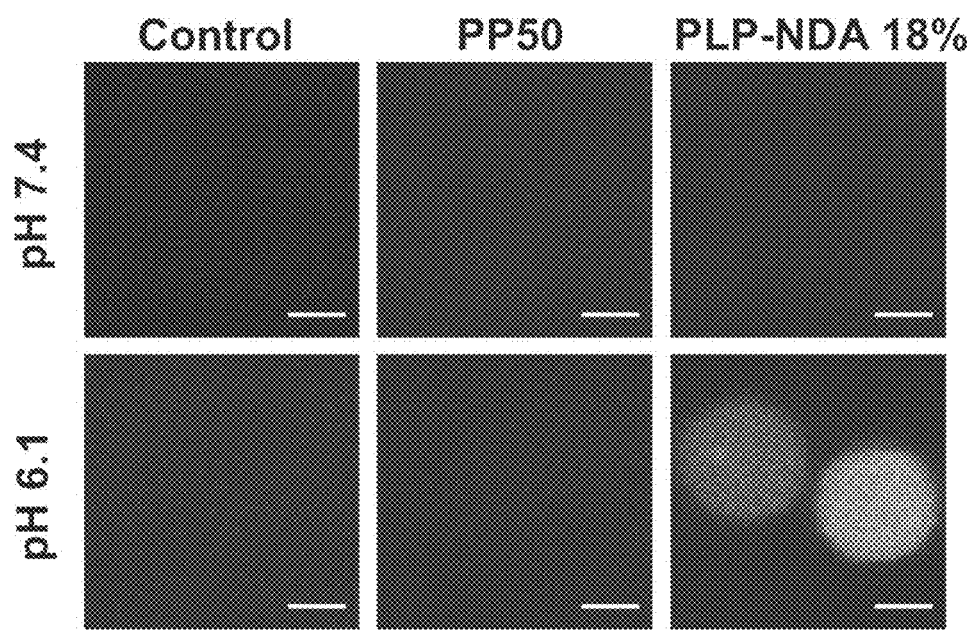

FIG. 18: Haemolysis of erythrocytes (packed volume of 15%, 3.5×10$^9$ cells per mL) in 0.36 M trehalose solution and with addition of different concentrations of PLP-NDA 18%. [PLP-NDA 18%]=300, 450, 600 and 800 µg mL$^{-1}$; incubation time=15 min, 30 min and 1 h; temperature=37° C. and pH=7.05. Supernatants were collected and the absorbance was measured by UV-VIS spectrophotometry at 541 nm. Data were derived from three replicates. Error bars represent standard deviations;

FIG. 19: Trehalose loading of erythrocytes (packed volume of 15%, 3.5×10$^9$ cells per mL) in 0.36 M trehalose solution and with addition of different concentrations of PLP-NDA 18%. [PLP-NDA 18%]=600, 800, 1200 µg mL$^{-1}$; incubation time=15 min, temperature=37° C. and pH=7.05, 6.8, 6.5, 6.1, 5.6. The intracellular trehalose concentration was calculated by the anthrone method. Data were derived from three replicates. Error bars represent standard deviations;

FIG. 20: Haemolysis of erythrocytes (packed volume of 15%, 3.5×10$^9$ cells per mL) in 0.36 M trehalose solution and with addition of different concentrations of PLP-NDA 18%. [PLP-NDA 18%]=600, 800, 1200 µg mL-1; incubation time=15 min, temperature=37° C. and pH=7.05, 6.8, 6.5, 6.1, 5.6. Supernatants were collected and the absorbance was measured by UV-VIS spectrophotometry at 541 nm. Data were derived from three replicates. Error bars represent standard deviations;

FIG. 21: Time dependent trehalose loading and haemolysis of erythrocytes (packed volume of 15%, 3.5×10$^9$ cells per mL) in 0.36 M trehalose solution and with addition of 800 µg mL$^{-1}$ PLP-NDA 18%. Temperature=37° C. and pH=6.1. The intracellular trehalose concentration was calculated by the anthrone method. Supernatants were collected and the absorbance was measured by UV-VIS spectrophotometry at 541 nm. Data were derived from three replicates. Error bars represent standard deviations;

FIG. 22: Temperature dependent trehalose loading and haemolysis of erythrocytes (packed volume of 15%, 3.5×10$^9$ cells per mL) in 0.36 M trehalose solution and with addition of 800 µg mL$^{-1}$ PLP-NDA 18%. Incubation time=15 min and pH=6.1. The intracellular trehalose concentration was calculated by the anthrone method. Supernatants were collected and the absorbance was measured by UV-VIS spectrophotometry at 541 nm. Data were derived from three replicates. Error bars represent standard deviations;

FIG. 23: Impact of extracellular trehalose concentration on trehalose loading and haemolysis of erythrocytes (packed volume of 15%, 3.5×10$^9$ cells per mL) in trehalose solution and with addition of 800 µg mL$^{-1}$ PLP-NDA 18%. Incubation time=1 h, temperature=37° C. and pH=6.1. The intracellular trehalose concentration was calculated by the anthrone method. Supernatants were collected and the absorbance was measured by UV-VIS spectrophotometry at 541 nm. Data were derived from three replicates. Error bars represent standard deviations;

FIG. 24: Impact of the length of hydrophobic pendant chains on trehalose loading. Erythrocytes (packed volume of 15%, 3.5×10$^9$ cells per mL) were treated in 0.36 M trehalose solution containing of 800 µg mL$^{-1}$ PLP-HAD (7-carbon chain), PLP-NDA (10-carbon chain), PLP-TDA (14-carbon chain) and PLP-ODA (18-carbon chain). Incubation time=15 min; temperature=37° C. and pH=6.1. The intracellular trehalose concentration was calculated by the anthrone method. Data were derived from three replicates. Error bars represent standard deviations;

FIG. 25: Impact of the length of hydrophobic pendant chains on haemolysis. Erythrocytes (packed volume of 15%, 3.5×10$^9$ cells per mL) were treated in 0.36 M trehalose solution containing of 800 µg mL$^{-1}$ PLP-HAD (C7 chain), PLP-NDA (C10 chain), PLP-TDA (C14 chain) and PLP-ODA (C18 chain). Incubation time=15 min; temperature=37° C. and pH=6.1. Supernatants were collected and the absorbance was measured by UV-VIS spectrophotometry at 541 nm. Data were derived from three replicates. Error bars represent standard deviations;

FIG. 26: Impact of the degree of grafting with the hydrophobic pendant chain NDA on trehalose loading and haemolysis. Erythrocytes (packed volume of 15%, 3.5×10$^9$ cells per ml) were treated in 0.36 M trehalose solution containing of 800 µg mL$^{-1}$ PLP-NDA at the degrees of grafting of 3%, 10% and 18%. Incubation time=15 min; temperature=37° C. and pH=6.1. The intracellular trehalose concentration was calculated by the anthrone method. Supernatants were collected and the absorbance was measured by UV-VIS spectrophotometry at 541 nm. Data were derived from three replicates. Error bars represent standard deviations;

FIG. 27: Confocal microscopy images of polymer-mediated delivery into erythrocytes. Erythrocytes (packed volume of 15%, 3.5×10$^9$ cells per mL) were co-incubated with 0.36 M trehalose and 0.1 mM calcein in the absence or in the presence of 800 µg mL$^{-1}$ PP50 (PLP grafted with L-phenylalanine) or PLP-NDA 18% at different pHs for 15 min, temperature=37° C. Scale bar: 2 µm.

Figure 28:
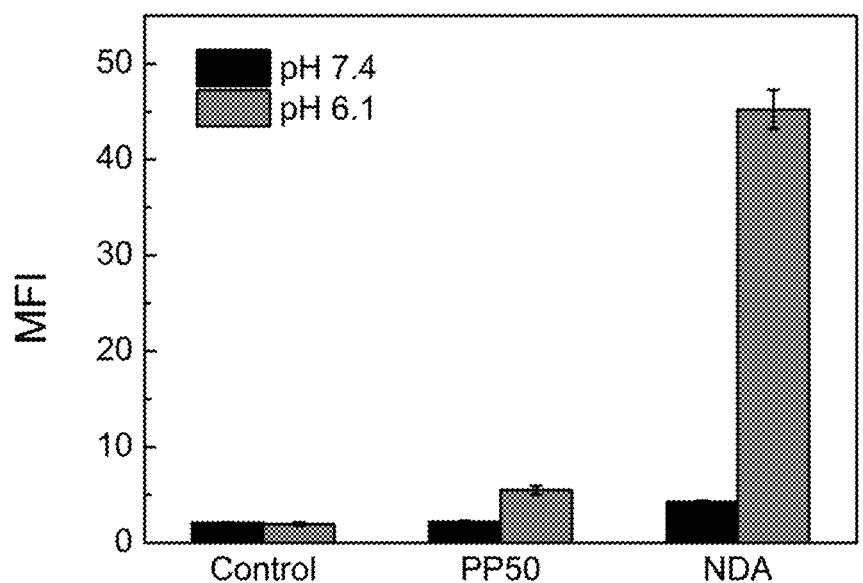

FIG. 28: Flow cytometry analysis of polymer-mediated delivery into erythrocytes. Erythrocytes (packed volume of 15%, 3.5×10$^9$ cells per mL) were incubated with 0.36 M trehalose and 0.1 mM calcein in the absence or in the presence of 800 µg mL$^{-1}$ PP50 or PLP-NDA 18% at different pHs for 15 min, temperature=37° C. Mean±S.D. (n=3).

FIGS. 29(A)-(B): Confocal microscopy images showing the membrane integrity after trehalose loading. FIG. 29(A) Erythrocytes incubated with 0.36 M trehalose in PBS buffer at pH 6.1 for 15 min, washed with pH 7.4 buffer twice and incubated with 1 μM calcein at pH 7.4. FIG. 29(B) Erythrocytes treated with 800 μg mL$^{-1}$ PLP-NDA 18% and 0.36 M trehalose in PBS buffer at pH 6.1 for 15 min, washed with pH 7.4 buffer and incubated with 1 μM calcein at pH 7.4. Scale bar: 4 μm.

FIG. 30: Topographic AFM micrographs of the erythrocyte membrane surface treated with different polymers. Erythrocytes (packed volume of 15%, 3.5×109 cells per mL) were incubated with 0.36 M trehalose solution in the absence or in the presence of 800 μg mL-1 PP50 or PLP-NDA 18% at pH 6.1 for 15 min at 37° C. The cells were immobilized on a polylysine coated microscope slide, cross-linked in glutaraldehyde (1%), washed three times with deionized water and then air dried. AFM was performed using the Asylum MFP-3D microscope in the tapping mode. Nanosensors PPP-NCHR tips (resonant frequency=app. 320 kHz nom. tip radius 7 nm, nom. Spring constant 42 N m-1) were used and tuned to a target tapping amplitude of 1-2 V.

Figure 31:
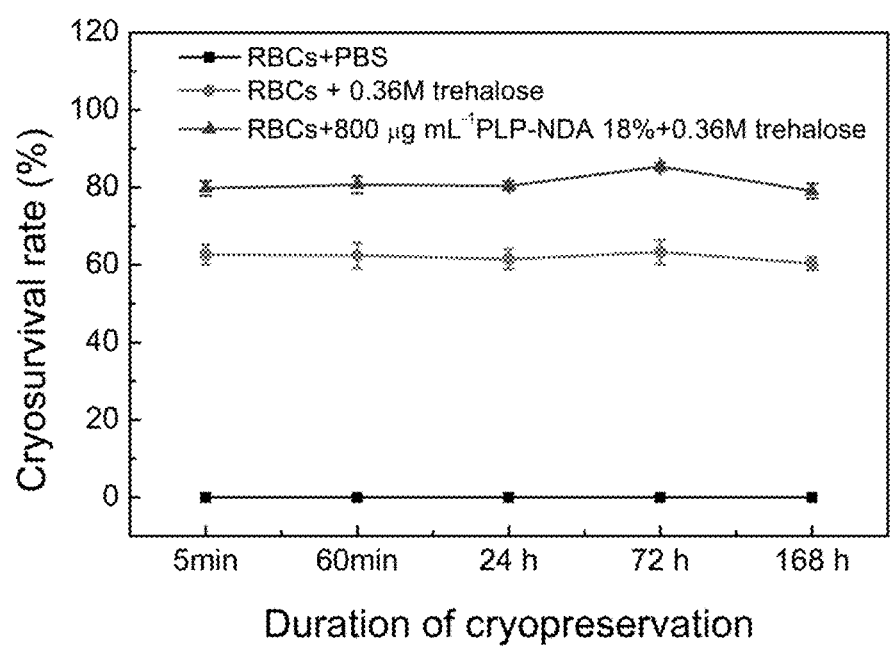

FIG. 31: Cryosurvival (%) of erythrocytes. Erythrocytes (packed volume of 15%, 3.5×10$^9$ cells per mL) were suspended in 306 mOsm PBS buffer (■), in 0.36 M extracellular trehalose solution at pH 7.05 (●), and in 0.36 M extracellular trehalose solution at pH=6.10 containing 800 μg mL$^{-1}$ PLP-NDA 18% (▲). Incubation time=15 min and temperature=37° C. After trehalose loading, erythrocytes were transferred into 2-mL cyrovial tubes followed by immersion into liquid nitrogen (−196° C.) for a certain period of time. The erythrocytes were then thawed in a 37° C. water bath for 15 min. Data were derived from three replicates. Error bars represent standard deviations.

TABLE 1 pH values at the onset of precipitation (pH$_p$), hydrophobic association (pH$_h$), pH ranges for association and the critical association concentrations (CAC) of PLP and its derivatives.

|  | PLP | PLP-NDA 3% | PLP-NDA 10% | PLP-NDA 18% |
|---|---|---|---|---|
| pH$_p$ | 4.5 | 4.5 | 4.5 | 5.0 |
| pH$_h$ | 4.8 ± 0.2 | 5.0 ± 0.2 | 6.0 ± 0.2 | N/A |
| pH range | 3.5-4.8 | 4.0-5.0 | 3.5-6.0 | N/A |
| CAC (mg mL$^{-1}$) | N/A | 0.342 | 0.282 | 0.031 |

TABLE 2

The mean hydrodynamic diameters of PLP and its derivatives at concentration of 0.5 mg mL$^{-1}$ at pH 7.4.

|  | PLP | PLP-NDA 3% | PLP-NDA 10% | PLP-NDA 18% |
|---|---|---|---|---|
| Population 1 mean size (nm) | 10.3 ± 2.3 | 4.9 ± 1.2 | 22.7 ± 5.3 | 6.5 ± 2.0 |
| Population 2 mean size (nm) | 384. ± 34.5 | 183.4 ± 12.6 | 151.3 ± 11.7 | 51.9 ± 1.6 |

TABLE 3

The mean hydrodynamic diameters of PLP-NDA 18% with various concentrations at pH 7.4.

|  | 2 mg mL$^{-1}$ | 1 mg mL$^{-1}$ | 0.5 mg mL$^{-1}$ | 0.1 mg mL$^{-1}$ | 0.05 mg mL$^{-1}$ |
|---|---|---|---|---|---|
| Population 1 mean size (nm) | 8.1 ± 1.6 | 6.3 ± 0.9 | 6.5 ± 2.0 | 6.3 ± 2.7 | 6.4 ± 3.6 |
| Population 2 mean size (nm) | N/A | 28.3 ± 2.4 | 51.9 ± 1.6 | 102.1 ± 3.2 | 122.7 ± 12.6 |

TABLE 5

Roughness Average (Ra) or Root Mean Square Roughness (RMS) of erythrocytes treated with different polymers. Erythrocytes (packed volume of 15%, 3.5 × 109 cells per mL) were incubated with 0.36M trehalose solution in the absence or presence of 800 μg mL$^{-1}$ PP50 or PLP-NDA 18% at pH 6.1 for 15 min at 37° C. The cells were immobilized on a polylysine coated microscope slide, cross linked in glutaraldehyde (1%), washed three times with deionized water and then air dried, followed by the AFM measurement.

|  | Ra (nm) | RMS (nm) |
|---|---|---|
| Control | 0.6101 | 0.8419 |
| PP50 | 2.461 | 3.122 |
| PLP-NDA 18% | 17.16 | 21.35 |

Materials and Methods

Decylamine (NDA), heptylamine (HDA), tetradecylamine (TDA), octadecylamine (ODA), iso-phthaloyl chloride, fluorescein isothiocyanate-dextran (FITC-dextran, average Mw 4K, 10K, 70K, 150K and 2000K), Dulbecco's modified Eagle's medium (DMEM), fetal bovine serum (FBS), MEM non-essential amino acid solution, Dulbecco's Phosphate Buffered Saline (D-PBS), penicillin and anthrone were purchased from Sigma Aldrich (Dorset, UK). Dimethyl sulfoxide (DMSO), pyrene, N,N-dimethylformamide (DMF), 4-dimethylaminopyridine (DMAP), AlamarBlue®, methanol (299.8%), sodium chloride, sodium phosphate dibasic heptahydrate, potassium chloride and potassium dihydrogen orthophosphate were obtained from Fisher Scientific (Loughborough, UK). lysine methyl ester dihydrochloride, N,N'-dicyclohexylcarbodiimide (DCC), triethylamine, ninhydrin and D-(+)-Trehalose dihydrate (≥99%) were purchased from Alfa Aesar (Heysham, UK). Anhydrous ethanol, acetone, hydrochloric acid, sodium hydroxide, chloroform, diethyl ether and sulphuric acid (≥95%) were obtained from VWR (Lutterworth, UK). Defibrinated sheep red blood cells (RBCs) were purchased from TCS Biosciences Ltd (Buckingham, UK), stored in a 4° C. refrigerator and used within one week once obtained.

Poly(propylene glycol)-, polyethylene-, and polystyrene-based polymers are available from Sigma. Fatty acids are available from 3B Scientific Corporation. The following compounds were purchased from Sigma N-(2-Naphthyl)-1-naphthylamine (762660), c-(2-p-Tolyl-imidazo[1,2-a]pyridin-3-yl)-methylamine (CDS008330), 1,1-bis(4-chlorophenyl)-2-[(2-fluorobenzyl)amino]-1-ethanol (CDS018870), 4-Tetradecylaniline (233552), Bis[2-(di-tert-butylphosphino)ethyl]amine solution (739022), 3-(Fmoc-amino)benzonitrile (750352), h-cys(trt)-nh2 (CDS018559), 1,7-Dibenzyl-1,4,7,10-tetraazacyclododecane (CDS001040), 2-(3-oxo-decahydro-quinoxalin-2-yl)-N-(4-phenoxy-phenyl)-acetamide (CDS018799), pontacyl carmine 2b (CDS010534), 2-[(2-amino-4-methylphenyl)sulfanyl]-N-(2-methylphenyl)acetamide (CDS015863), 4-Nitrophenethylamine hydrochloride (184802), 3-(Ethoxydimethylsilyl)propylamine (588857), Decylamine (D2404), Octadecylamine (74750), Dihexylamine (131202), Dioctadecylamine (42358), 3-Butenylamine hydrochloride (597678), Oleylamine (O07805).

Ethyl(prop-2-en-1-yl)amine (MolPort-000-005-271) but-3-yn-1-amine hydrochloride (MolPort-004-968-587), bis(but-2-yn-1-yl)amine (MolPort-001-991-305) and bis[(2Z)-3-chlorobut-2-en-1-yl]amine (MolPort-000-163-345) was purchased from MolPort.

Methyl[7-(methylimino)hepta-1,3,5-trien-1-yl]amine (FCH4099593), 3-fluoro-2-methyloct-7-yn-1-amine (BBV-70832810), [4,4-dimethyl-2-(pent-4-yn-1-yl)cyclohexyl]methanamine (BBV-49722550), (8-aminoocta-1,3,5,7-tetrayn-1-yl)borane (FCH1957383), (1,2,3,6-tetrahydropyridin-4-yl)phosphonic acid was purchased from EnamineStore (EN300-298509) and (dec-1-yn-4-yl)(propyl)amine (CSC013776799) was purchased from Chemspace.

Polymer Synthesis
Synthesis of Poly(Lysine Isophthalamide) (PLP)

PLP was synthesized using the single phase polymerization technique. In a typical procedure, lysine methyl ester.2HCl (0.15 mole) and potassium carbonate (0.6 mole) were dissolved in 750 mL of deionized water and stirred in an ice bath. To this was added rapidly 750 mL of a pre-cooled solution of anhydrous iso-phthaloyl chloride in dried acetone (0.2 M). The reaction was allowed to proceed until precipitation of poly(lysine methyl ester iso-phthalamide) (PLP methyl ester). The polymer was washed several times with deionized water, and dried overnight.

5 wt % NaOH solution in anhydrous ethanol (2.5 molar equivalents to PLP methyl ester) was added in several portions to a solution of PLP methyl ester in dry DMSO at the same volume (0.5 M). The hydrolysed product precipitated out in 2-3 minutes, and was collected by vacuum filtration and redissolved in deionized water. The crude polymer solution was dialysed in Visking tubing membrane (Medicell, MWCO 12-14 kDa) against deionized water to remove inorganic salts, residual organic solvents and low molecular weight oligomers. Solid impurities were removed by vacuum filtration. The clear solution was concentrated, adjusted to ~pH 7.4 using a NaOH aqueous solution, and lyophilized to produce PLP in the sodium salt form. In order to prepare its neutral form, the dialysed polymer solution was acidified to pH~3.0 with a dilute HCl solution. The precipitate was collected by vacuum filtration, washed three times with deionized water, and lyophilized to fine white powder.

Synthesis of PLP Derivatives

NDA, HDA, TDA or ODA was conjugated onto the PLP backbone at various degrees of substitution via DCC/DMAP coupling. Briefly, PLP (3 g), DMAP (0.6 g, 20 wt % of PLP) were dissolved in anhydrous DMSO/DMF (1:3 v/v). NDA, HDA, TDA or ODA was dissolved in chloroform and then transferred to the reaction solution. DCC (3 molar equivalents of decylamine) in anhydrous DMF was added dropwise. The reaction was monitored by thin-layer chromatography ($CHCl_3$:MeOH:trithylamine=8:2:0.2, using ninhydrin to visualise amine). Solid impurities were removed by vacuum filtration and the reaction solution was added with 5 wt % NaOH in anhydrous ethanol and precipitated rapidly into five volumes of diethyl ether. The precipitate was collected and re-dissolved in deionized water. 0.2 M HCl solution was added to the solution to precipitate the polymer precipitate out. It was collected by vacuum filtration and re-dissolved in deionized water with 0.2 M NaOH. The precipitation-filtration-redissolution process was carried out twice to remove inorganic salts and residual organic solvents. The polymer was further purified by dialysis against deionized water in a Visking dialysis tubing (Medicell, MWCO 12-14 kDa). After dialysis, the polymer solution was titrated to pH 7.4 using 0.2 M NaOH and then lyophilized. To prepare acidic form, the dialysed polymer solution was acidified to around pH 3.0 using 0.2 M HCl. The precipitate was collected and lyophilized.

The Mw of PLP (35.7 kDa) was determined an aqueous gel permeation chromatography (GPC) system. That means value of the degree of polymerization (n) is ~130. The degree of substitution of each polymer was determined by $^1$H-NMR spectroscopy in $d_6$-DMSO (FIG. 1A). The ratio of the integral 0.77-0.91 ppm to the integral 7.45-7.64 ppm was used to calculate the degree of substitution. PLP-NDA 3%, 10% and 18% are expressed as the numbers of NDA grafts per 100 carboxylic acid groups along the parent backbone (mol %). The degree of substitution and the Mw of PLP were then used to calculate the molecular weight of the derivative containing hydrophobic pendant chains.

Further PLP derivates can be obtained by reacting chemical compounds of table 4 with the PLP backbone via DCC/DMAP coupling as described above.

TABLE 4

| Moeity | Example Chemical of formula $HNR^1R^2$ | Supplier | Catalogue number |
| --- | --- | --- | --- |
| $R^1$ = Alkyl chain short; $R^2$ = H | Decylamine | Sigma | D2404 |
| $R^1$ = Alkyl chain medium $R^2$ = H | Octadecylamine | Sigma | 74750 |
| $R^1$ = $R^2$ = Alkyl chain short | Dihexylamine | Sigma | 131202 |
| $R^1$ = $R^2$ = Alkyl chain medium | Dioctadecylamine | Sigma | 42358 |
| $R^1$ = Alkenyl chain short $R^2$ = H | 3-Butenylamine hydrochloride | Sigma | 597678 |
| $R^1$ = Alkenyl chain short $R^2$ = H | 5-Hexenylamine | GFS Chemicals | 5529 |
| $R^1$ = Alkenyl chain short $R^2$ = H | oct-3-en-1-amine | Enamine Store | BBV-42249046 |

TABLE 4-continued

| Moeity | Example Chemical of formula HNR$^1$R$^2$ | Supplier | Catalogue number |
|---|---|---|---|
| R$^1$ = Alkenyl chain medium R$^2$ = H | tetradec-3-en-1-amine | Enamine Store | BBV-42256359 |
| R$^1$ = Alkenyl chain medium R$^2$ = H | Oleylamine | Sigma | O7805 |
| R$^1$ = R$^2$ = Alkenyl chain short | ethyl(prop-2-en-1-yl)amine | MolPort | MolPort-000-005-271 |
| R$^1$ = R$^2$ = Alkenyl chain medium | bis[(2Z)-3-chlorobut-2-en-1-yl]amine | MolPort | MolPort-000-163-345 |
| R$^1$ = Alkenyl chain with multiple C=C groups R$^2$ = Alkyl chain short | methyl[7-(methylimino)hepta-1,3,5-trien-1-yl]amine | Enamine Store | FCH4099593 |
| R$^1$ = Alkynyl chain short R$^2$ = H | but-3-yn-1-amine hydrochloride | MolPort | MolPort-004-968-587 |
| R$^1$ = Alkynyl chain short R$^2$ = H | Hex-5-ynylamine | Activate Scientific | AS74680 |
| R$^1$ = Alkynyl chain short R$^2$ = H | oct-3-yn-1-amine | Enamine Store | FCH935266 |
| R$^1$ = Alkynyl chain medium R$^2$ = H | dodec-3-yn-1-amine | Enamine Store | FCH1282159 |
| R$^1$ = Alkynyl chain medium R$^2$ = H | 3-fluoro-2-methyloct-7-yn-1-amine | EnamineStore | BBV-70832810 |
| R$^1$ = Alkynyl chain medium R$^2$ = H | [4,4-dimethyl-2-(pent-4-yn-1-yl)cyclohexyl]methanamine | EnamineStore | BBV-49722550 |
| R$^1$ = R$^2$ = Alkynyl chain short | bis(but-2-yn-1-yl)amine | MolPort | MolPort-001-991-305 |
| R$^1$ = Alkynyl chain medium R$^2$ = Alkyl chain short | (dec-1-yn-4-yl)(propyl)amine | Chemspace | CSC013776799 |
| EXAMPLES OF SUSTITUTIONS | | | |
| R1 and R2 are aryls | N-(2-Naphthyl)-1-naphthylamine | Sigma | 762660 |
| R$^1$ = Heteroaryl R$^2$ = H | c-(2-p-Tolyl-imidazo[1,2-a]pyridin-3-yl)-methylamine | Sigma | CDS008330 |
| R$^1$ = Alkyl substituted with aryl and OH; R$^2$ = alkyl substituted with aryl | 1,1-bis(4-chlorophenyl)-2-[(2-fluorobenzyl)amino]-1-ethanol | Sigma | CDS018870 |
| R$^1$ = aryl substituted with alkyl R$^2$ = H | 4-Tetradecylaniline | Sigma | 233552 |
| R$^1$ = R$^2$ = alkyl substituted with PR$^3$R$^4$ | Bis[2-(di-tert-butyphosphino)ethyl]amine solution | Sigma | 739022 |
| R$^1$ = alkyl substituted with aryl R$^2$ = alkyl substituted with SH and C(O)NH$_2$ | h-cys(trt)-nh2 | Sigma | CDS018559 |
| R$^1$ and R$^2$ together form a heterocyclic ring optionally containing further heteroatoms | 1,7-Dibenzyl-1,4,7,10-tetraazacyclododecane | Sigma | CDS001040 |
| Cyclic, amide and ether | 2-(3-oxo-decahydro-quinoxalin-2-yl)-N-(4-phenoxy-phenyl)-acetamide | Sigma | CDS018799 |
| thioether | 2-[(2-amino-4-methylphenyl)sulfanyl]-N-(2-methylphenyl)acetamide | Sigma | CDS015863 |
| R$^1$ = alkyl substituted with aryl R$^2$ = H | 4-Nitrophenethylamine hydrochloride | Sigma | 184802 |

Turbidimetry

The optical densities of polymer solutions at different pHs were measured on a UV-Vis spectrophotometer (Genesys 10S UV-Vis, Thermo Scientific, UK) at 480 nm. Polymer solutions were prepared with buffers at different pHs and equilibrated for 48 h.

Fluorescence Spectroscopy

Pyrene has been used as a probe to investigate the conformational transition of polymers in aqueous solution. 1.0 mM pyrene solution in absolute methanol was freshly prepared and added to each aqueous polymer solution to give a final pyrene concentration of $6\times10^{-7}$ M. The polymer solutions were equilibrated for 48 h with protection from light. The excitation intensities at wavelengths of 338 and 333 nm ($\lambda_{em}$=390 nm) of pyrene dissolved in the polymer solution were recorded on a spectrofluorometer (FluoroMax, HORIBA, Japan). The fluorescence intensity ratio of $I_{338}/I_{333}$ was calculated. The conformational transition in response to pH and concentration and the critical aggregation concentration (CAC) were then determined.

Dynamic Light Scattering

The hydrodynamic diameter and the size distribution of the polymers in aqueous solution were investigated using dynamic light scattering (Zetasizer Nano S. Malvern, UK). The polymer solutions were prepared in buffer at specific pHs and equilibrated for 48 h. All the samples were filtered through the 0.45-μm filter, and size measurements were conducted in 10-mm diameter cells at a scattering angle of 137°, repeated for 11 times for each run.

Hemolysis

The lipid membrane activity of the polymers was examined using the haemolysis assay of defibrinated sheep red blood cells (RBCs). Briefly, the polymers were added into 0.1 M phosphate buffer or 0.1 M citric buffer at specific pHs. RBCs were washed at least three times with 150 mM NaCl and resuspended in the polymer solution to a final concentration of 1-2×10$^8$ RBCs mL$^{-1}$. The negative control (without the presence of polymer) and the positive control (RBCs lysed in deionized water) were prepared with the same cell density. The samples were incubated in a shaking water bath (120 rpm) at 37° C. for a specific period, and then centrifuged at 4000 rpm for 4 min. The haemoglobin release was investigated by measuring the absorbance of the supernatant at 540 nm using the UV-Vis spectrophotometer. The relative haemolysis percentage was calculated using the following equation:

Haemolysis (%)=[(Sample absorbance−Negative control absorbance)/(Positive control absorbance−Negative control absorbance)]×100

Cell Culture

HeLa adherent epithelial cells (human cervical cancer cells) and A549 adherent epithelial cells (human lung cancer cells) were grown in DMEM supplemented with 10% (v/v) FBS and 100 U mL$^{-1}$ penicillin unless specified otherwise. CHO adherent epithelial cells (Chinese hamster ovary cells) were cultured in DMEM supplemented with 1% (v/v) non-essential amino acids, 10% (v/v) FBS and 100 U mL$^{-1}$ penicillin unless specified otherwise. The HeLa, A549 and CHO cells were trypsinized using trypsin-EDTA and maintained in a humidified incubator with 5% CO2 at 37° C.

MES-SA adherent epithelial cells (human uterus cancer cells) and the corresponding multi-drug resistant cells MES-SA/DX5 were cultured in McCoy's 5a medium containing 10% (v/v) FBS and 100 U mL$^{-1}$ penicillin unless specified otherwise. The MES-SA and MES-SA/DX5 cells were subcultured with EDTA solution (0.8 mM disodium EDTA, 68.5 mM NaCl, 6.7 mM sodium bicarbonate, 5.6 mM glucose and 5.4 mM KCl) and maintained in a humidified incubator with 5% CO2 at 37° C.

SU-DHL-8 suspension B lymphocyte cells (human lymph node cells) were grown in RPMI-1640 medium supplemented with 10% (v/v) FBS and 100 U mL$^{-1}$ penicillin and kept in a humidified incubator with 5% CO2 at 37° C.

Mesenchymal stem cells (hMSCs, human bone marrow derived) were cultured in minimum essential medium Eagle containing 10% FBS and 100 U mL$^{-1}$ penicillin. The cells were trypsinized using trypsin-EDTA and maintained in a humidified incubator with 5% CO2 at 37° C.

Alamar Blue Assay

The cytotoxicity of the polymers was evaluated using AlamarBlue® assay. Cells were seeded into 96-well plates (Corning, USA) containing culture medium (0.1 mL per well) at a density of 1×10$^4$ cells/well for 24 h. The spent medium was replaced with 0.1 mL of sample solution containing 0.22 µm filter-sterilized polymer at various concentrations. After incubation for a specific period, the polymer-containing medium was replaced with DMEM containing 10% (v/v) AlamarBlue®. The plate was further incubated for 4 h according to the manufacturer's instructions and the fluorescence of each well was then measured by a spectrofluorometer (GloMax®-Multi Detection System, Promega) at emission wavelength of 580-640 nm with the excitation wavelength of 525 nm. The cytotoxic effect was determined from the fluorescence readings.

Laser Scanning Confocal Microscopy

Calcein, a membrane-impermeable fluorophore, was employed to assess the ability of the polymers to release endocytosed materials into the cytoplasm. 2 mL of HeLa, CHO or A549 cells (2×10$^5$ cells mL-1) were seeded in glass-bottom culture dish (35 mm, MatTek, USA) and cultured in an incubator with 5% CO2 at 37° C. After 24 h, the spent medium was removed and replaced with 2 mL of 0.22 µm filter-sterilized serum-free medium containing the polymer at 0.5 mg mL$^{-1}$ and calcein at 2 mg mL$^{-1}$. In a control experiment, the cells were incubated with 2 mg mL$^{-1}$ calcein alone. After incubation for a certain period, the cells were washed three times with D-PBS buffer replenished with medium. The cells were imaged by the laser scanning confocal microscope. Calcein was excited using a 488 nm laser and the emission was collected at 535 nm.

The ability of the pseudopeptidic polymers to deliver a wide size range of FITC-labelled dextran (4-2000 kDa) was tested in 7 different cell liens. Adherent cells were cultured in a glass-bottom dish at a total cell number of 2×10$^5$ cells for overnight followed by treatment with PBS containing the pseudopeptidic polymer and FITC-dextran at specific concentrations and pHs for a certain period of time. The cells were then washed with D-PBS and stained with LysoTracker and Hoechst and imaged as described above. For the suspension cell (SU-DHL-8), the cells were centrifuged and resuspended with 1 mL of PBS buffer containing the pseudopeptidic polymer and FITC-dextran to reach a final cell concentration of 4×10$^5$ cells mL$^{-1}$. After 30 min of incubation, the cells were centrifuged to remove the supernatant and resuspended with D-PBS for three times and stained with LysoTracker and Hoechst before imaging.

Flow Cytometry

Flow cytometry was employed to quantitatively evaluate the polymer mediated payload delivery. Adherent cells were cultured in a 6-well plate (3×10$^5$ cells per well) for overnight and treated with 1 mL PBS containing the pseudopeptides and FITC-dextran at specific concentrations for a certain period of time. Afterwards, the cells were washed with D-PBS for three times, detached using trypsin and then centrifuged at 1000 rpm. The cell pellet was resuspended in serum free culture medium and filtered through 40 µm Flowmi™ tip strainers (Bel-Art, USA) to remove cell aggregates. SU-DHL-8 suspension cells (8×10$^5$ cell mL$^{-1}$) were treated with PBS containing the polymers and FITC-dextran for 30 min. The cells were then centrifuged to remove the supernatant and filtered. The flow cytometry was carried out with an LSRFortessa cell analyzer at excitation wavelength of 488 nm.

Intracellular Sugar Delivery 306 mOsm phosphate buffered saline (PBS, pH=7.4) was prepared by dissolving 136.89 mM sodium chloride, 8.10 mM sodium phosphate dibasic heptahydrate, 2.68 mM potassium chloride and 1.47 mM potassium dihydrogen orthophosphate into 1 L de-ionized water. 660 mOsm PBS buffer was made by dissolving 297.74 mM NaCl, 17.62 mM Na$_2$HPO$_4$.7H$_2$O, 5.83 mM KCl and 3.20 mM KH$_2$PO$_4$ into 1 L deionized water.

Sugar solutions (with or without polymer) were prepared by dissolving a certain amount of sugar into PBS buffer, and their pH was adjusted to a desired value. The anthrone solution was prepared by adding 125 mg of anthrone into 66% (v/v) H$_2$SO$_4$.

Sheep red blood cells were centrifuged at approximately 1200 rcf for 4 minutes. 306 mOsm PBS buffer was then added after the removal of the supernatant. This process was repeated 3 times in order to completely remove free haemoglobin. The sugar solution was added to the pre-washed RBCs achieve the 15% cell packed volume (CPV). Cells were homogeneously re-suspended into solution. Subsequently, RBCs were incubated for a certain period of time at a desired temperature.

After incubation, haemolysis was examined via the measurement of the absorbance of the supernatant at 541 nm by UV-Vis spectrophotometer. Cell pellets were washed by the iso-osmotic PBS buffer (660 mOsm) twice to remove the extracellular sugar molecules. RBCs were then lysed by 80% methanol in an 85° C. water bath for 1 hour and centrifuged at approximately 11000 rcf for 4 minutes. The supernatant was placed in an oven at 100° C. for overnight to completely remove water and methanol, followed by the addition of 2 mL deionized water. The anthrone method was then carried out to quantify the intracellular sugar concentration. Specifically, 0.5 mL of the above solution was added into the anthrone solution followed by water bath at 100° C. for the 15 minutes. Then, absorbance was measured by UV-Vis at 620 nm wavelength to calculate the amount of sugar molecules loaded into the cell interior.

Sheep red blood cells (RBCs) with a packed volume of 15% (3.5×10$^9$ RBCs per ml) were placed in a 2-mL centrifuge tube, to which was added the PBS buffer solution at the desired pH containing specific concentrations of polymer and trehalose. After incubation at 37° C. for a certain period of time, the amount of trehalose loaded into the cell interior was determined using the method described above. The blood solution was then transferred to a 2-ml polypropylene cryovial. The cryovial tubes were immersed into liquid nitrogen (−196° C.) for a certain period of time. RBCs were then thawed in a 37° C. water bath for 15 min. The cell suspension was then centrifuged and the cell pellet was lysed to calculate the amount of viable cells from the absorbance of the lysed RBC solution at 541 nm. Haemolysis during the sugar delivery and the freezing-thawing processes was also measured and used to calculate the cryosurvial rate.

Confocal Microscopy and Flow Cytometry of RBCs

Membrane-impermeable calcein was applied to further investigate the polymer-mediated delivery into erythrocytes. RBCs (15% packed cell volume) were washed three times and incubated with PBS buffer containing 0.36 M trehalose+ 0.1 mM calcein, 0.36 M trehalose+0.1 mM calcein+0.8 mg mL$^{-1}$ PP50, or 0.36 M trehalose+0.1 mM calcein+0.8 mg mL$^{-1}$ PLP-NDA 18%, respectively at pH 6.1 in a 37° C. shaking water bath (120 rpm) for 15 min. After incubation, the samples were washed twice with PBS buffer by centrifugation and imaged with an LSM-510 inverted laser scanning confocal microscope (Zeiss, Germany) at 37° C. Calcein was excited at 488 nm, and the emission at 535 nm was collected. The flow cytometry measurements were carried out using an LSRFortessa cell analyzer (BD, USA) with an excitation wavelength of 488 nm.

To evaluate the membrane permeability after trehalose loading and washing, RBCs were incubated with trehalose in the absence or in the presence of polymer at pH 6.1 at 37° C. for 15 min, followed by washing twice with pH 7.4 PBS buffer. Then the processed RBCs were incubated with pH 7.4 PBS buffer containing 1 μM calcein and imaged with the laser scanning confocal microscope as described before.

Atomic Force Microscopy (AFM)

To further study the mechanism of rapid trehalose intracellular loading mediated by PLP-NDA 18%, AFM was applied to exam the polymer-cell interaction. RBCs were washed three times, incubated with PBS buffer containing 0.36 M trehalose, 0.36 M trehalose+0.8 mg mL$^{-1}$ PP50, or 0.36 M trehalose+0.8 mg mL-1 PLP-NDA 18% at pH 6.1 for 15 min, and immobilized on a polylysine-coated microscope slide. The cells were crossed linked in glutaraldehyde (1%) for 10 min, washed and then air dried. AFM was performed using the Asylum MFP-3D microscope (Oxford instruments Asylum Research, US) in tapping mode. Nanosensors PPP-NCHR tips with resonant frequency around 320 kHz, tip radius 7 nm and spring constant 42 N m$^{-1}$ were used and tuned to a target tapping amplitude of 1-2 V.

EXAMPLE 1

Figure 1:
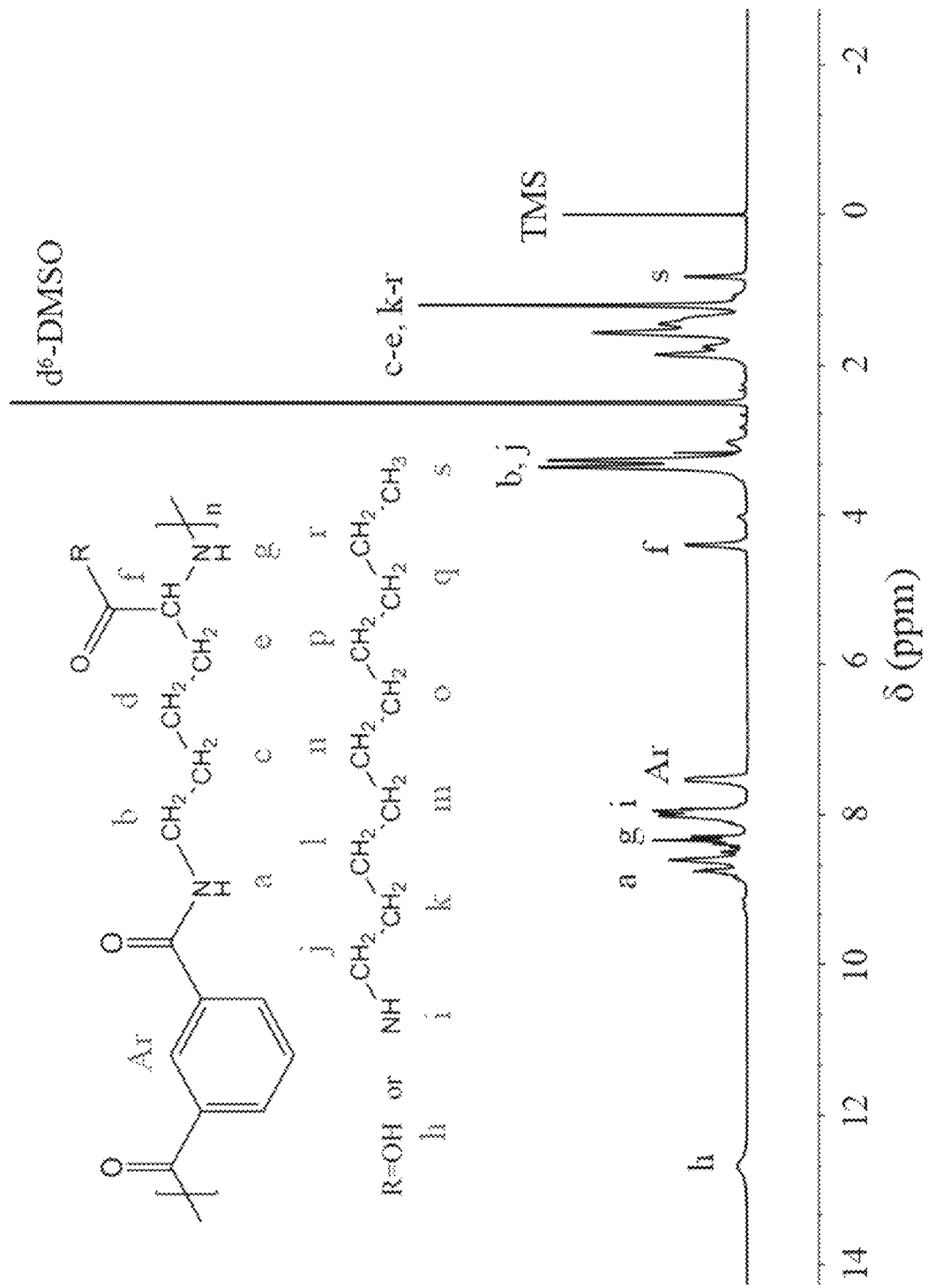
Figure 1:
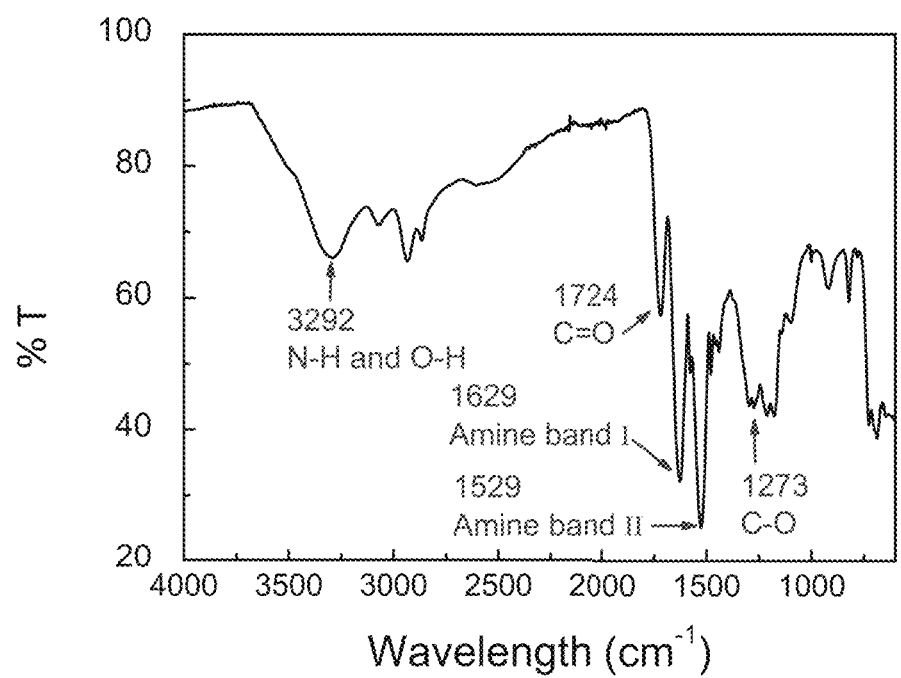

Formation of PLP grafted with NDA (C10) and other pendant hydrophobic chains including HDA (C7), TDA (C14) and ODA (C18) has been confirmed using 1H-NMR and FTIR spectra (FIG. 1).

EXAMPLE 2 pH dependent transmittance (FIG. 2A) and pH- and concentration-dependent hydrophobic association (FIGS. 2B & 2C) of the aqueous solutions of the PLP substituted with different degrees of NDA (%). As shown PLP-NDA displayed pH-dependent properties. The increase in pH at the onset of precipitation ($pH_p$) and hydrophobic association ($pH_h$), the widening of pH range for association and the decrease in CAC were achieved by grafting PLP with hydrophobic pendant side chains and increasing the degree of substitution (Table 1).

Figure 3:
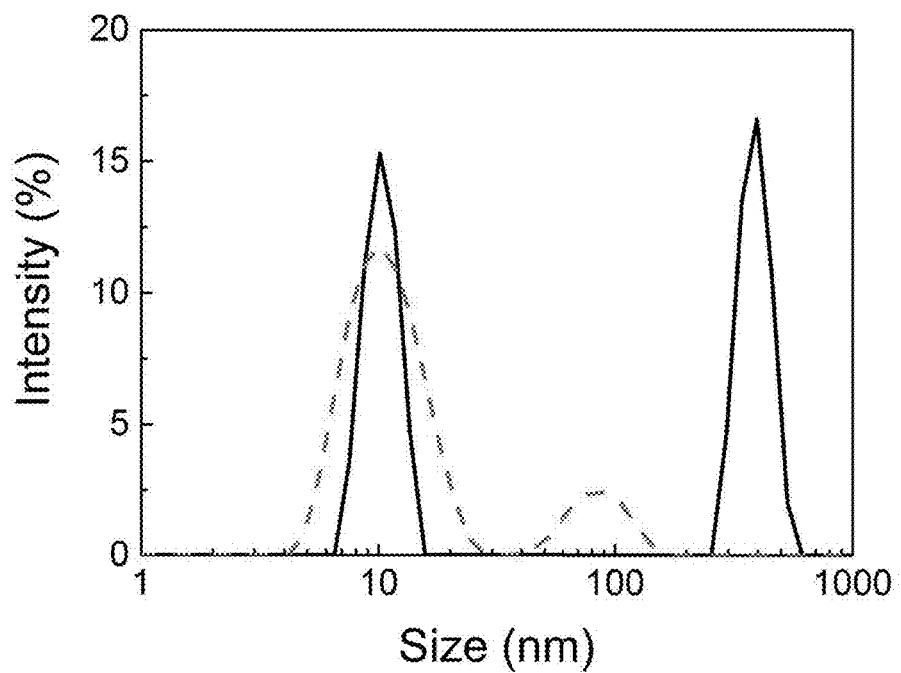
Figure 3:
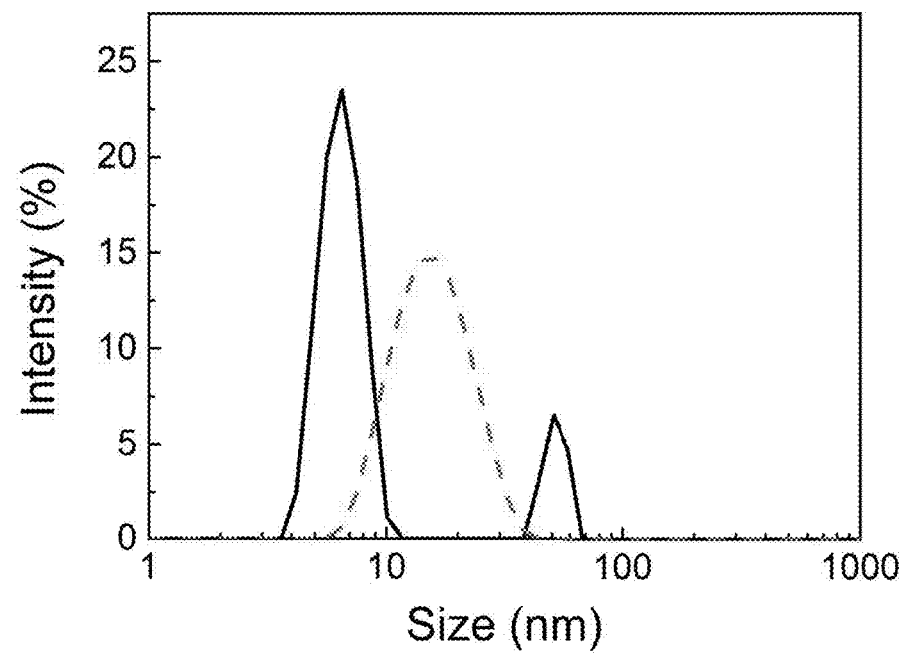

EXAMPLE 3 pH and concentration dependent particle size distribution of the polymers PLP and PLP-NDA (FIG. 3, Tables 2 & 3). The increase in the degree of substitution with hydrophobic pendant chains can lead to the decrease in particle size due to stronger hydrophobic interactions.

EXAMPLE 4

Figure 4:
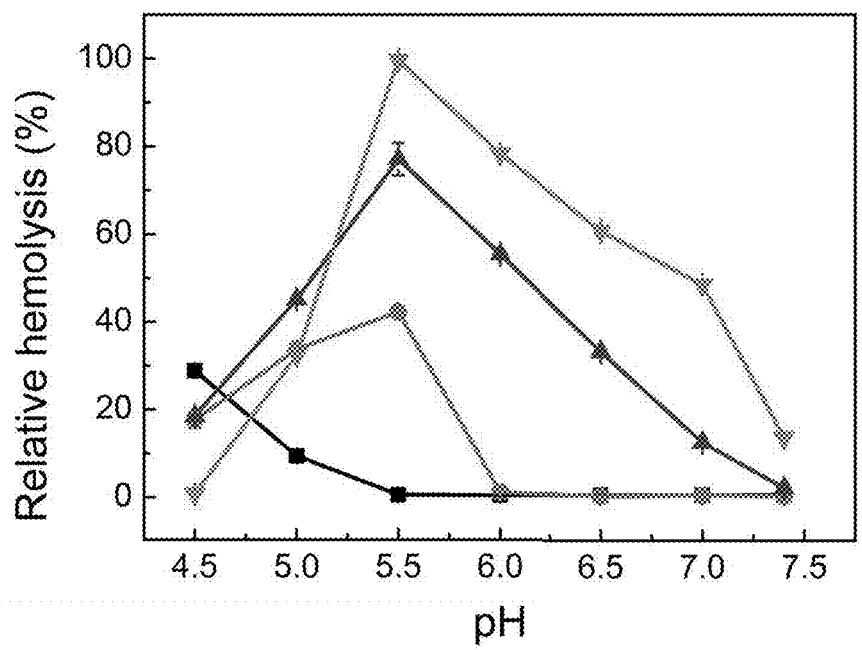
Figure 4:
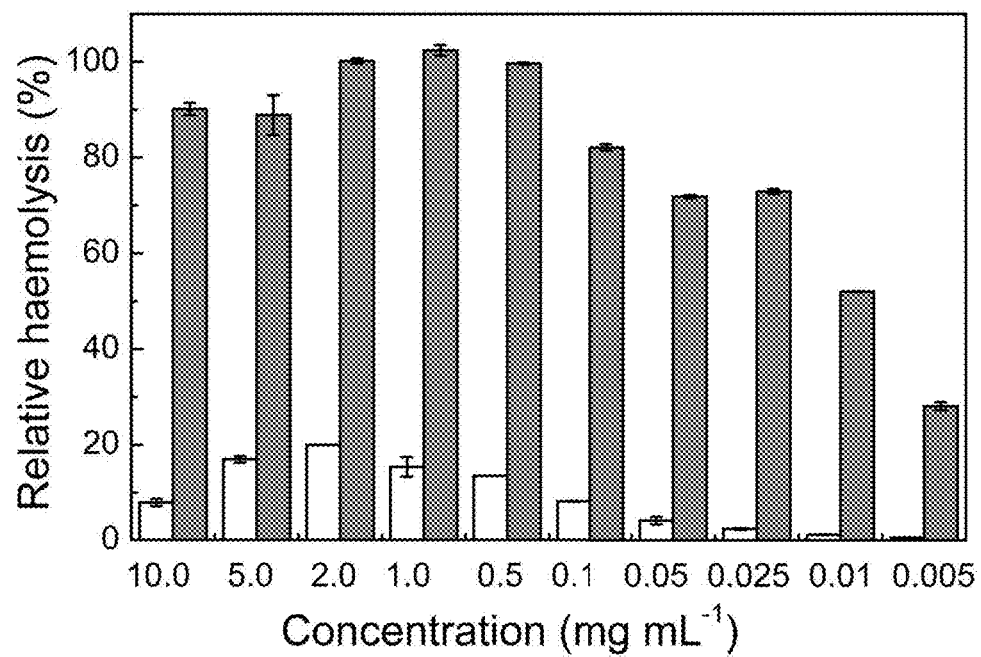
Figure 4:
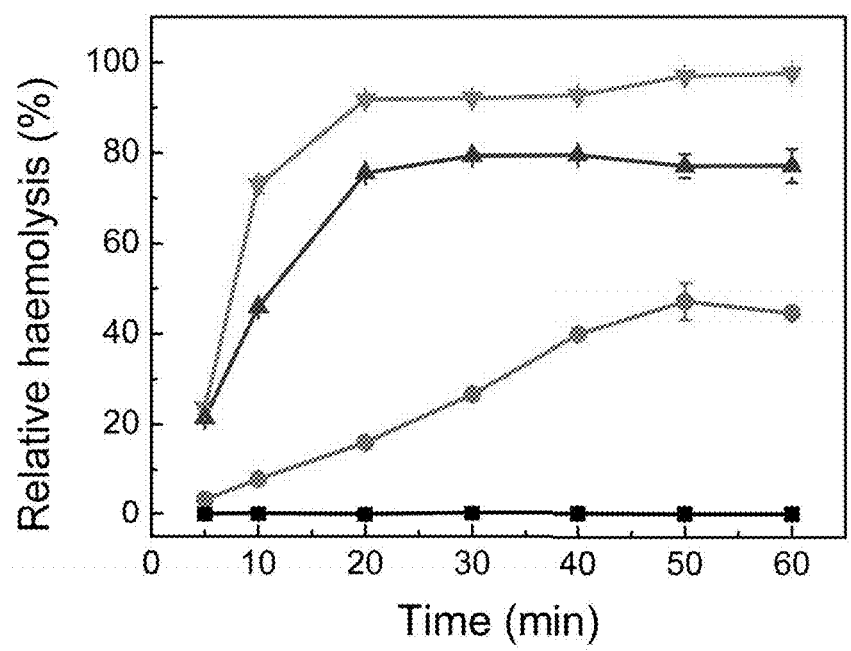

Haemolysis of red blood cells treated with PLP and its derivatives was found to be dependent on pH, concentration and incubation time (FIG. 4). The membrane activity of the polymers can be manipulated by the type of hydrophobic side chains and the degree of substitution. At pH 7.4 the level of haemolysis was found to be low or negligible, whilst upon acidification the membrane-destabilizing capacity was increased. The increase of the degree of substitution up to 18% of hydrophobic pendant chains led to enhanced membrane activity.

EXAMPLE 5

In vitro cytotoxicity of PLP-NDA 18% was tested in HeLa cells (FIG. 5A), CHO cells (FIG. 5B) and A549 cells (FIG. 5C) and at various PLP-NDA concentrations for 4 h (blank), 12 h (grey), 24 h (black) and 48 h (stripped). The $IC_{50}$ of PLP-NDA 18% against HeLa for 12 h of treatment was 2.94±0.28 mg mL$^{-1}$, while it decreased to 1.59±0.22 mg mL$^{-1}$ and 1.05±0.14 mg mL$^{-1}$ after treatment for 24 h and 48 h respectively. CHO cells demonstrated the better tolerance than HeLa cells, with $IC_{50}$ of 2.81±0.95 mg mL$^{-1}$ for 48 h treatment, while A549 showed the highest $IC_{50}$ of 4.51±0.06 mg mL$^{-1}$ for 48 h treatment. FIG. 5D shows that the cell viability of different types of cells treated with 0.5 mg mL-1 of PLP or PLP-NDA 18% for 24 h was not significantly different.

EXAMPLE 6

Hela (FIG. 6A), CHO (FIG. 6B) and A549 cells (FIG. 6C) treated with PLP-NDA 18% and membrane-impermeable calcein showed an increased fluorescent signal due to the release of endocytosed calcein into the cytoplasm when compared to cells treated with calcein alone or treated with PLP and calcein.

EXAMPLE 7

PLP-NDA 18% aided delivery of FITC-dextran with different molecular weights (Mw) into HeLa cells after incubation at pH 6.5 for 30 min (FIG. 7A). No significant transport was detected when cells were incubated with FITC-dextran only (FIG. 7B) or with PLP-NDA 18% and FITC dextran at pH 7.4 (FIG. 7C).

EXAMPLE 8

Efficient transport was dependent on the polymer concentration (FIG. 8) and was highest at the PLP-NDA 18% concentration of 0.5-2 mg mL$^{-1}$.

EXAMPLE 9

Figure 9:
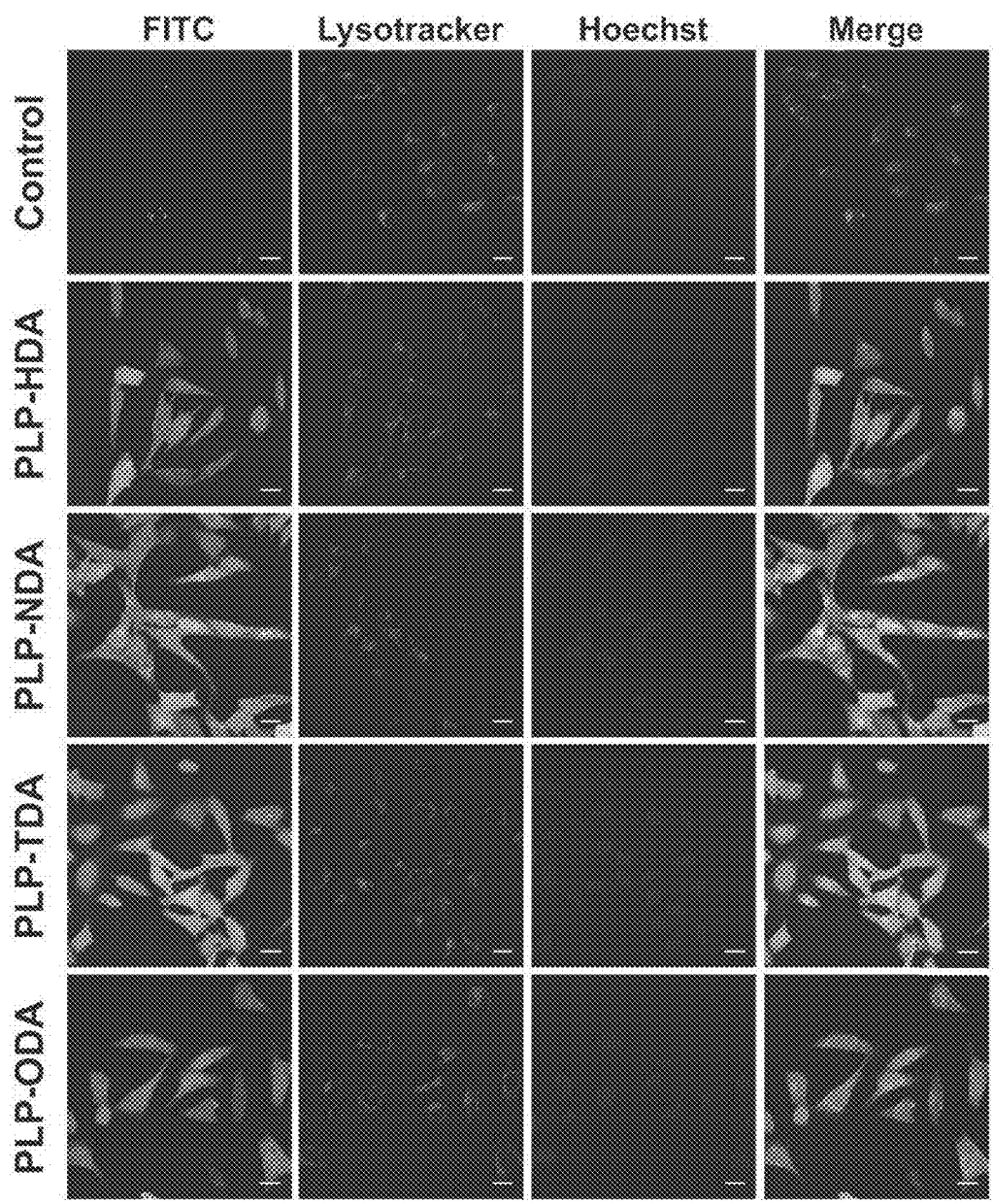
Figure 9:
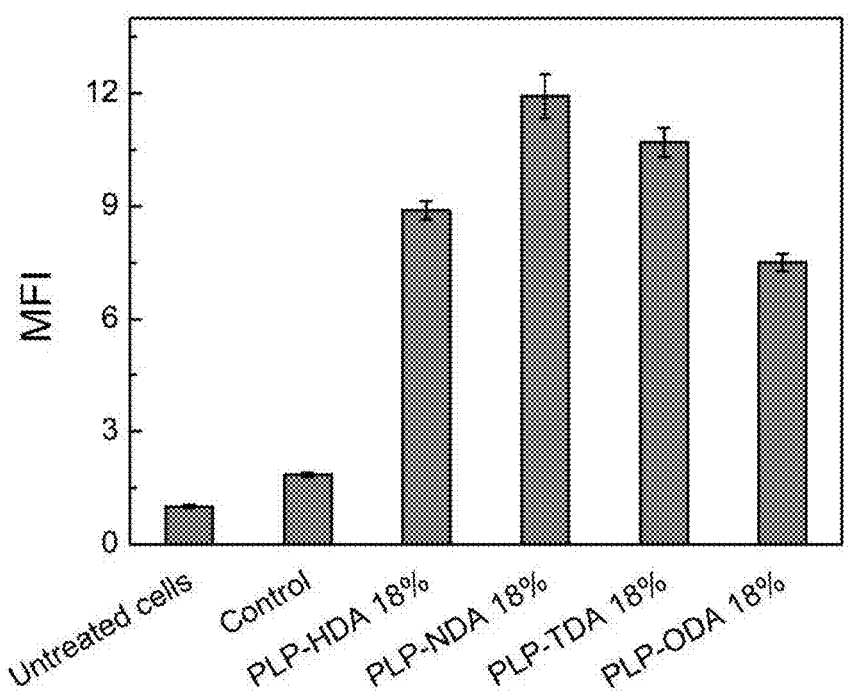

Derivatives of PLP containing alkyl chains with different lengths facilitated FITC-dextran delivery (FIG. 9). The delivery efficiency was ranked in the order of PLP-NDA 18%>PLP-TDA 18%>PLP-HDA 18%>PLP-ODA 18%. No significant intracellular delivery was observed when the cells were incubated with FITC-dextran only at pH 6.5.

EXAMPLE 10

Figure 11:
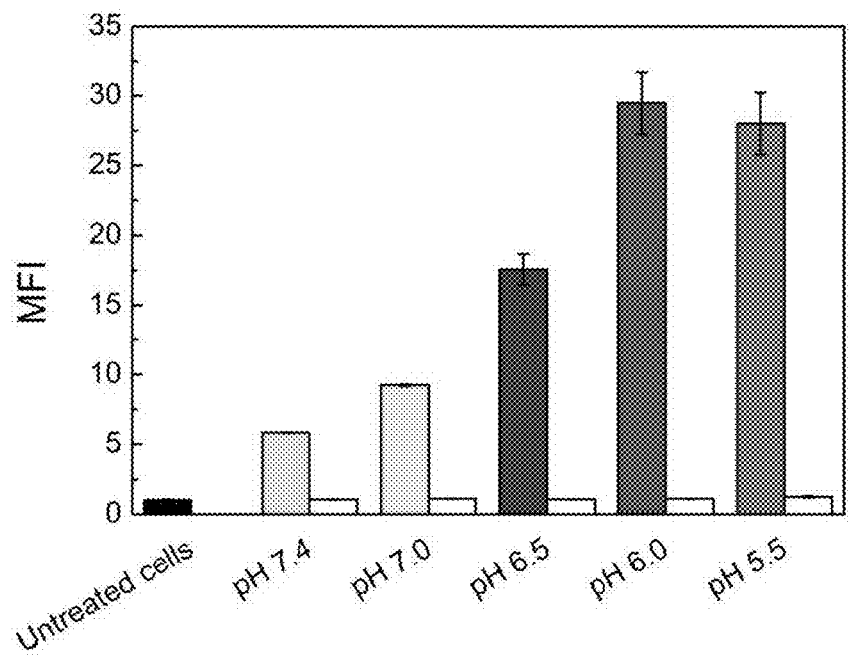
Figure 11:
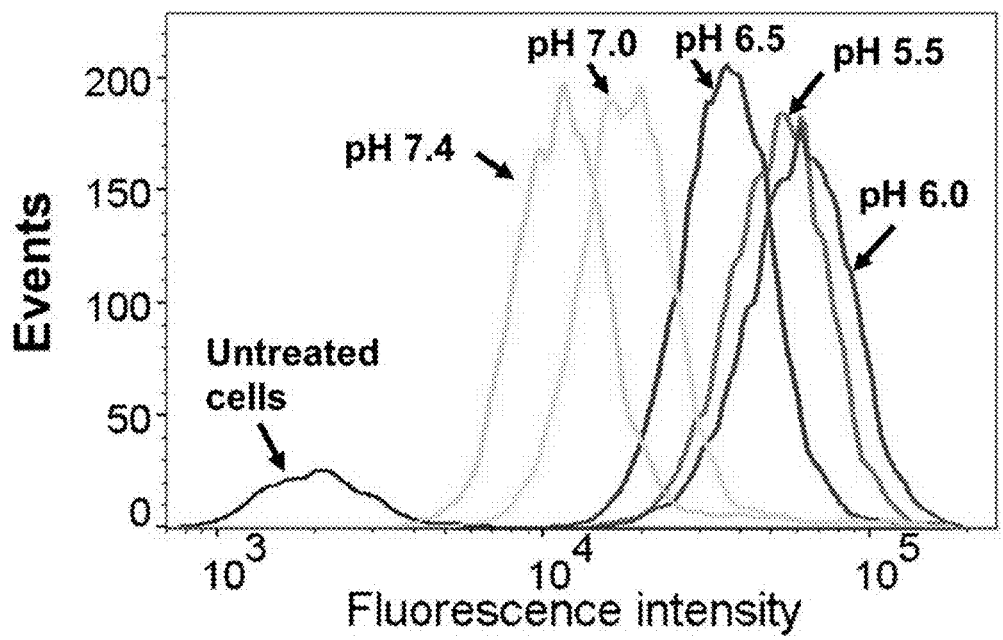

PLP-NDA 18% mediated intracellular payload delivery in response to extracellular pH, as demonstrated by confocal microscopy (FIG. 10) and flow cytometry (FIG. 11). Limited intracellular delivery of FITC-dextran was detected when the cells were co-incubated with PLP-NDA 18% and FITC-dextran at pH 7.4. The delivery efficiency considerably increased with decreasing pH. The highest delivery efficiency was achieved at extracellular pH 5.5-6.5.

EXAMPLE 11

Confocal microscopy (FIG. 12) and flow cytometry (FIG. 13) measurements showed that, when HeLa cells were co-incubated with PLP-NDA 18% and FITC-dextran at pH 6.5, intracellular delivery started only after 10 min of treatment. The delivery efficiency increased with the extension of incubation time.

EXAMPLE 12

The wide applicability of PLP-NDA 18% mediated intracellular delivery was demonstrated via confocal microscopy (FIG. 14) and flow cytometry measurements (FIG. 15). Strong diffuse green fluorescence was observed in all cell types tested, including HeLa adherent epithelial cells (human cervical cancer cells), CHO adherent epithelial cells (Chinese hamster ovary cells), A549 adherent epithelial cells (human lung cancer cells), SU-DHL-8 suspension B lymphocyte cell line (human lymph node cells), MES-SA adherent epithelial cell line (human uterus cancer cells), MES-SA/DX5 adherent multi-drug resistant cell line and human mesenchymal stem cells (hMSCs, human bone marrow derived). This confirms that the comb-like polymer can efficiently deliver macromolecules into a variety of cell types, including adherent and suspension cells, cancerous and non-cancerous cells, multidrug resistant cells, lymphocytes and stem cells.

EXAMPLE 13

Figure 16:
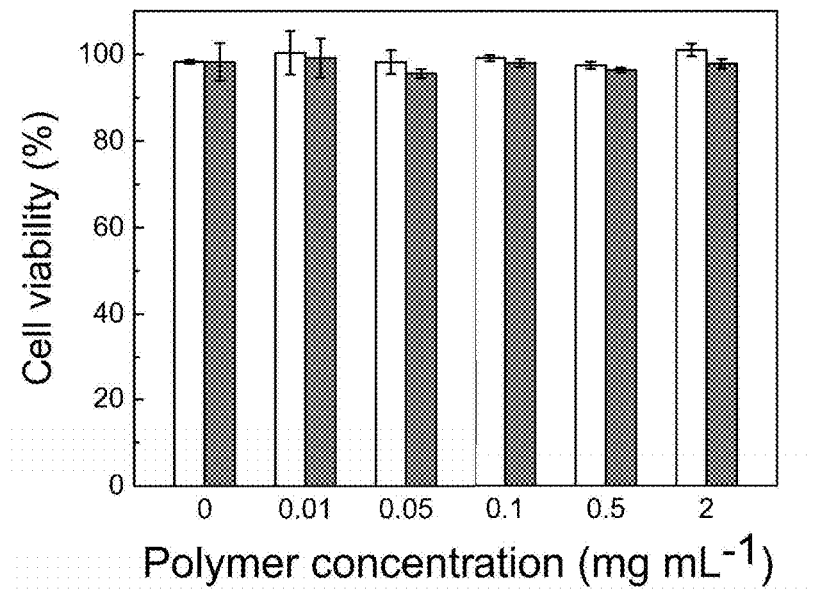
Figure 16:
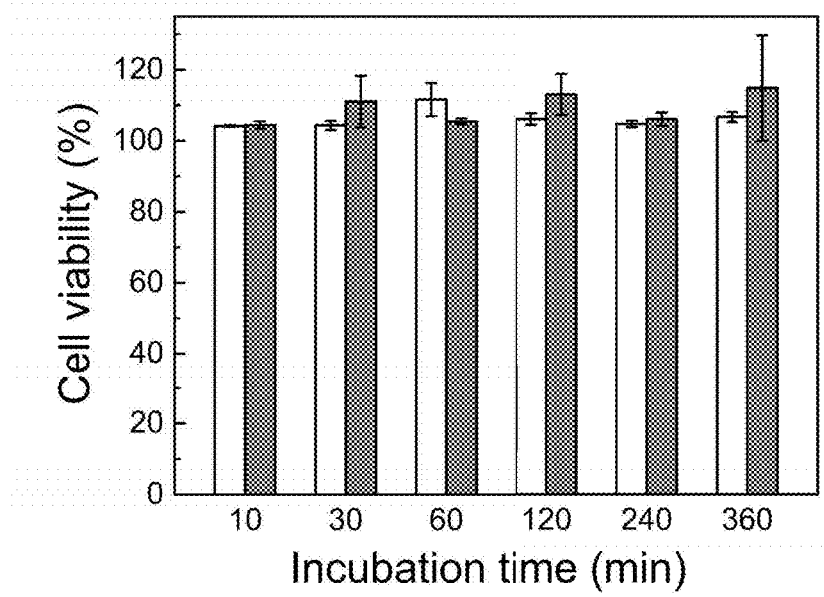
Figure 16:
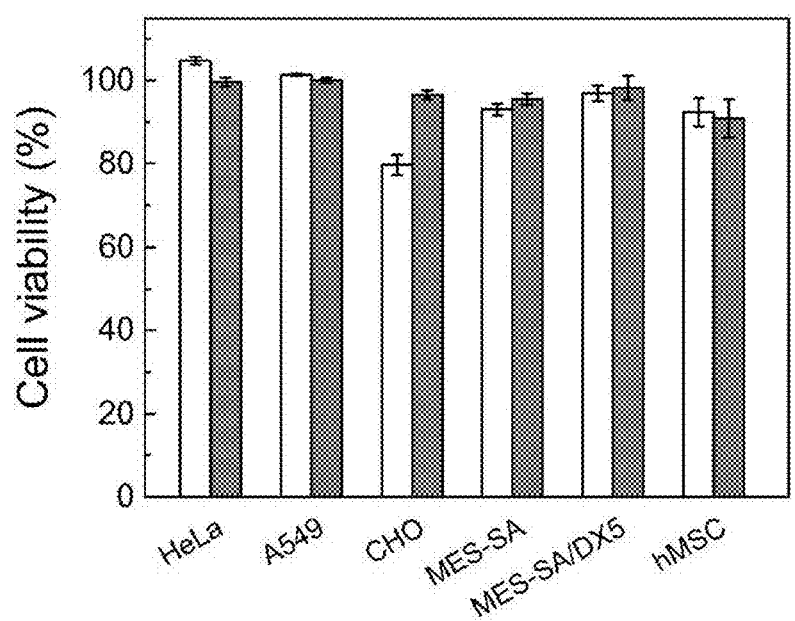

In vitro cytotoxicity of PLP-NDA 18% against different cell types at various extracellular pHs, polymer concentrations and time durations was evaluated (FIG. 16). The polymer was well tolerated by a variety of cell types within a wide polymer concentration range after various durations of incaution at both acidic and neutral pHs.

EXAMPLE 14

Trehalose loading and haemolysis of erythrocytes was monitored at different conditions such as incubation time and polymer concentration. Increase of the intracellular trehalose concentration could be measured after 15 min incubation with PLP-NDA 18% (300-800 μg mL$^{-1}$) at pH 7.05. An intracellular trehalose concentration of 215 mM was achieved after cells were incubated in 800 μg mL$^{-1}$ PLP-NDA 18% for 60 min (FIG. 17). Haemolysis of erythrocytes was found to be increased relative to the PLP-NDA polymer concentration (FIG. 18).

EXAMPLE 15

Trehalose uptake and haemolysis is pH dependent. Uptake was increased after 15 min of treatment at a pH between 6.1 and 5.6 and haemolysis was low for all concentrations tested (FIG. 19). Haemolysis at this pH was reduced when cells were treated with 600 μg mL$^{-1}$ PLP-NDA (FIG. 20).

EXAMPLE 16

Trehalose loading and haemolysis is dependent on PLP-NDA incubation time (FIG. 21) and temperature (FIG. 22). The intracellular trehalose concentration in erythrocytes in 0.36 M trehalose solution and with addition of 800 μg mL$^{-1}$ PLP-NDA 18% at pH 6.1 reached a high level up to approximately 0.3 M after 60 min of loading, with haemolysis below 30%. Among the temperature range (31-40° C.) tested, the intracellular trehalose and haemolysis peaked at 37° C.

EXAMPLE 17

Trehalose loading and haemolysis is dependent on the extracellular trehalose concentration. Incubation of cells in a solution containing 0.36 M trehalose and 800 μg mL$^{-1}$ PLP-NDA 18% for 1 h resulted in haemolysis of below 30% and a high intracellular trehalose concentration of 300 mM (FIG. 23).

EXAMPLE 18

The impact of the length of hydrophobic pendant chains and the degree of substitution on trehalose loading (FIGS. 24 and 26) and haemolysis (FIGS. 25-26) of cells was monitored. The PLP substituted with NDA (C7) at the 18% degree of substitution showed the optimal intracellular trehalose loading.

EXAMPLE 19

The membrane-impermeable dye calcein was mixed with trehalose to trace its translocation into cells by confocal microscopy (FIG. 27) and flow cytometry (FIG. 28). As shown PLP-NDA 18% induced intracellular delivery of payloads (calcein and trehalose) after only 15 min of treatment, much more rapidly than PP50 (PLP grafted with hydrophobic amino acid phenylalamine) which has been reported to take as long as 9 hours. PLP-NDA 18% induced intracellular delivery was also considerably more efficient than PP50. At pH 7.4, both polymers mediated limited intracellular delivery.

EXAMPLE 20

Figure 29:
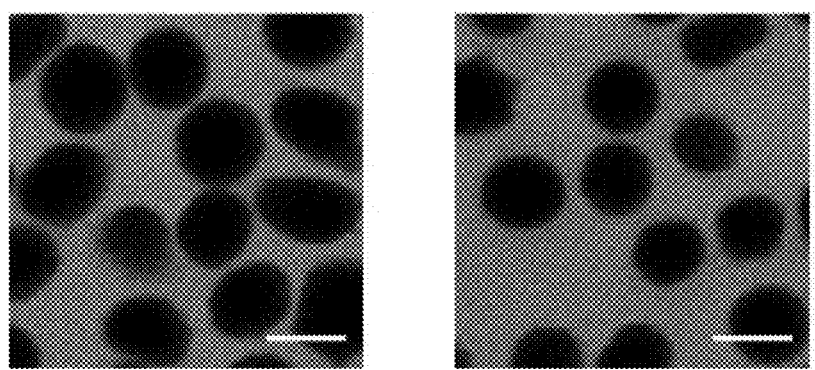

Membrane integrity of the erythrocytes post sugar loading was evaluated (FIG. 29). The erythrocyte membrane remained impermeable after sugar loading in the absence or in the presence of PLP-NDA 18%, as calcein was not able to permeable through cell membrane after washing and pH adjustment to 7.4. This suggests that the polymer didn't cause permanent membrane damage and the polymer mediated membrane permeabilization was reversible.

EXAMPLE 21

The membrane surface roughness of erythrocytes mediated by different polymers was compared using topographic AFM (FIG. 30, Table 5). The cell surface roughness was ranked in the order of PLP-NDA 18%>PP50>control, suggesting that PLP-NDA 18% facilitated much stronger interaction with cell membrane compared to PP50

EXAMPLE 22

The erythrocytes (FIG. 31) treated with 800 μg mL$^{-1}$ PLP-NDA 18% and 0.36 M trehalose solution at pH 6.1 for 15 min can reach an approximately survival of approximately 85%, significantly higher than the cells treated with 0.36 trehalose solution only. The change of cryosurvival was not significant when the duration of cryopreservation was extended from 5 min to 168 hours.

The invention claimed is:
1. A poly(lysine isophthalamide) derivative comprising general formula (I):

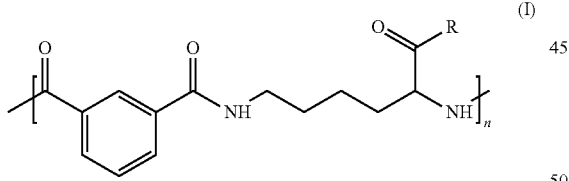

wherein R comprises
NR$^1$R$^2$ or OH wherein at least one of R are NR$^1$R$^2$;
R$^1$ and R$^2$ each independently comprises:
H;
C$_{6-30}$ alkyl, C$_{6-30}$ alkenyl or C$_{6-30}$ alkynyl, C$_{6-10}$ aryl or C$_{5-10}$ heteroaryl; wherein
Alkyl, alkenyl and alkynyl groups R$^1$ and R$^2$ are optionally substituted with one or more substituents selected from halo, cyano, nitro, diazonium, —OP(O)OR$^3$OR$^4$, —PR$^3$R$^4$, NR$^3$R$^4$, =NR$^3$, =O, C(O)OR$^3$, OR$^3$, SR$^3$, C(O)SR$^3$, C(O)NR$^3$R$^4$, azide, C$_{3-7}$ cycloalkyl, C$_{3-10}$ heterocyclyl, C$_{6-14}$ aryl or C$_{4-14}$ heteroaryl;
wherein cycloalkyl, heterocyclyl, aryl and heteroaryl groups are optionally substituted with one or more substituents selected from C$_{1-10}$ alkyl, C$_{1-10}$ haloalkyl, C$_{2-10}$ alkenyl, C$_{2-10}$ alkynyl, halo, cyano or nitro,
NR$^3$R$^4$, C(O)OR$^3$, OR$^3$, SR$^3$, azide, OP(O)OR$^3$OR$^4$, —PR$^3$R$^4$, aryl substituted with R$^3$ and heteroaryl substituted with R$^3$ and, where chemically appropriate, =O; and
wherein each of R$^3$ and R$^4$ is independently H or C$_{1-10}$ alkyl, C$_{2-10}$ alkenyl, C$_{2-10}$ alkynyl, C$_{6-10}$ aryl;
aryl and heteroaryl groups R$^1$ and R$^2$ are optionally substituted with one or more substituents selected from C$_{1-16}$ alkyl, halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, C$_{6-14}$ aryl, C$_{4-14}$ heteroaryl or S—CH$_2$C(O)NR$^5$R$^6$;
wherein alkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$;
wherein aryl and heteroaryl groups are optionally substituted with one or more substituents selected from C$_{1-10}$ alkyl, C$_{1-10}$ haloalkyl, C$_{2-10}$ alkenyl, C$_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$;
wherein R$^3$ and R$^4$ are as defined above and R$^5$ and R$^6$ are each independently H, C$_{1-6}$ alkyl optionally substituted with OR$^3$ or halo or C$_{6-14}$ aryl optionally substituted with C$_{1-6}$ alkyl, OH, O(C$_{1-6}$ alkyl) or O—C$_{6-14}$ aryl; or
R$^1$ and R$^2$ together with the nitrogen atom to which they are attached form a 5-12-membered heterocyclic ring optionally containing one or more additional heteroatoms selected from N, O and S and optionally substituted with one or more substituents selected from C$_{1-16}$ alkyl, C$_{1-16}$ haloalkyl, halo, cyano, nitro, diazonium, =O, —OP(O)OR$^3$R$^4$, —PR$^3$R$^4$, NR$^3$R$^4$, C(O)OR$^3$, OR$^3$, SR$^3$, C(O)SR$^3$, C(O)NR$^3$R$^4$, azide, C$_{6-14}$ aryl or C$_{4-14}$ heteroaryl;
wherein alkyl and haloalkyl groups are optionally substituted with one or more substituents selected from halo, cyano or nitro, NR$^3$R$^4$, C(O)OR$^3$, OR$^3$, SR$^3$, azide, OP(O)OR$^3$OR$^4$, —PR$^3$R$^4$,
wherein aryl and heteroaryl groups are optionally substituted with one or more substituents selected from C$_{1-10}$ alkyl, C$_{1-10}$ haloalkyl, C$_{2-10}$ alkenyl, C$_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$;
wherein R$^3$ and R$^4$ are as defined above; and
n≥4.
2. A poly(lysine isophthalamide) derivative according to claim 1 wherein
R$^1$ and R$^2$ each independently comprises:
H;
C$_{6-30}$ alkyl, C$_{6-30}$ alkenyl or C$_{6-30}$ alkynyl group optionally substituted with one or more substituents selected from halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, C$_{6-14}$ aryl or C$_{4-14}$ heteroaryl,
wherein aryl and heteroaryl groups are optionally substituted with one or more substituents selected from C$_{1-10}$ alkyl, C$_{1-10}$ haloalkyl, C$_{2-10}$ alkenyl, C$_{2-10}$ alkynyl, halo, cyano or nitro, NR$^3$R$^4$, C(O)OR$^3$, OR$^3$, SR$^3$, azide, OP(O)OR$^3$OR$^4$, —PR$^3$R$^4$; and
wherein each of R$^3$ and R$^4$ is independently H or C$_{1-10}$ alkyl, C$_{2-10}$ alkenyl, C$_{2-10}$ alkynyl, C$_{6-10}$ aryl;
C$_{6-10}$ aryl optionally substituted with one or more substituents selected from C$_{1-16}$ alkyl, C$_{1-16}$ haloalkyl, halo, cyano, nitro, diazonium, —OP(O)OR$^3$OR$^4$, —PR$^3$R$^4$, NR$^3$R$^4$, C(O)OR$^3$, OR$^3$, SR$^3$, C(O)SR$^3$, C(O)NR$^3$R$^4$, azide, C$_{6-14}$ aryl or C$_{4-14}$ heteroaryl, wherein alkyl and haloalkyl groups are optionally substituted with one or more substituents selected from halo, cyano or nitro, $NR^3R^4$, $C(O)OR^3$, $OR^3$, $SR^3$, azide, $OP(O)OR^3OR^4$, —$PR^3R^4$;

wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, azide, $OP(O)OR^3OR^4$, —$PR^3R^4$;

wherein $R^3$ and $R^4$ are as defined above; or $R_1$ and $R_2$ together with the nitrogen atom to which they are attached to form a 5-12-membered heterocyclic ring optionally containing one or more additional heteroatoms selected from N, O and S and optionally substituted with one or more substituents selected from $C_{1-16}$ alkyl, $C_{1-16}$ haloalkyl, halo, cyano, nitro, diazonium, —$OP(O)OR^3OR^4$, —$PR^3R^4$, $NR^3R^4$, $C(O)OR^3$, $OR^3$, $SR^3$, $C(O)SR^3$, $C(O)NR^3R^4$, azide, $C_{6-14}$ aryl or $C_{4-14}$ heteroaryl;

wherein alkyl and haloalkyl groups are optionally substituted with one or more substituents selected from halo, cyano or nitro, $NR^3R^4$, $C(O)OR^3$, $OR^3$, $SR^3$, azide, $OP(O)OR^3OR^4$, —$PR^3R^4$, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, azide, $OP(O)OR^3OR^4$, —$PR^3R^4$;

wherein $R^3$ and $R^4$ are as defined above; and n≥4.

3. A poly(lysine isophthalamide) derivative according to claim 1 wherein $R^1$ is as defined in claim 1 and $R^2$ is $C_{6-30}$ alkyl, $C_{6-30}$ alkenyl or $C_{6-30}$ alkynyl, $C_{6-10}$ aryl or $C_{5-10}$ heteroaryl, any of which is optionally substituted as defined in claim 1.

4. A poly(lysine isophthalamide) derivative according to claim 3, wherein $R^1$ is H, $C_{6-30}$ alkyl, $C_{6-30}$ alkenyl or $C_{6-30}$ alkynyl, any of which may optionally be substituted as defined in claim 1 and $R^2$ is $C_{6-30}$ alkyl, $C_{6-30}$ alkenyl or $C_{6-30}$ alkynyl, any of which may optionally be substituted as defined in claim 1.

5. A poly(lysine isophthalamide) derivative according to claim 4 wherein
$R^1$ is H or $C_{6-30}$ alkyl, $C_{6-30}$ alkenyl or $C_{6-30}$ alkynyl, any of which is unsubstituted or is substituted with F, Cl, OH, SH, methoxy or ethoxy; and
$R^2$ is $C_{6-30}$ alkyl, $C_{6-30}$ alkenyl or $C_{6-30}$ alkynyl, any of which is unsubstituted or is substituted with F, Cl, OH, SH, methoxy or ethoxy.

6. A poly(lysine isophthalamide) derivative according to claim 5 wherein $R^1$ is H or unsubstituted $C_{6-30}$ alkyl, unsubstituted $C_{6-30}$ alkenyl or unsubstituted $C_{6-30}$ alkynyl; and $R^2$ is unsubstituted $C_{6-30}$ alkyl, unsubstituted $C_{6-30}$ alkenyl or unsubstituted $C_{6-30}$ alkynyl.

7. A poly(lysine isophthalamide) derivative according to claim 5, wherein $R^1$ is H and $R^2$ is unsubstituted $C_{7-18}$ alkyl.

8. A poly(lysine isophthalamide) derivative according to claim 7, wherein each of $R^1$ and $R^2$ is independently unsubstituted $C_{7-18}$ alkyl.

9. The poly(lysine isophthalamide) derivative according to claim 7 wherein $R^2$ is n-heptyl, n-decyl, n-tetradecyl or n-octadecyl.

10. The poly(lysine isophthalamide) derivative according to claim 9 wherein said $R^2$ is n-decyl.

11. The poly(lysine isophthalamide) derivative according to claim 1 wherein between 0.1-99% of the moieties R are $NR^1R^2$.

12. The poly(lysine isophthalamide) derivative according to claim 11 wherein 3-18% of the moieties R are $NR^1R^2$.

13. The poly(lysine isophthalamide) derivative according to claim 2 wherein each of $R^1$ and $R^2$ is $C_{7-18}$ alkyl, $C_{7-18}$ alkenyl or $C_{7-18}$ alkynyl, any of which may optionally be substituted as defined in claim 2.

14. The poly(lysine isophthalamide) derivative according to claim 13 wherein each of $R^1$ and $R^2$ is $C_7$-alkyl, $C_8$-alkyl, $C_{10}$ alkyl, $C_{14}$ alkyl or $C_{18}$ alkyl, any of which may be optionally be substituted according to claim 2.

15. The poly(lysine isophthalamide) derivative according to claim 1 wherein each of $R^1$ and $R^2$ is optionally substituted with one or more substituents selected from halo, cyano, nitro, azo, diazonium, phosphate, phosphate ester, $NR^3R^4$, $C(O)OR^3$, $OR^3$, $SR^3$, $C(O)SR^3$, $C(O)NR^3R^4$, azide, $C_{6-14}$ aryl or $C_{4-14}$ heteroaryl, wherein aryl and heteroaryl groups are optionally substituted with one or more substituents selected from $C_{1-10}$ alkyl, $C_{1-10}$ haloalkyl, $C_{2-10}$ alkenyl, $C_{2-10}$ alkynyl, halo, cyano or nitro, $NR^3R^4$, $C(O)OR^3$, $OR^3$, $SR^3$, $RN_3$, phosphate, phosphate ester and wherein each of $R^3$ and $R^4$ is independently H or $C_{1-10}$ alkyl, $C_{2-10}$ alkenyl, $C_{2-10}$alkynyl.

16. The poly(lysine isophthalamide) derivative according to claim 2 wherein each of $R^1$ and $R^2$ is optionally substituted with one or more substituents selected from halo, cyano, nitro, $NR^3R^4$, $C(O)OR_3OR^3SR^3$, $C_{6-10}$ aryl or heteroaryl, wherein aryl and heteroaryl groups are optionally substituted with one or more substituents selected from $C_{1-4}$ alkyl, $C_{1-4}$ haloalkyl, halo, cyano or nitro; and wherein each of $R^3$ and $R^4$ is independently H or $C_{1-6}$ alkyl.

17. The poly(lysine isophthalamide) derivative according to claim 1 wherein said peptide is associated, either directly or indirectly with an agent for intracellular delivery to a cell.

18. The poly(lysine isophthalamide) derivative according to claim 17 wherein said agent is covalently or non-covalently associated with said poly(lysine isophthalamide) derivative.

19. The poly(lysine isophthalamide) derivative according to claim 18 wherein said agent is a therapeutic agent.

20. The poly(lysine isophthalamide) derivative according to claim 18 wherein said agent is an imaging agent.

21. The poly(lysine isophthalamide) derivative according to claim 18 wherein said agent is a cell preservation agent.

22. A process for the preparation of poly(lysine isophthalamide) derivative according to claim 1 comprising the steps
   i) polymerization of aqueous lysine methyl ester.2HCl with an equivalent amount of isophthaloyl chloride in acetone and subsequent hydrolysis in DMSO with ethanolic sodium hydroxide, and
   ii) conjugation of R, wherein R comprises $NR^1R^2$ and is defined as above onto the polymer backbone via dicyclohexylcarboiimide/dimethylaminopyridine (DCC/DMAP) coupling; or
      conjugation of R is via 1-Ethyl-3-(3-dimethylaminopropyl)-carbodiimide (EDC)/N-Hydroxysuccinimide (NHS) coupling.

23. A composition comprising a poly(lysine isophthalamide) derivative according to claim 1.

24. The composition according to claim 23 wherein the agent is a therapeutic agent and the composition is a pharmaceutical composition including a pharmaceutically acceptable carrier.

25. The composition according to claim 23 wherein said composition comprises mammalian cells or a collection of mammalian cells.

26. A composition according to claim 23 for use in the delivery of at least one agent to a mammalian cell, cellular aggregate, tissue or organ.

27. An in vitro or ex vivo method to deliver an agent to a cell comprising:
   i) contacting cells or a cellular aggregate, tissue or organ comprising cells with an effective amount of a composition according to claim 23; and
   ii) incubating said cell, cellular aggregate, tissue or organ to allow permeabilization of said mammalian cells or cellular aggregate, tissue or organ comprising cells thereby delivering said agent.

28. The method according to claim 27 wherein said cell is a mammalian cell.

29. An in vitro or ex vivo method for the preservation of a mammalian cell, cellular aggregate, tissue or organ comprising the steps:
   i) providing a preparation comprising a mammalian cell preparation, mammalian cellular aggregate, tissue or organ and a composition according to claim 23;
   ii) incubating said preparation to permeabilize the mammalian cell membranes of said mammalian cell, cellular aggregate, tissue or organ; and
   iii) contacting said permeabilized cell, cellular aggregate, tissue or organ with one or more preservation agents.

30. The method according to claim 29 wherein said preservation agent is a sugar.

* * * * *